(12) United States Patent  
Walker et al.

(10) Patent No.: US 9,594,954 B1  
(45) Date of Patent: Mar. 14, 2017

(54) SYSTEM INCLUDING AN AUTOMATED BANKING MACHINE AND AT LEAST ONE WEARABLE COMPUTER DEVICE WORN BY AN INDIVIDUAL FOR IDENTIFYING DATA ON A BILL DISPENSED FROM THE AUTOMATED BANKING MACHINE

(71) Applicants: Patricia A. Walker, Medina, OH (US); Ralph E. Jocke, Medina, OH (US)

(72) Inventors: Patricia A. Walker, Medina, OH (US); Ralph E. Jocke, Medina, OH (US)

( * ) Notice: Subject to any disclaimer, the term of this patent is extended or adjusted under 35 U.S.C. 154(b) by 0 days.

(21) Appl. No.: 14/446,413

(22) Filed: Jul. 30, 2014

Related U.S. Application Data

(63) Continuation-in-part of application No. 14/273,991, filed on May 9, 2014, now Pat. No. 9,262,785, which (Continued)

(51) Int. Cl.
*G07D 11/00* (2006.01)
*G07D 7/00* (2016.01)
(Continued)

(52) U.S. Cl.
CPC ......... *G06K 9/00469* (2013.01); *G06Q 40/02* (2013.01); *G07D 11/0066* (2013.01); *G07F 19/203* (2013.01)

(58) Field of Classification Search
CPC .......... G07D 7/00; G07D 7/0033; G07D 7/20; G07D 7/2033; G07D 11/0066; (Continued)

(56) References Cited

U.S. PATENT DOCUMENTS 6,088,585 A * 7/2000 Schmitt ............... G06K 9/0002  
 340/5.83  
2010/0144387 A1* 6/2010 Chou ...................... G07D 7/12  
 455/556.1  
(Continued)

FOREIGN PATENT DOCUMENTS

IT  WO 2013068973 A2 * 5/2013 ............... A61L 2/10

OTHER PUBLICATIONS

"Got fake currency from ATM?". Business Standard. Jun. 11, 2013. (http://www.business-standard.com/article/pf/got-fake-currency-from-atm-113061100214_1.html).*
(Continued)

*Primary Examiner* — Michael G Lee  
*Assistant Examiner* — Suezu Ellis  
(74) *Attorney, Agent, or Firm* — Walker & Jocke

(57) ABSTRACT

An automated banking machine operates to cause financial transfers responsive at least in part to data read from data bearing records. The automated banking machine includes a reader configured to read identifying data from currency bills dispensed from the machine. A wearable computer device configured to be worn by an individual, includes at least one wearable reader that reads identifying data from currency bills. The wearable device is configured to read bill indicia from bills received by an individual while wearing the device. The wearable device is operative to cause a bill source comparison to be made concerning whether identifying data read from a received currency bill corresponds to a bill previously dispensed from the machine. The wearable device is also configured to cause a bill genuineness determination to be made responsive to read bill indicia.

20 Claims, 37 Drawing Sheets

Related U.S. Application Data is a continuation-in-part of application No. 14/281,936, filed on May 20, 2014, now Pat. No. 9,117,327.

(60) Provisional application No. 62/029,210, filed on Jul. 25, 2014, provisional application No. 61/862,696, filed on Aug. 6, 2013, provisional application No. 61/925,393, filed on Jan. 9, 2014.

(51) Int. Cl.
*G07F 19/00* (2006.01)
*G06K 9/00* (2006.01)
*G06Q 40/02* (2012.01)

(58) Field of Classification Search
CPC  G07D 11/0069; G07D 2211/00; G07F 19/20; G07F 19/201; G07F 19/203; G07F 19/211; G06Q 20/1085
See application file for complete search history.

(56) References Cited

U.S. PATENT DOCUMENTS

| | | | |
|---|---|---|---|
| 2011/0259955 A1* | 10/2011 | Laskowski | G06Q 20/1085 235/379 |
| 2011/0284599 A1* | 11/2011 | Sternick | A45F 5/00 224/191 |
| 2012/0077476 A1* | 3/2012 | Paraskevakos | G06Q 20/4016 455/414.2 |
| 2012/0255978 A1* | 10/2012 | Williams | A45F 5/00 224/219 |
| 2013/0063611 A1* | 3/2013 | Papakipos | G06F 1/1686 348/207.11 |
| 2013/0232065 A1* | 9/2013 | Smith | G06Q 20/042 705/43 |
| 2013/0297414 A1* | 11/2013 | Goldfarb | G06Q 40/00 705/14.51 |

OTHER PUBLICATIONS

"Banks may be held responsible for ATM fake notes". The Economic Times. Feb. 8, 2013. (http://articles.economictimes.indiatimes.com/2013-02-08/news/36993011_1_fake-notes-counterfeit-currency-bank-branches).*

"Wear." Merriam-Webster's Collegiate Dictionary. 10th ed. 1998. Print.*

* cited by examiner

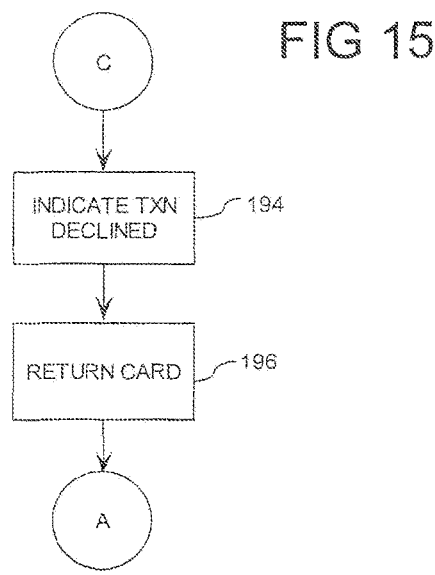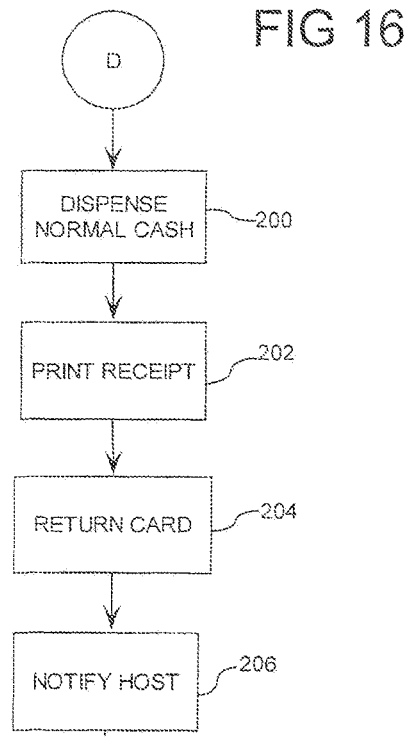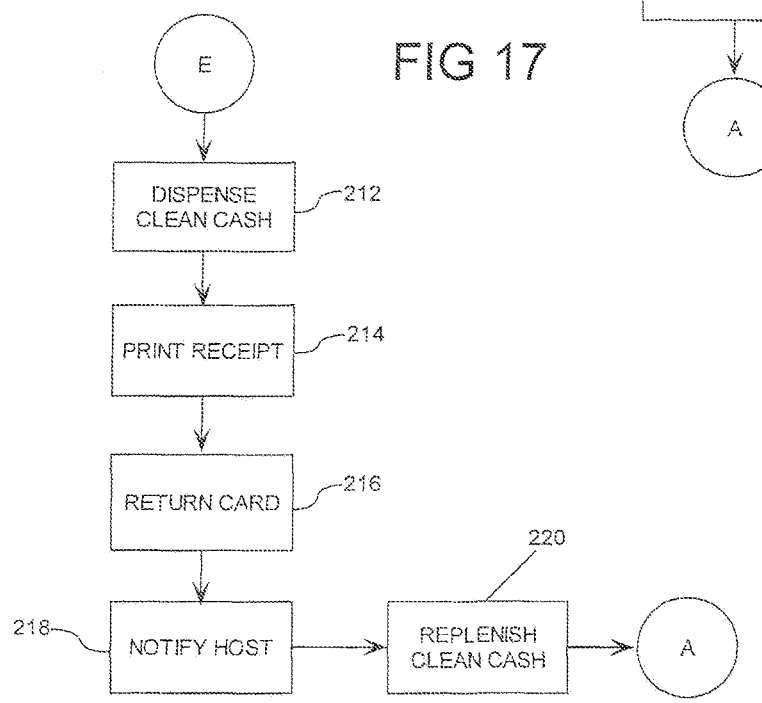

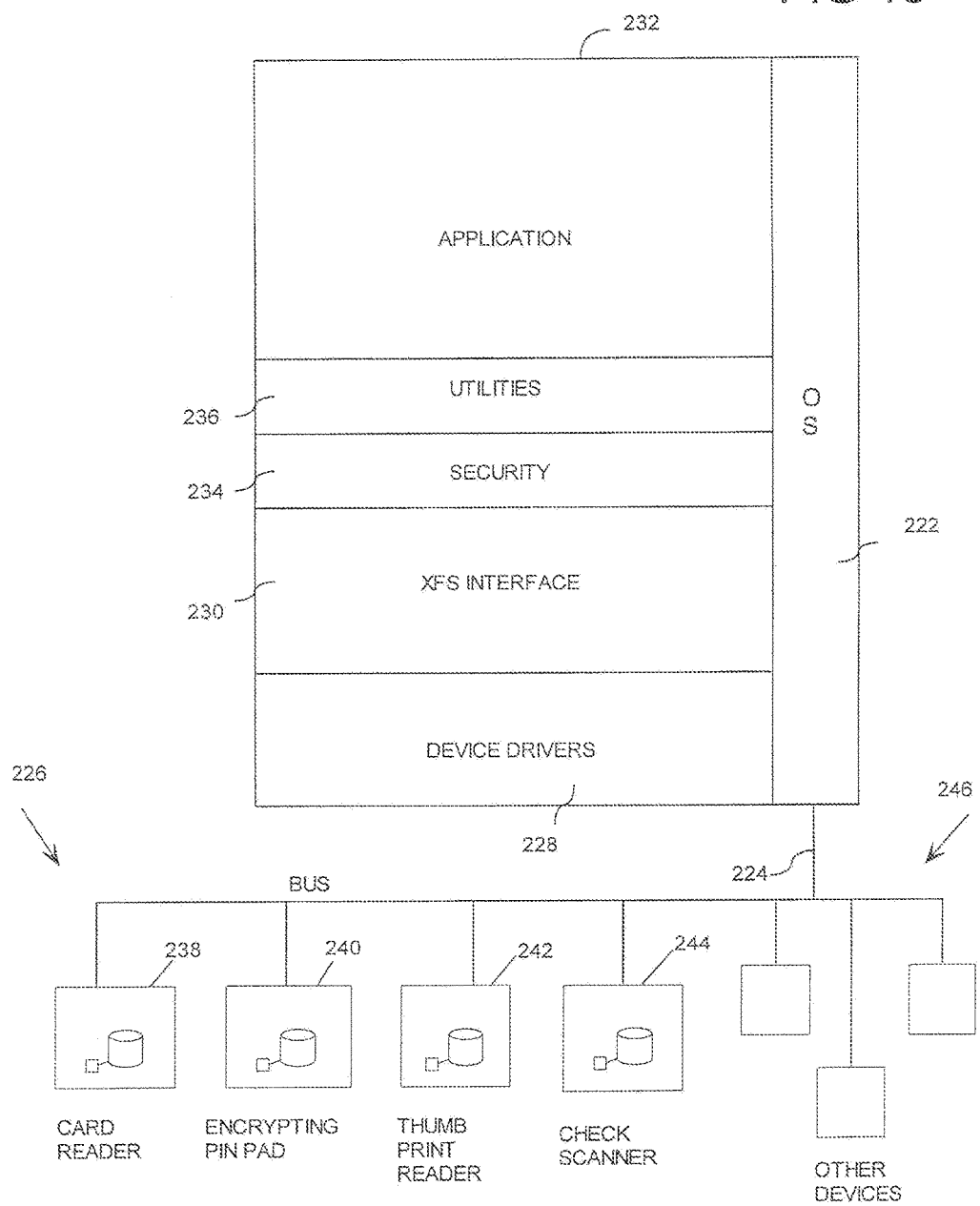

SYSTEM INCLUDING AN AUTOMATED BANKING MACHINE AND AT LEAST ONE WEARABLE COMPUTER DEVICE WORN BY AN INDIVIDUAL FOR IDENTIFYING DATA ON A BILL DISPENSED FROM THE AUTOMATED BANKING MACHINE

TECHNICAL FIELD

This invention pertains to automated banking machines that are controlled responsive to data read from data bearing records such as user cards and which scan and resolve data from documents such as financial checks or currency bills, which may be classified in U.S. Class 235, Subclass 379, Group Art Unit 2887.

BACKGROUND

Automated banking machines may include a card reader that operates to read data from a bearer record such as a user card. The automated banking machine may operate to cause the data read from the card to be compared with other computer stored data related to authorized users. The machine operates in response to the comparison determining that the bearer card corresponds to an authorized system user to carry out at least one transaction which is operative to transfer value to or from at least one account. A record of the transaction is also commonly printed through operation of the automated banking machine and provided to the user. A common type of automated banking machine used by consumers is an automated teller machine which enables consumers to carry out banking transactions. Banking transactions carried out may include the dispensing of cash, the making of deposits, the transfer of funds between accounts, and account balance inquiries. Such machines may additionally receive, optically scan and resolve data from documents such as financial checks. The types of transactions a customer may carry out with an automated banking machine are determined by the capabilities of the particular machine and the programming associated with operating the machine.

Other types of automated banking machines may be operated by merchants to carry out commercial transactions. These transactions may include, for example, the acceptance of deposit bags, the receipt of checks or other financial instruments, the dispensing of rolled coin or other transactions that are required by merchants. Still other types of automated banking machines may be used by service providers in a transaction environment such as at a bank to carry out financial transactions. Such transactions may include, for example, the counting and storage of currency notes or other financial instrument sheets, the dispensing of notes or other sheets, the imaging of checks or other financial instruments and other types of service provider transactions. For purposes of this disclosure, an automated banking machine, an automated transaction machine, an automated teller machine, or an ATM shall be deemed to include any machine that may be used to electronically carry out transactions involving automated transfers of value.

Automated banking machines may benefit from improvements.

SUMMARY OF DISCLOSURE

An automated banking machine that operates responsive at least in part to data read from data bearing records operates to cause financial transfers to or from financial accounts of machine users. The exemplary machine and system provides enhanced security to assure that risks of fraudulent transactions are reduced. Other exemplary arrangements provide for improved user interfaces for operation of automated banking machines. These include improved user interfaces for persons to operate the machine utilizing wearable mobile devices. Other example arrangements provide user interfaces that enable users that are blind or have impaired vision to operate the machine more conveniently and readily.

Other exemplary arrangements provide capabilities for enabling users to achieve a more sanitary operating environment in connection with items that are provided by the machine. Other example arrangements provide for the capability of dispensing articles which are produced and/or configured through operation of the machine, to include data representative of value and which can be used or redeemed for goods or services.

Further exemplary embodiments will be made apparent in the following description of exemplary embodiments and the appended claims.

BRIEF DESCRIPTION OF DRAWINGS

FIGS. 13-17 are a schematic representation of steps carried out by an exemplary controller of an automated banking machine in connection with dispensing disinfected items.

FIG. 18 is a schematic view of software architecture used in connection with an exemplary arrangement of an automated banking machine.

DETAILED DESCRIPTION OF EXEMPLARY EMBODIMENTS

Figure 1:
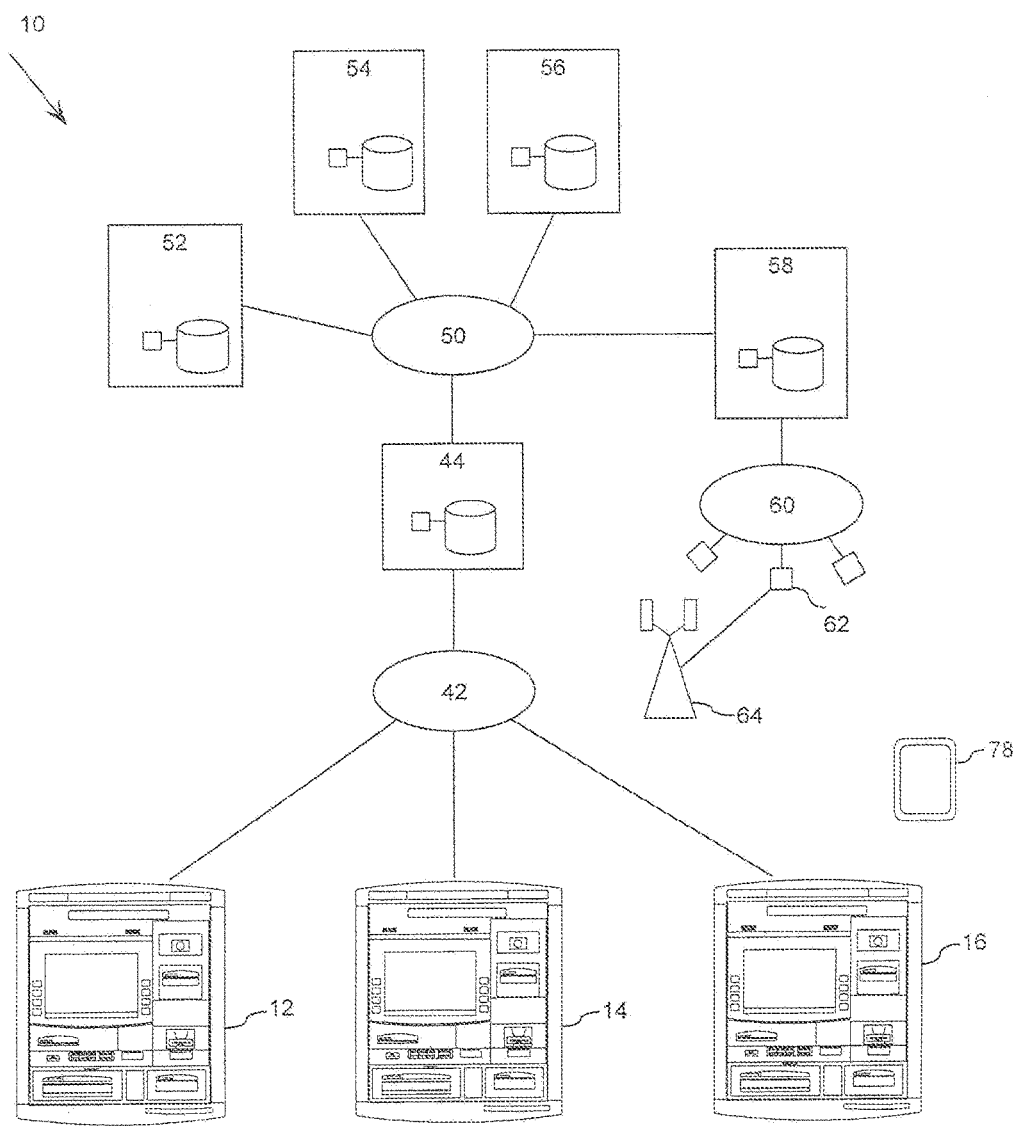
FIG. 1 is a schematic view of a system of an exemplary arrangement including automated banking machines that are operated in response to data read from data bearing records.

Referring now to the drawings and particularly to FIG. 1, there is shown therein an exemplary system 10. System 10 includes a plurality of automated banking machines 12, 14 and 16. Each of the automated banking machines of the exemplary system is operative to cause financial transfers at least one of to or from user financial accounts responsive at least in part to data read from data bearing records. It should be understood that these automated banking machines are exemplary and in other arrangements other types of automated banking machines may be used.

Figure 2:
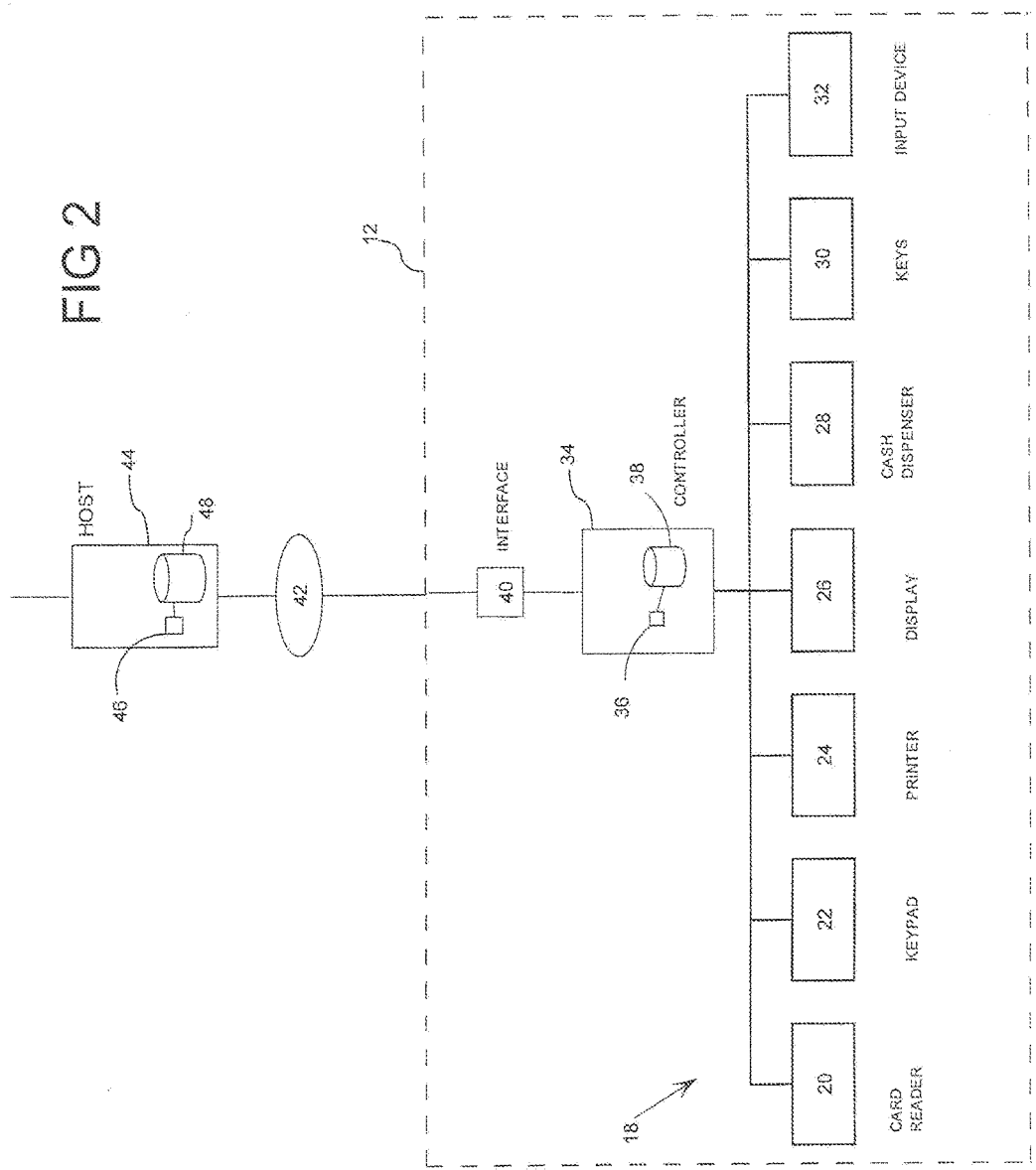
FIG. 2 is a schematic view of the components of an exemplary automated banking machine.

The components of the exemplary automated banking machine 12 are shown schematically in FIG. 2. Automated banking machine 12 includes a plurality of transaction function devices 18. The exemplary transaction function devices in automated banking machine 12 include a card reader 20. Card reader 20 is operative to read data from bearer records such as user cards. The data read through operation of the card reader is usable to identify at least one financial account on which transactions at the machine are to be conducted. The exemplary arrangements may include magnetic stripe card readers, chip type card readers, wireless type card readers or other types of contact or non-contact devices for reading articles which include data that corresponds to financial accounts. In some exemplary arrangements the automated banking machine may include card readers and other features like those described in U.S. Pat. Nos. 7,004,385; 7,284,692; 7,992,776; 7,992,778; and 8,540,142 the disclosures of each of which are incorporated herein by reference in their entirety.

The exemplary automated banking machine further includes a keypad 22. The exemplary machine includes a keypad having a plurality of manually actuatable keys that may be used by machine users to provide inputs. Inputs provided may include alphanumerical inputs or other types of inputs as appropriate to be provided by users for operation of the machine. In exemplary embodiments the keypad may include an encrypting keypad (alternatively referred to herein as an encrypting PIN pad or EPP) which includes internal circuitry that is operative to encrypt inputs that are provided through the keys. Some exemplary arrangements may include features like those shown in U.S. Pat. Nos. 8,540,146; 8,517,262; 7,904,713; 7,896,228; and/or 7,418,592 the disclosures of each of which are incorporated herein by reference in their entirety.

The exemplary automated banking machine 12 further includes a printer 24. Printer 24 of the exemplary arrangement is operative to print paper documents for users of the machine. In some exemplary arrangements the paper documents may include receipts for transactions conducted at the machine. In other exemplary arrangements the printer may be operative to print other documents such as vouchers, scrip, checks, postage or other financial instruments. Some exemplary arrangements may include features like those shown in U.S. Pat. No. 8,424,755 the disclosure of which is incorporated herein by reference in its entirety. Various types of printers may be used in exemplary arrangements such as impact printers, dot matrix printers, laser printers, thermal printers or other suitable types of printers for producing the documents desired to be produced by the machine. It should be understood that some exemplary arrangements may include multiple different types of printers, each of which produce different types of documents that are provided to machine users.

The exemplary automated banking machine further includes a display 26. Display 26 is operative to provide visual outputs to users of the machine. The visual outputs in the exemplary embodiment include instructions to users concerning the operation of the machine. Displays in some exemplary embodiments may include liquid crystal displays, CRT displays, OLED displays or other types of displays that are suitable for providing visual outputs to users.

The exemplary automated banking machine 12 further includes a cash dispenser 28. In some exemplary arrangements the cash dispenser includes one or more mechanisms that are operative to make cash such as currency bills, coin or other currency items stored within the machine selectively available to users of the machine during the course of transactions. In some exemplary arrangements cash dispensers may include mechanisms that operate to provide currency bills to users. For example in some arrangements the cash dispenser and automated banking machine may include features like those described in U.S. Pat. Nos. 8,128,083; 7,261,236; 7,144,006; 6,981,638; and/or 6,945,526 the disclosures of each of which are incorporated herein by reference in their entirety.

Further in other arrangements the cash dispenser 28 may include a currency recycling device. Such currency recycling devices may include for example devices that enable a machine to receive currency bills from users, to validate the received currency bills as genuine, and store such bills within the machine for later dispense to other authorized users. For example some automated banking machines of exemplary arrangements may include features like those shown in U.S. Pat. Nos. 8,251,281; 8,191,771; 8,132,718; 7,992,775; 7,748,615; 7,891,554; 7,971,781; 7,934,642; 6,682,068; 6,131,809; and/or 6,331,000 the disclosures of each of which are incorporated herein by reference in their entirety.

The exemplary automated banking machine further includes a plurality of manually actuatable function keys 30. In some exemplary embodiments the function keys may be disposed at locations adjacent to the display so as to enable users to manually actuate selected keys to make selections output through the display and to provide inputs to the machine. Alternatively other exemplary embodiments may include other types of keys for receiving inputs from users. Such keys may include other arrangements for manually actuatable keys such as a keyboard or other key arrangement. Further in some exemplary arrangements the display may include a touch screen type input device which may include visual representations of keys which can be selected by authorized users to provide inputs to the machine. Of course these types of keys are exemplary of input devices through which users may provide inputs to the machine.

The exemplary automated banking machine 12 further includes an input device 32. Input device 32 in some embodiments includes a wireless portal that is suitable for receiving and communicating wireless signals. This may include for example communicating signals via radio frequency, infrared, Bluetooth™ or other signals that may be received from or communicated with portable wireless devices such as smart phones, portable tablet devices, wearable computers or other items. Further in other exemplary arrangements other types of communications devices may be utilized for receiving inputs and providing outputs from the machine. Of course it should be understood that these transaction function devices 18 are exemplary and in other arrangements, other or additional devices may be used.

The exemplary automated banking machine 12 includes at least one controller 34. The exemplary controller 34 includes one or more circuits which are operative to communicate electrical signals with and control the operation of transaction function devices 18. In the exemplary arrangement the at least one controller 34 includes at least one processor schematically indicated 36 and at least one data store schematically indicated 38. In exemplary arrangements the processor may include a processor suitable for carrying out computer executable instructions that are stored in the one or more associated data stores. The processor includes or is in connection with a non-volatile storage medium including instructions that include a basic input/output system (BIOS). The exemplary arrangements may include, for example, processors produced by Intel Corporation such as Intel Pentium processors or Intel iCore series processors. Of course it should be understood that these processors are exemplary of many types of processors that may be used.

The exemplary data stores used in connection with exemplary embodiments may include any one or more of several types of mediums suitable for holding computer executable instructions. This may include, for example, magnetic media, optical media, solid state media or other types of media such as RAM, ROM, PROMs, flash memory, computer hard drives or any other form of media suitable for holding data and computer executable instructions. Some exemplary embodiments may include features like those described in U.S. Pat. No. 8,474,698 the disclosure of which is incorporated herein by reference in its entirety. Exemplary controllers may include other components such as hardware and/or software interfaces for communication with the transaction function devices.

The exemplary automated banking machine 12 further includes at least one interface 40. Interface 40 may include, for example, a suitable network interface that enables communication between the at least one controller 34 in the banking machine and one or more networks schematically indicated 42. Interface 40 may include one or more circuits which include electrical components suitable to communicate with wired, optical or wireless networks as appropriate for purposes of providing communications with the machine.

As shown in FIGS. 1 and 2 automated banking machine 12 may communicate through one or more networks 42 with one or more host computers schematically indicated 44. First computer 44 includes at least one processor schematically represented 46 which is in operative connection with at least one data store schematically indicated 48. The processor and data store associated with host computer 44 is operative to carry out computer executable instructions that are stored in at least one data store.

As represented in FIG. 1 in the exemplary arrangement, host computer 44 is in operative communication through one or more networks 50 with financial transaction servers 52, 54 and 56. Each of servers 52, 54 and 56 each include at least one processor and at least one associated data store as schematically shown.

In the exemplary arrangement the system further includes at least one remote computer 58. In the exemplary arrangement at least one remote computer 58 is in operative communication with the system through network 50. Remote computer 58 includes at least one processor and at least one data store as schematically shown. Further in the exemplary arrangement remote computer 58 is also in operative connection with other networks such as network 60 that is schematically shown, as well as other servers 62. Further in the exemplary arrangement the at least one remote computer 58 may be in operative connection with wireless communication networks as schematically indicated 64 as well as other types of public or private networks. The configuration of the particular system will depend on the nature of the system and the types of transactions to be conducted.

In operation of the exemplary arrangement a user at an automated banking machine such as automated banking machine 12 is enabled to carry out transactions involving a user's financial account. This is accomplished in the exemplary arrangement by a user providing to the card reader of the machine, a suitable card such as a credit or debit card that includes card data that is usable to identify the financial account associated with the user. The controller 34 of the exemplary automated banking machine is operative in accordance with its programming to cause the card reader to read the data from the user card. The controller further operates to cause the display to output indicia that prompts a user to input other identifying data to the machine such as a personal identification number (PIN) through the keypad 22 of the machine. The controller then operates to cause the user input PIN or other identifying data to be received through the keypad. Alternatively in some arrangements other or additional identifying data may be received. Such data may include biometric data such as a fingerprint input through an input device such as a fingerprint reader. Other identifying data may include a facial recognition scan, an iris scan, a retina scan, voice recognition or other suitable identifying data that may be input via an input device which can receive such inputs. For purposes hereof each of such types of user identifying input data will be referred to as a PIN.

In the exemplary arrangement the controller 34 operates in accordance with its associated programming to cause the display to output messages to the user which ask the user to select the type of transaction that they wish to conduct through operation of the machine. For purposes of this example, the user will select a cash dispense transaction which the user indicates by providing inputs by pressing the appropriate keys 30 of the machine. In the exemplary arrangement, in response to the user selecting a cash dispense transaction, the at least one controller 34 operates to provide outputs through the display to the user prompting the user to input the amount of cash they wish to have dispensed in connection with the transaction. The controller then operates to cause the user input amount to be received through operation of the keypad 22 or other user input device of the machine.

In response to receiving these items of information from the machine user, the exemplary controller 34 operates in accordance with its programming to cause one or more messages to be sent to the host 44. The messages sent to the host 44 are transmitted through the network interface 40 and through the one or more networks 42 to the host 44. The messages sent by the automated banking machine to the host include data corresponding to the inputs provided by the user to the machine.

In the exemplary arrangement the host 44 operates in accordance with its programming to determine if the data read from the user card corresponds to a user financial account that is authorized to conduct a transaction at the machine. This is accomplished in the exemplary arrangement by the processor 46 of the host 44 determining if the card data corresponds to data stored in the one or more data stores 48 associated with the host. In this exemplary arrangement if the data read from the user card corresponds to an account that is authorized to conduct a transaction through operation of the machine, the host then determines if the customer input PIN corresponds to user identifying data associated with that particular account. This is accomplished by comparing data corresponding to the input PIN to data stored in the at least one data store 48. Thereafter if the PIN data that is input corresponds to the PIN associated with the account, the host computer then operates in accordance with its programming to determine if the financial account of the machine user includes a balance that is at least equal to the amount that the user has requested to be dispensed from the automated banking machine. The host computer does this by comparing the financial account data stored in one or more data stores regarding the balance in the account to the amount requested by the machine user.

If the host computer determines that the card data and PIN data are authorized and that the user's account has sufficient funds to enable the user to withdraw the amount requested, the host then operates in accordance with its programming to send one or more messages to the automated banking machine. The messages sent by the host computer are indicative that the transaction requested by the user is authorized to be carried out. Of course it should be understood that in the event that the card data does not correspond to the account of a user authorized to conduct a transaction at the machine or if the PIN data is not appropriate for that account, then the host computer will send one or more messages to the machine that indicate that the transaction is not authorized. Likewise if the host computer determines that the user does not have a suitable balance in their account to cover the requested cash withdrawal, the host computer will likewise send one or more messages indicating that the transaction is not authorized. In cases where it is indicated that the transaction is not authorized, the at least one controller 34 operates in accordance with its programming to provide one or more outputs through the display 26 to indicate to the user that the transaction is declined. The exemplary controller further operates in accordance with its programming to return the user's card to the user through operation of the card reader. Thereafter the machine returns to the waiting state to conduct another transaction that will start with the input of another card.

In the exemplary arrangement if the one or more messages sent by the host to the automated banking machine indicate that the transaction is authorized, the at least one controller 34 operates in accordance with its programming to cause the cash dispenser to operate. The cash dispenser is operated to make available to the user of the machine, cash corresponding to the amount of cash that the user has requested. The exemplary controller also operates in accordance with its programming to cause the printer 24 of the machine to operate to produce a receipt for the user which indicates the details of the transaction including the value of the cash dispensed.

In the exemplary arrangement the controller 34 also includes one or more records in its data store 38 regarding the carrying out of the transaction and the fact that the cash was dispensed. Further the controller operates in accordance with its programming to send one or more messages to the host computer 44 to indicate that the cash dispense was successfully carried out for the user. In response to the receipt of such messages, the exemplary host operates in accordance with its programming to assess a charge to the user's account corresponding to the value of the cash dispensed.

Of course the process described is utilized for authorizing transactions in situations where host 44 has access to the data necessary to authorize financial transfers for the particular user at the machine. In some exemplary transactions, the host 44 may not have direct access to the data associated with the particular user's account that is sufficient to authorize the user's requested transaction. In such arrangements when the host 44 receives the data related to the requested transaction, the host 44 will operate in accordance with its programming to determine that it does not have the capability to determine whether the transaction requested should be authorized. In such arrangements the host 44 operates in accordance with its programming to route the transaction data in one or more messages to the appropriate network such as network 50 which includes the remote server such as server 52, 54 or 56 that can determine whether the transaction should be authorized.

In the exemplary arrangements the transaction data routed to the appropriate remote server is then analyzed in a manner like that previously described in connection with host 44 to determine if the card data corresponds to an account that is authorized to conduct a transaction through operation of the machine. Further the appropriate remote server operates in accordance with its programming to determine if the customer input PIN corresponds to an authorized user of the account and whether the user account has sufficient funds to cover the requested cash withdrawal. The remote server then operates in accordance with its programming to communicate through the network 50 to the host 44, messages which include information on whether the transaction requested is to be authorized or denied. The host 44 then communicates the appropriate messages to the machine. If the transaction is authorized, the machine communicates that it successfully carried out the transaction to the host 44. The host 44 then communicates this information through the one or more networks 50 to the appropriate remote server. The server then causes the user's account to be assessed an amount corresponding to the value of the cash dispensed.

It should be understood that the approaches described are exemplary. In addition other types of transactions such as deposits, account balance inquiries, check deposit transactions, check cashing transactions, converting electronic value stored on a mobile device to cash or vice versa, cash accepting transactions, or other types of transactions may be conducted in other exemplary embodiments. Further exemplary systems may include features like those described in the following U.S. Patents, the disclosures of which are incorporated herein by reference in their entirety: U.S. Pat. Nos. 8,365,985; 8,376,219; 7,934,644; 7,857,208; 7,844,512; 7,819,309; 7,689,509; 7,653,601; 7,582,944; 7,533,805; and 6,966,487.

In some exemplary embodiments the at least one remote computer 58 operates to identify situations where fraudulent transactions may be occurring. For example in some situations where card data and PIN data for a financial account has been stolen by criminals, numerous fraudulent cards may be produced by criminals in different parts of the country or in various countries of the world. These criminals may conduct numerous frequent transactions on the account until the account balance is depleted. Often these transactions may be occurring at numerous different automated banking machines or at other types of terminals where value is given, such as at a point of sale or service in diverse locations. The fact that numerous transactions are occurring in rapid succession on a given account may not be realized until after the criminals have successfully depleted a significant portion of the funds in the account for which the card and/or PIN data or other authorized user data that enables carrying out transactions has been stolen.

In the exemplary arrangement at least one remote computer 58 is operated to identify situations where transactions are occurring on a particular account and to provide an alert message in the event a particular account is having an abnormally high number of transactions attempted thereon. By determining that a particular account is experiencing an abnormally high level of activity, the remote computer can provide the alert message so as to enable the entity which holds the account to take appropriate action such as to suspend all further transaction activity. Further in the exemplary arrangement the at least one remote computer does not have the capability to identify the account number or other data for the particular account. Rather the remote computer receives encrypted or other data which is unique to each account but which cannot be utilized to determine the actual account number. Thus the at least one remote computer does not have the associated security risks that would be associated with having such actual account data transmitted thereto over wide area networks, or even public networks, which may be accessed by unauthorized persons.

In the exemplary arrangement the host computer 44 as well as each of the remote servers, for example servers 52, 54 and 56, each have associated programming that operates to produce encrypted data that corresponds to the account number data for each transaction that is requested at an automated banking machine. In exemplary arrangements the encrypted data may correspond to a one-way hash or other algorithmic result that is produced from the account number data either alone or in combination with other data. The algorithmic result that is produced results in encrypted data that in the exemplary embodiment is unique to the particular account number, but that may not be used to resolve the account number except by the particular computer that produced the encrypted data. In some exemplary arrangements the encrypted data may be used directly for purposes of comparison while in other arrangements the encrypted data may need to be mathematically manipulated using other values in order to resolve data that may be compared to other data to identify a common account. Further in the exemplary arrangements the host computer 44 and other servers may operate to provide secure communication through the one or more networks 50 with the at least one remote computer 58.

Such secure remote communication may include various approaches such as secure socket layer communications or public key cryptography that ensures that the encrypted data sent from the originating computer is multiply encrypted and can only deliver the encrypted data to the at least one remote computer 58. Of course these approaches are exemplary and in other arrangements other approaches may be used.

Figure 3:
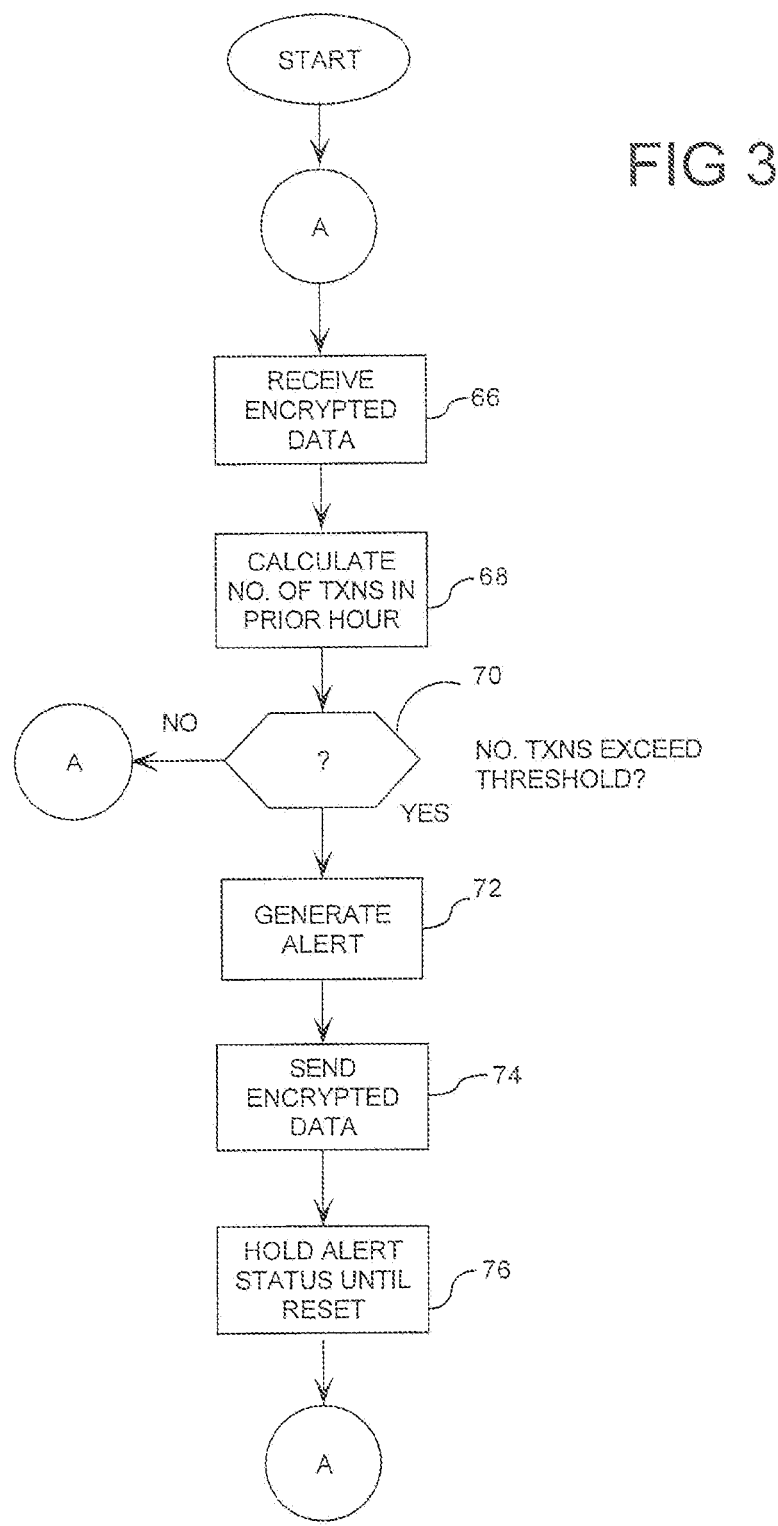
FIG. 3 is a schematic view of steps carried out in operation of at least one remote computer in connection with an exemplary banking machine system.

Logic carried out by the at least one remote computer 58 is represented schematically in FIG. 3. In the exemplary arrangement the at least one remote computer operates to receive the encrypted data from the host computer or server that has received a transaction request related to an account. This is represented by a step 66. The at least one computer then operates in accordance with its programming to review the received encrypted data and to calculate the number of other transactions in which the same or corresponding encrypted data that corresponds to the same account has been received within a prior time period. This may include, for example, a time period which is a rolling window, such as the previous one hour. This is represented by a step 68. Of course it should be understood that this approach is exemplary and in other arrangements other calculations may be made, such as a total number of transactions that have been conducted on the particular account, the elapsed time since the last transaction or the number of transactions that were conducted within a fixed time window. Various approaches may be taken depending on the particular analysis to be conducted to identify an abnormal situation which represents a possible circumstance involving stolen card data.

In the exemplary arrangement the at least one remote computer 58 operates in accordance with its programming to determine based on the calculated number of transactions, whether the transaction count has exceeded a programmed threshold. This is represented in a step 70. If the number of occurrences of receipt of the encrypted data which represents the number of transactions carried out on a particular account, does not exceed the threshold based on the receipt of the most recent occurrence, the computer operates in accordance with its programming to defer any action. However, in the event that the number of transactions has exceeded the programmed threshold within the set rolling time window, the at least one computer operates to generate one or more messages or statuses which comprise an alert. This is represented by a step 72. In some exemplary arrangements the at least one computer may be operated to respond promptly to the received encrypted data so as to indicate to the server or host computer generating the encrypted data that there is a possible problem. This received data is usable by the server or host computer to cause a denial of the then pending transaction and/or further transactions which are requested on the account. In alternative arrangements other analysis in accordance with the programming of the remote computer 58 may be conducted. This may include for example evaluating the timing between successive transactions. In this case the computer determines if transactions are happening more quickly than a threshold, and if so, generates a signal corresponding to an alert. In some embodiments the computer may monitor and evaluate multiple factors in determining whether to generate an alert.

Further in the exemplary arrangement responsive to the generation of the alert, the at least one remote computer 58 is operative to send the data corresponding to the encrypted data to other computers operatively connected in the system that might receive transaction requests related to the account. The sending of this encrypted data to the computers causes the computers to operate in accordance with their programming to store in their associated data stores the encrypted data or other data that is produced when a transaction on that account is requested. Thus by holding the data corresponding to the encrypted data or data that can be used to identify a transaction requested on the same account in the one or more data stores associated with the servers 52, 54 and 56 as well as host 44, such systems may immediately take appropriate steps in accordance with their programming, such as to deny a transaction whenever a transaction on an account is requested and the mathematical manipulation of that account data to produce encrypted data corresponds to the encrypted data for which the alert has been generated. Further in some exemplary systems the receipt of the alert message and encrypted data which can be used to identify transactions which may be suspect, may be utilized by the hosts, servers and remote computer to take steps to try to minimize loss associated with the possible fraudulent transactions. This may include, for example, notifying authorities of the particular transactions which were conducted recently on the account and/or the locations where such transactions occurred. It may also include storing and/or transmitting video surveillance data or taking other appropriate steps that may be useful to identify and apprehend criminals who may be conducting fraudulent transactions on the account.

In the exemplary arrangement the at least one remote computer 58 is operative to maintain the alert status associated with the particular encrypted data until certain programmed steps are taken. For example, such status may be maintained until the at least one remote computer receives messages that the alert status associated with that particular encrypted data should no longer be maintained. This is represented by the step 76.

Of course it should be understood that the foregoing approach to identifying a possible situation where account data has been stolen and is being used fraudulently is exemplary, and in other embodiments other approaches may be used. This may include, for example, including suitable programming in the at least one controller 34 associated with each automated banking machine. Thus for example the controller may be programmed to produce the encrypted data directly and to send this encrypted data either through the associated host or through other connected networks to the at least one remote computer which identifies the possible occurrences of fraudulent transactions on a stolen account. In addition as previously mentioned, in other exemplary systems, rather than having a common approach to producing encrypted data where the same data corresponds to a common account, other approaches may be taken so as to send other data which can be resolved through appropriate programmed steps executed by the at least one remote computer 58 to identify that the encrypted data sent from different sources corresponds to a common account. This may be done, for example, by programming of the automated banking machines, the host computer and the servers in different ways to produce the encrypted data, and by providing programming that enables the at least one remote computer to identify that the different types of encrypted data correspond to one particular account. Further these approaches are useful in the exemplary embodiment because with the remote computer being incapable of determining the actual financial account data from the encrypted data, the financial account data remains secure. This is true even if the encrypted data is transmitted through an insecure network such as the Internet. Of course it should be understood that these approaches are exemplary and in other embodiments, other approaches may be used.

Figure 4:
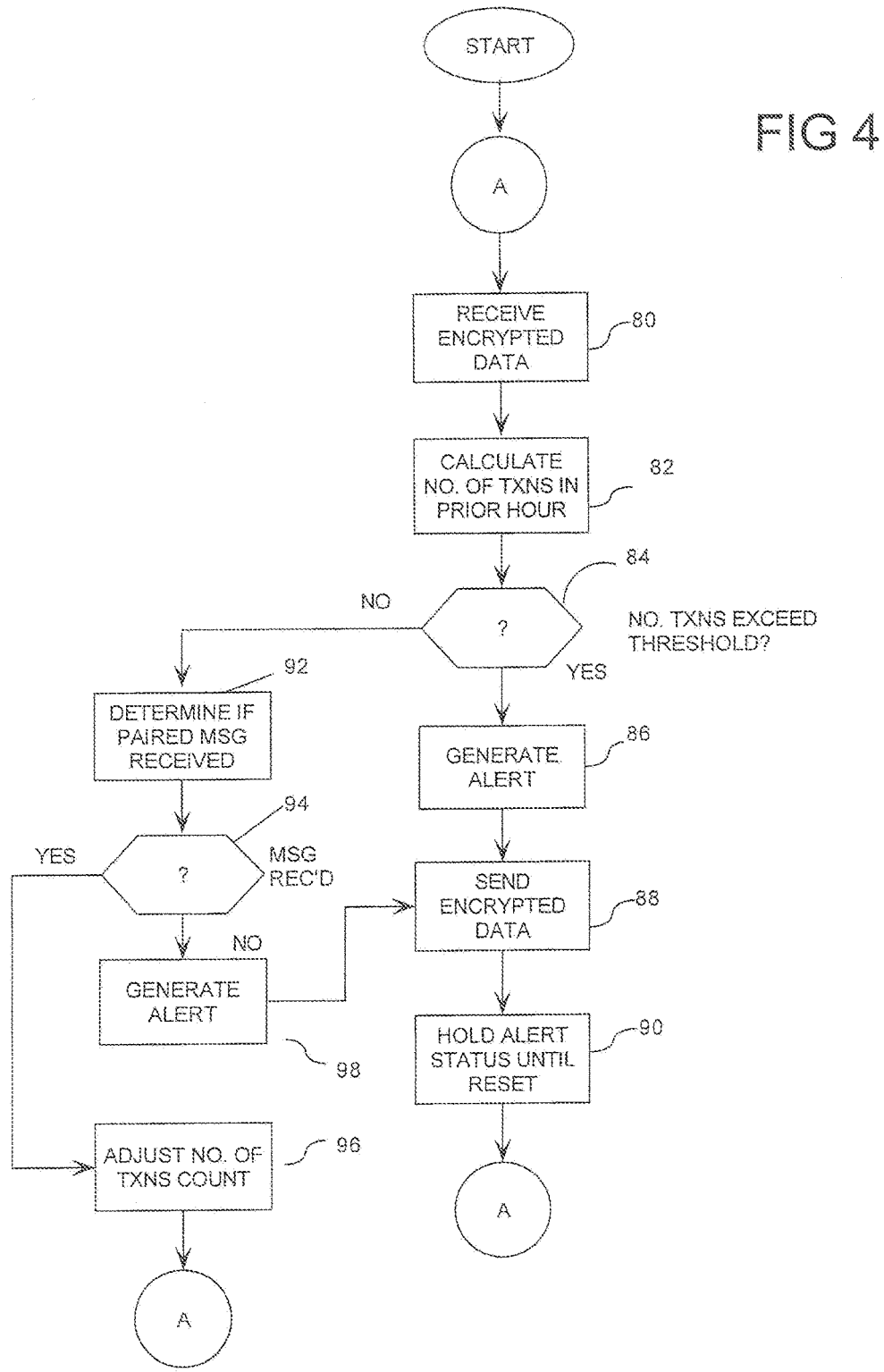
FIG. 4 is an alternative schematic view of steps executed by at least one computer in connection with an automated banking machine system of an exemplary arrangement.

FIG. 4 shows an alternative arrangement in which one or more computers 58 may be operated to identify unauthorized transactions, as well as circumstances where account data may be stolen. In this exemplary arrangement transactions are carried out on the account using a mobile wireless device such as a smart phone 78 represented schematically in FIG. 1. It should be understood that in exemplary arrangements a wireless device may correspond to other types of devices such as tablet computers or wearable computers which are usable by consumers to conduct transactions at an automated banking machine. Alternatively the wireless device may correspond to an article associated with a user such as a user's vehicle which incorporates one or more computers within the circuitry thereof.

In the exemplary arrangement the mobile wireless device is operative to cause data corresponding to the financial account to be sent to the automated banking machine at which the user wishes to conduct a transaction. This may be done, for example, by the mobile wireless device sending data from the device wirelessly through the input device 32 of the automated banking machine. The mobile device may be operative to cause the automated banking machine to receive data that is usable to identify a financial account. This may be done, for example, in some arrangements by the mobile device sending the automated banking machine data which corresponds to an account number directly. Alternatively in some arrangements the mobile wireless device may cause communications with other systems which then cause the automated banking machine to receive data which corresponds to or is usable to resolve the account number. For example in some exemplary arrangements systems may include features like those described in the following U.S. Patents which are incorporated herein by reference in their entirety: U.S. Pat. Nos. 8,281,989; 8,376,221; 8,474,707; 8,052,048; 7,216,800; 7,201,313; and 8,480,307. Of course these approaches are exemplary and in other arrangements other approaches may be used.

In the exemplary arrangement at least one processor included in circuitry of the mobile wireless device 78 may operate in accordance with its programming to cause encrypted data that corresponds to the financial account on which a transaction is to be conducted to be sent to the at least one remote computer. This may be done for example through communication via wireless networks 64. Further as the automated banking machine host computer or server which receives the requested transaction also sends encrypted data that corresponds to the account, this enables the at least one remote computer to identify a common pair of communications having encrypted data that are both received close in time for each authorized transaction. The at least one remote computer 58 is programmed to identify circumstances where both instances of the encrypted data for the given transaction have not been received and to identify such circumstances as a possible situation where a fraudulent transaction may be occurring. The logic associated with such a remote computer that identifies such circumstances is represented in FIG. 4.

In this exemplary arrangement the at least one remote computer 58 receives the encrypted data associated with the account either from the mobile wireless device, server, host or automated banking machine as represented in step 80. As in the prior example the at least one remote computer that operates to calculate the number of transactions indicated as attempted on that account within a given time period. This is represented by a step 82. If the number of transactions is determined to have exceeded the threshold, as represented in a step 84, the at least one computer executes steps similar to those in the prior example. These include generating an alert, sending the encrypted data to the remote systems and holding the alert status until it is reset. This is represented in steps 86, 88 and 90 respectively.

In this exemplary arrangement, in situations where the at least one remote computer is expecting to receive two paired messages in closely spaced time relation in order to indicate that a transaction is authorized, the at least one computer operates in accordance with its programming to determine if the two paired messages associated with the one transaction were received. This is accomplished by the at least one remote computer comparing the messages received with the encrypted data that corresponds to the particular account and the timing associated with the receipt thereof. This is represented in a step 92. A determination is made in a step 94 concerning whether the two paired messages for the common transaction were received. If the two paired messages for the single transaction were received close in time as would be normally expected, then the at least one remote computer 58 operates in accordance with its programming to not indicate that there is a problem. In the exemplary arrangement the at least one remote computer operates in accordance with its programming to adjust the transaction count of transactions on the account to accommodate that two messages are received for each transaction. This is represented in a step 96. Thereafter the at least one remote computer operates to continue to monitor for any potentially problematic conditions.

However, if in the step 94 it is determined that paired messages from the mobile wireless device and from the automated banking machine, host computer or server computer receiving the transaction request were not both received, the computer operates in accordance with its programming to identify an abnormal condition and to generate an alert. This is represented in a step 98. As can be appreciated, the absence of both messages of the expected pair may represent a circumstance where a transaction has been attempted by a criminal or unauthorized person who is not using the authorized mobile wireless device, but is instead providing the account data from an unauthorized source such as a counterfeit card or other fraudulent input device. Alternatively the condition may represent the circumstance where criminals have set up a fraudulent terminal to receive transaction data so as to capture the data for purposes of conducting fraudulent transactions. In either case these circumstances represent a suspect condition.

In the exemplary arrangement the computer operates in accordance with its programming to identify that there is an abnormal condition associated with the account as appropriate to the other computers in the systems. This will enable such computers to identify further attempted transactions on the account and to deny them in accordance with their programming. Further the at least one computer operates in accordance with its programming to hold the alert status associated with the account until it is reset.

Of course it should be understood that these approaches are exemplary and in other embodiments, other additional steps and arrangements may be taken similar to those described herein for purposes of identifying suspect transactions and for denying such transactions and reporting criminal activity.

Figure 5:
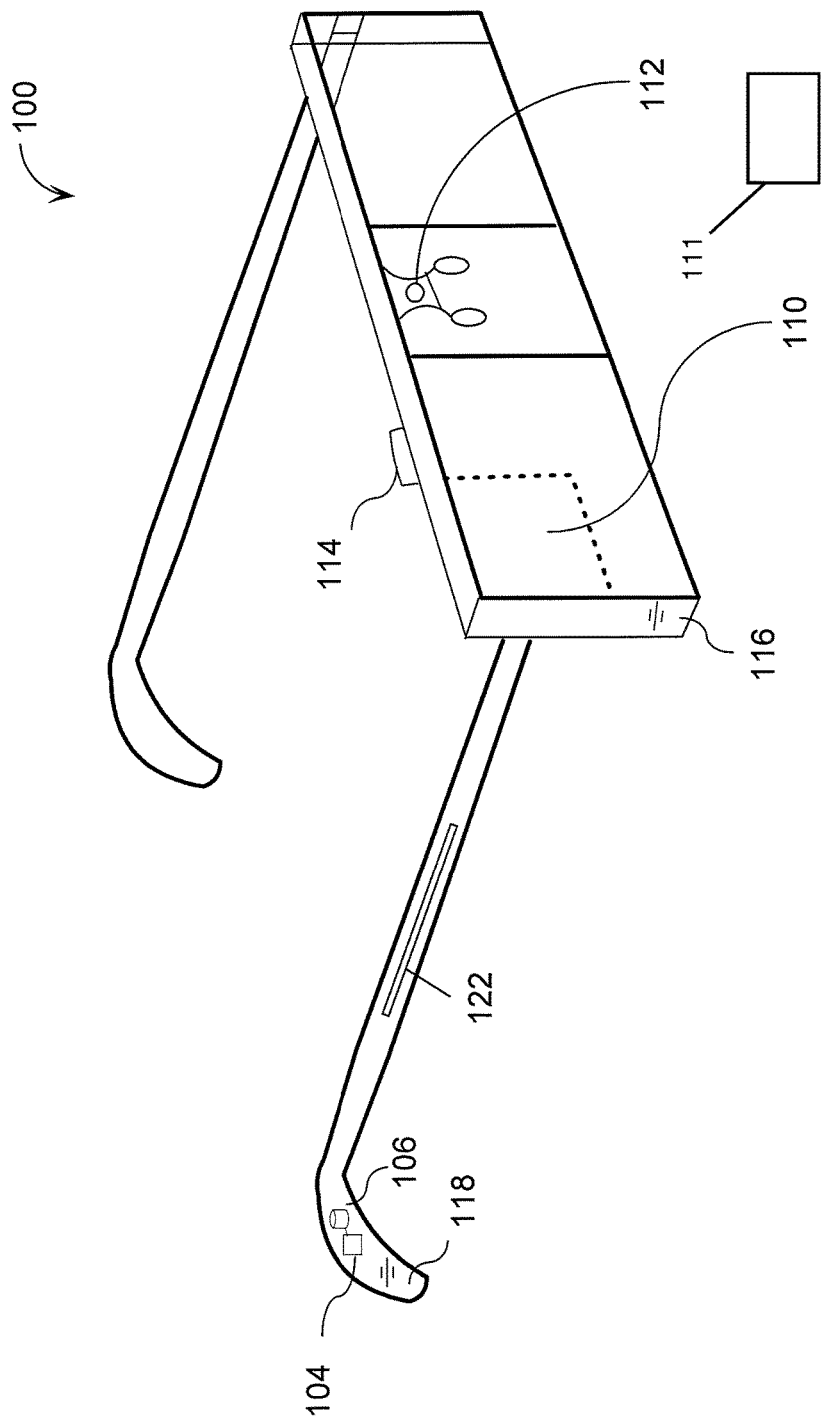
FIG. 5 is an isometric view of an exemplary user wearable mobile wireless device.

FIG. 5 shows an exemplary arrangement of a mobile wireless device generally indicated 100 that may be used in connection with an automated banking machine or otherwise for purposes of carrying out financial transactions. The exemplary device 100 is configured as wearable glasses. However, it should be understood that in other arrangements other configurations of devices may be used. For example, configurations similar to that of a wrist watch, a medallion or a hat or other item of clothing may be used. The exemplary embodiment of device 100 includes at least one circuit which is operative to control the operation of devices that are included as part of the mobile wireless device. The at least one circuit designated 102 in FIG. 6 includes a processor 104 and an associated data store 106.

The exemplary arrangement further includes a source of electrical power such as a battery 108. The exemplary arrangement further includes a generally transparent display 110, an outward facing camera 112 and an inward facing camera 114. The exemplary embodiment further includes a microphone 116 and a speaker 118. The exemplary embodiment further includes a wireless transmitter 120. The wireless transmitter 120 is suitable for transmitting wireless signals between the mobile wireless device 100 and other devices. The wireless transmitter 120 may include a short range wireless transmitter such as a short range RF transceiver or a Bluetooth™ transceiver. Alternatively the wireless transmitter may include an infrared transceiver. Alternatively the wireless transmitter may include a transceiver suitable for communication via a cellular telephone network or other wireless network. Further in some arrangements of the mobile wireless device the apparatus may include multiple types of wireless transceivers depending on the nature of the communications to be carried out through operation of the device.

Figure 6:
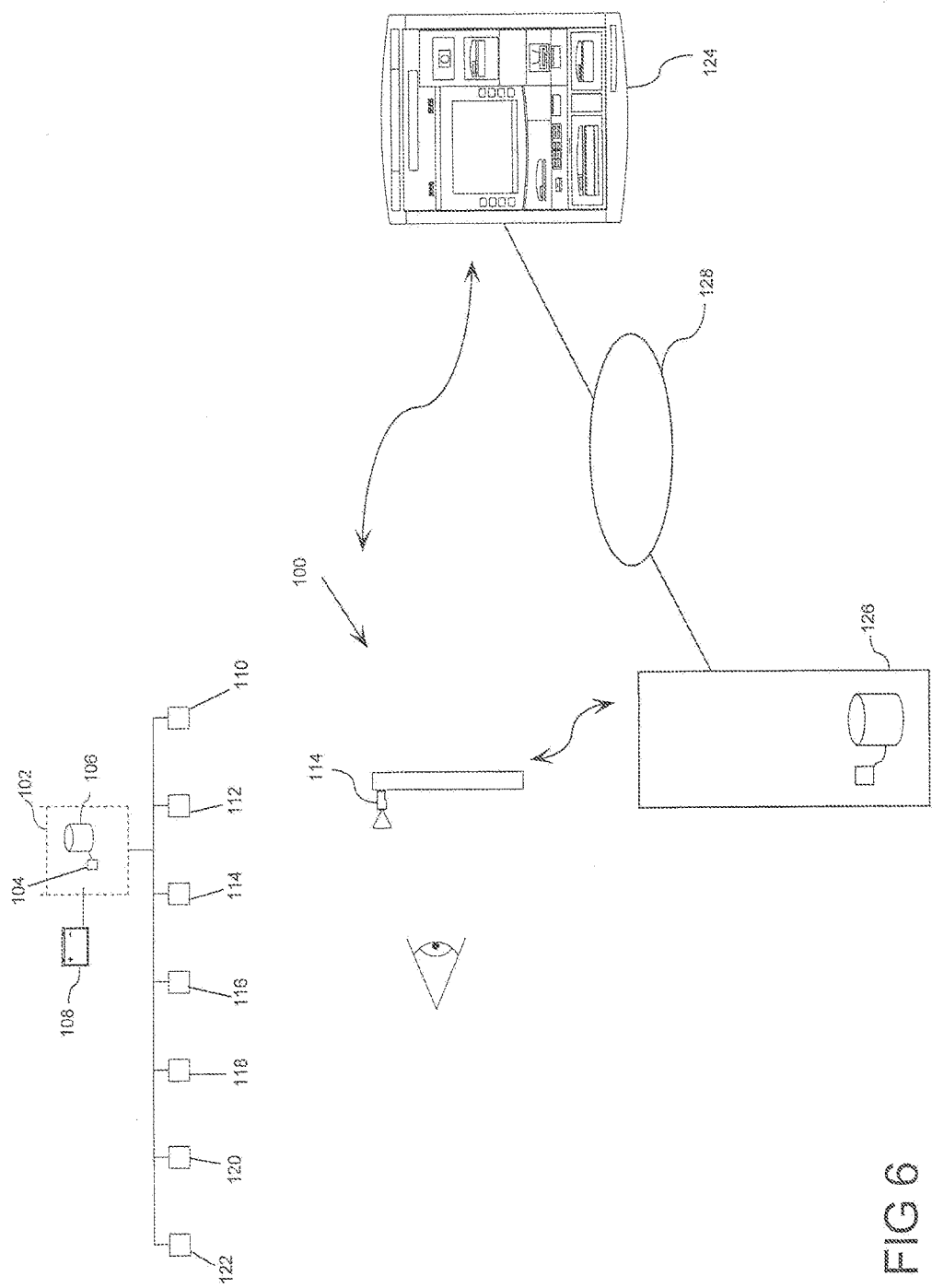
FIG. 6 is a schematic view showing components of the wearable mobile wireless device operating in connection with components of an automated banking machine system.

As represented in FIG. 6, exemplary embodiments of the mobile wireless device may operate to carry out financial transfers. This may be done through communication with an automated banking machine in one of the ways described in the incorporated disclosures. In other arrangements the mobile wireless device may cause financial transfers through communications via a cellular network, a local wireless network or other local or wide area network. The exemplary mobile wireless device is operative to include data in its data store that is usable to identify a financial account. In the exemplary arrangement the data store of the mobile wireless device also includes data that corresponds to a user biometric feature. In some exemplary arrangements this may include programming in the data store that includes data that corresponds to the topography of an authorized user's iris topography of one or both of the user's eyes. The user's iris topography uniquely identifies the authorized user and can be captured through the use of at least one inward facing camera 114. Further in some exemplary arrangements the mobile device may include multiple inward facing cameras or other cameras that can capture iris topography of both irises of the authorized user. In addition or in the alternative other mobile devices may include capabilities for identifying a user's facial topography, retina features and/or other biometric features that can be utilized to identify the user.

Responsive to the inward facing camera or cameras 114 capturing data corresponding to the user's iris topography or other identifying data, the circuitry 102 may operate in accordance with its programming to verify that the mobile device is being operated by the authorized user. This may be done by comparing captured electronic image data to stored data to determine whether there is correspondence or another predetermined relationship which indicates the user is an authorized user. Responsive to such verification determination the authorized user may then provide instructions to the mobile device in connection with carrying out a financial transaction and the mobile device will operate in accordance with its programming to execute instructions responsive to such commands. This may be accomplished in some exemplary arrangements by the user providing spoken commands that are received by the microphone 116 and determined as transaction related inputs through operation of the control circuit 102. Alternatively the user may be presented with menu options or similar options through the display 110, which options the user may select. Selections may be made and input in some embodiments by providing spoken commands that correspond to the options. Alternatively the user may provide selected inputs which enable selecting transaction options output on the display through moving a finger along a tactile sensing bar or other similar input device 122. In still other exemplary arrangements the user may provide inputs through eye movements or line of sight determinations which are detected by the one or more inward facing cameras 114. This may be done for example by utilizing features such as those described in U.S. Pat. Nos. 8,220,706 and/or 8,883,008 the disclosures of which are incorporated herein by reference in their entirety. For example in some exemplary arrangements the circuitry connected with the at least one camera 114 may determine a location where a user eye is looking on the display 10. By determining what particular transaction selections or options the user is looking at, the control circuitry may determine user provided inputs. For example in some instances the user may look at a particular selection being provided on the display and designate that selection by blinking one eye or both eyes. When this is done the control circuitry may then operate to provide additional outputs and/or messages that enable carrying out the transaction selected by the user.

As represented in FIG. 6, the mobile wireless device 100 may be used for example to send data associated with a user desired transaction to an automated banking machine 124. Such data may include data such as card data that is usable to identify a user's account. Such data may be stored in the at least one data store 106 and then transmitted wirelessly to the machine. Further in some arrangements the user may select through the mobile wireless device an account, a transaction type and/or an amount associated with a transaction that they wish to conduct. Data corresponding to these items of information may be included in messages transmitted to the automated banking machine and received through a wireless portal on the machine. This may be done in any one of several ways that are described in the incorporated disclosures or in another suitable manner.

Alternatively in some arrangements the mobile wireless device 100 may communicate data to a server 126 that is remote from the automated banking machine. The server 126 may utilize the data sent from the mobile wireless device to resolve transaction data that is needed by the automated banking machine to carry out the transaction. This may include, for example, account data or other data such as amount data, PIN data or other data that is needed by the machine 124 for purposes of carrying out the transaction. This data may be transmitted from the server 126 to the machine through one or more networks 128. This approach may be utilized, for example, when the mobile device does not include data that directly corresponds to the account information, but rather pseudo data that may be utilized by one or more remote servers to determine the actual account information. Thus for example server 126 may include in its associated data store, data that associates the pseudo data that is provided from the mobile wireless device with the actual account data. The actual account data may then be sent in an encrypted and secure manner to the automated banking machine. This approach may avoid the need, for example, for the mobile wireless device to have included in its data store actual account number data.

Also in other alternative arrangements the mobile wireless device may use its outward facing camera 112 to capture data that is output on the display or other output device of the automated banking machine. Such output data may be used in the manner of the incorporated disclosures to identify a particular machine at which a transaction is to be conducted. This identifying data or data based thereon may then be transmitted to the remote server so as to enable user operation of the automated banking machine. Alternatively or in addition data captured through the outward facing camera of the mobile device may correspond for values, functions and/or instructions that may be utilized for purposes of encrypting account data that is stored in a data store of the mobile wireless device. For example, bar codes such as QR codes output through a banking machine display may provide values or instructions utilized for purposes of encryption of account data. Such encrypted account data may then be sent to either the automated banking machine and/or the remote server for purposes of securing the account data to reduce the risk that it can be intercepted during the transaction. This may be done a number of different ways including those described in the incorporated disclosures as well as in other suitable ways depending on the particular operation of the system.

In this manner a user may accomplish transaction steps through the wearable mobile wireless device or other user device for purposes of carrying out financial transfers. Further it should be understood that although in the exemplary arrangement the mobile wireless device is used in connection with an automated banking machine to accomplish transactions, in other arrangements other devices and systems may be utilized and messages from the mobile wireless device may accomplish financial transfers, account balance checking, bill payment, check capture or other desired transaction operations. For example in some exemplary embodiments the mobile wireless device may utilize an outward facing camera for purposes of capturing an image of a check. The user may provide instructions either verbally or through input devices to capture the image of the check and then cause the check to be deposited in the user's account. This may be done, for example, in the manner shown in U.S. Pat. Nos. 8,418,916; 8,286,867; and/or 8,104,676 the disclosures of each of which are incorporated herein by reference in their entirety.

Further in other exemplary embodiments data corresponding to electronic tickets or other items representative of value may be loaded into the memory of the mobile device. This may be done, for example, through capturing images thereof through the outward facing camera or otherwise through transmission wirelessly to the device. The mobile wireless device may thereafter be utilized to transmit data which may be utilized for purposes of redeeming or utilizing the items of value. This may be done, for example, through approaches described in U.S. Pat. No. 8,387,864 the disclosure of which is incorporated herein by reference in its entirety. Of course these approaches are exemplary, and in other embodiments other approaches may be used.

Further other exemplary arrangements of the mobile wireless device may be useful to accomplish other transaction functions. For example in some exemplary arrangements the circuitry associated with the mobile device may be programmed to identify genuine items of value such as currency bills. This may include, for example, executable program steps that are usable to verify that visible and/or other sensor perceivable authentication features are present in a particular currency bill. Thus, for example, a user may operate the mobile wireless device to capture one or more images of a currency bill through operation of the outward facing camera 112. This may be done, for example, by the programmed instructions associated with the mobile device instructing a user through audible prompts or the visual outputs through display 110 to look at certain features on a currency bill. The control circuitry of the mobile wireless device may operate to utilize the eye tracking capability to monitor the eye or eyes of a user to direct or analyze areas in the field of view the outward facing camera at which the user is looking to a series of features that may identify a currency bill as genuine. In this way the front and/or back of a currency bill may be analyzed to verify that indicia or other visible features indicative of genuineness of the bill are present. In addition alternative exemplary arrangements may include infrared, ultraviolet and/or spaced cameras for purposes of capturing images of authenticity features. Alternatively a user may be prompted to take certain steps with one or more separate devices. This can include illuminating certain areas with radiation at certain frequencies, testing for magnetic or other sensed properties. The camera may capture features or indications of properties or characteristics that are indicative of whether notes are genuine. This approach may be utilized in some exemplary arrangements to enable a user to identify counterfeit or suspect notes that a user receives in a transaction environment and to decline such notes as may appear to be suspect. Further in some example arrangements the wireless communication capability of the mobile wireless device may enable the user to operate the mobile device to analyze, verify or record data in one or more data stores that correspond to the genuine or suspect status of currency bills that are analyzed through operation of the mobile device. Thus in this manner the user can avoid accepting counterfeit currency bills that may be attempted to be passed to the user.

Alternatively or in addition the mobile wireless device may be operative to verify the authenticity of other items or documents. This may include, for example, the capability to identify the genuineness of a credit or debit card through analysis of the visual or other non-contact sensor detectable features included thereon. Thus for example a merchant who wishes to accept a credit or debit card may utilize the mobile wireless device to analyze the features that are on the card including holograms, security codes, or other features that identify the card as genuine. Further in some arrangements such cards or other items may include wireless transmitters or other similar items, such as RFID tags that can be utilized to output signals which can indicate that the card or other item is genuine. The mobile device may include appropriate sensors to capture and analyze such signals and properties and may operate one or circuits that include processors to determine of the card or other item is genuine.

Further in some exemplary embodiments the mobile wireless device can capture image data from the card or other record including for example account number data, verification codes, name data or other items that are usable to carry out a financial transaction. In such arrangements, for example, an operator of the mobile wireless device may utilize the mobile wireless device to obtain the data from a card that is necessary to identify the particular account with which the card is associated and also to verify the genuineness of the card. In this manner by providing instructions to the mobile wireless device, the operator of the device is enabled to accept payments or otherwise accomplish functions that involve a transfer to or from the account associated with the particular card. Such an approach may enable the operator of the mobile wireless device to accomplish the acceptance of credit card and/or debit card payments without a need to have a separate terminal that operates to receive the card, read data from a stripe or computer chip on the card, or otherwise to identify the particular card as genuine and authorized to conduct the transaction.

In still other exemplary arrangements, the mobile device 100 may be utilized to identify features which are indicative of authenticity on articles such as event tickets, gaming tickets, lottery tickets, coupons, vouchers, scrip or other items. In this manner the mobile wireless device may be programmed to utilize image data and/or other data which can be visually or wirelessly read by the device, or with the aid of another device, to determine the genuineness of such articles. Of course these approaches are exemplary and in other embodiments other approaches may be used.

In still other arrangements the mobile device 100 may be utilized to provide useful features in connection with conducting transactions in transaction environments where cash or other items of value are accepted by merchants or similar entities. For example in some establishments, merchants may prefer to receive cash payments for the goods and services they provide. Cash payments have the advantages that they avoid the risks and costs that may be associated with taking payments by either credit or debit cards. Some establishments even provide automated banking machines that dispense cash within their establishment so that users can readily obtain cash for purposes of making purchases. However, such automated banking machines that dispense cash in merchant establishments may commonly charge a fee for purposes of conducting the transaction. This fee may be several dollars in some cases.

In order to facilitate the use of cash in some transaction environments, the establishment may be able to track the serial numbers of currency bills that are dispensed from an automated banking machine to patrons within the establishment. This may be done using features like those described in U.S. Pat. No. 8,474,708, the disclosure of which is incorporated herein by reference in its entirety. In such arrangements the serial numbers associated with dispensed bills may be stored in a data store associated with one or more computer devices that are accessible by the wearable computer devices worn by employees within the establishment. Such mobile wearable computer devices may utilize features like those previously described to evaluate currency bills for genuineness and to also determine the serial numbers thereon. The wearable computer device 100 may communicate the serial numbers from received bills 111 (shown schematically in FIG. 5) to determine if the bills received correspond to those dispensed by the automated banking machine in the establishment. This may be done, for example, through the use of cameras 112 on a mobile wireless device 100 capturing the serial number data and resolving the data in a manner that can be transmitted wirelessly to the computer which can access the serial number data corresponding to bills dispensed from the banking machine. In cases where a serial number received by an employee is one that was dispensed from the machine, the merchant may offer a credit or a discount to the purchaser. In this way the purchaser is compensated for spending the money that they obtained through use of the machine and paying the surcharge to obtain the cash. Such an approach may be very useful in providing an incentive for individuals to spend the cash that they obtain from the banking machine in the establishment where the machine is located. In addition it may enable the proprietor to evaluate the value of having the machine in terms of how much of the cash that is dispensed therefrom is actually spent by patrons within their establishment. This may be done through programmed instructions associated with one or more computers that evaluate the amounts corresponding to purchases by patrons in the establishment that are based on bills that were dispensed from the machine. Further in the exemplary arrangement the computer data concerning serial numbers of bills that are dispensed from the machine are only held for a limited set period of time. This may correspond in some cases to a one day period, as it would be expected that patrons would likely spend the cash that they receive from the automated banking machine during the same visit to the establishment in which the cash was received. Of course in some establishments the set period may be longer or shorter. After the set period of time, the data concerning the serial numbers of bills dispensed would no longer be stored. This avoids the need for creating a large database to hold serial number data associated with dispensed bills. Of course these approaches are exemplary and in other arrangements other approaches may be used.

In some exemplary transaction environments, employees of a particular merchant may have the wearable computer devices 100 provided by the establishment. It may be a requirement of the employment that the employee utilize the wearable computer for business activities during their work hours. In this way, the available functions of the devices can be available at all times which the employee is on duty. In addition in some arrangements the employer may require that each employee store their wearable mobile wireless device 100 in a particular location when it is not in use, such as during off hours when the establishment is closed. In some exemplary arrangements a mounting shelf or stand may be provided onto which the employee may place the wearable wireless mobile device when the employee's shift has ended. The placement of the mobile devices when they are not in use may provide for additional uses of the devices during off hours.

As can be appreciated, the cameras 112, 114 which are utilized on the wearable mobile wireless devices 100 may serve as surveillance cameras during times that the establishment is not open. Such surveillance cameras may be monitored from local or remote monitoring stations so that any intrusions or abnormal conditions can be detected within the establishment. Similarly, audio receiving devices such as microphone 116 included on the wearable computer may be monitored during off hours for purposes of determining abnormal noises which may be indicative of a break-in, machinery malfunction or other problem within the establishment. By having numerous mobile devices positioned in various areas of the establishment during off hours, it may be possible for a monitoring system to observe more areas from more different perspectives than would be possible with stationary security cameras. In addition, other detection features of mobile devices 100 such as audible sounds or infrared signals or other things that the wearable mobile devices are capable of sensing, may be utilized in monitoring activities so that such properties may be detected to uncover abnormal or problematic conditions. Of course the capabilities of the wearable mobile wireless devices will determine the capabilities that can be achieved through such arrangements and numerous variations to achieve effective monitoring may be utilized in various arrangements. In some arrangements, features similar to those described in U.S. Pat. No. 8,302,856 which is incorporated herein by reference in its entirety, may be utilized.

Figure 7:
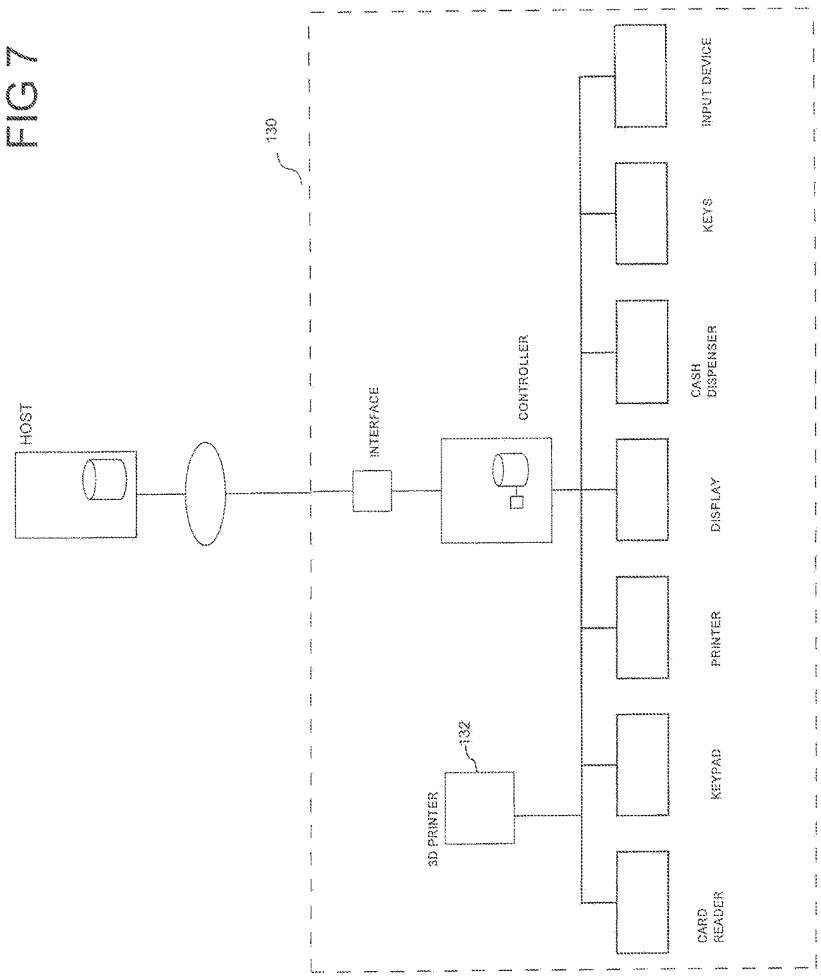
FIG. 7 is a schematic view of components of an alternative exemplary automated banking machine that has the capability of producing or configuring an article for a user.

FIG. 7 shows another exemplary automated banking machine with an alternative arrangement generally indicated 130. Automated banking machine 130 may generally operate in a manner similar to automated banking machine 12 previously described and may include similar components. This alternative embodiment also includes an item producing device generally indicated 132. In the exemplary arrangement the item producing device 132 includes a 3D printer. The 3D printer is utilized to produce items that are dispensed from or otherwise made available by the automated banking machine to a user.

In an exemplary arrangement a 3D printer or other type of material printer is utilized to produce an item that is representative of and is redeemable for value. Specifically in some exemplary arrangements the printer is operative to print patterns of conductive material that comprise RFID tags on a substrate to produce a token. The RFID tags are usable to produce signals corresponding to values that identify the token as genuine and that are associated with or representative of the value for which the token is redeemable.

For example in some exemplary embodiments a user may operate the automated banking machine in a manner similar to that previously described in connection with a cash dispensing transaction. However, in an exemplary alternative arrangement the user may elect through inputs to the machine, to receive a token corresponding to a selected value rather than cash. This would be done, for example, where a user wishes to receive a token that is redeemable for a particular type of merchandise or services available from a particular identified retailer. For example in some arrangements the retailer may offer an additional bonus in terms of goods or services value above the amount that the user pays for the particular token in order to provide an incentive for the user to acquire the merchant's goods or services. Of course this arrangement is one of many that may be utilized in connection with the described features.

Figure 8:
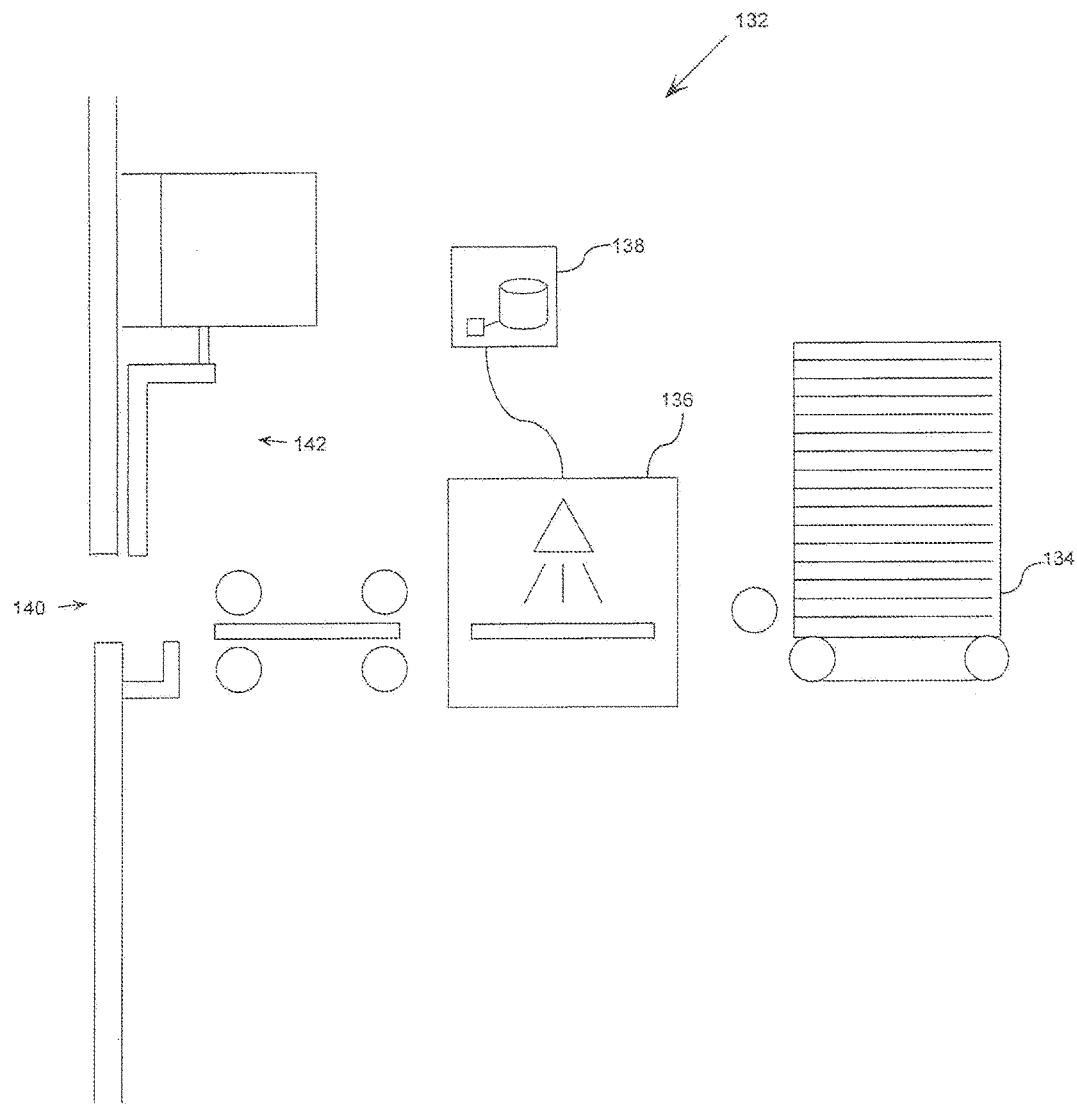
FIG. 8 is a schematic view of a 3D printer operated in connection with articles dispensed from an exemplary automated banking machine.
Figure 9:
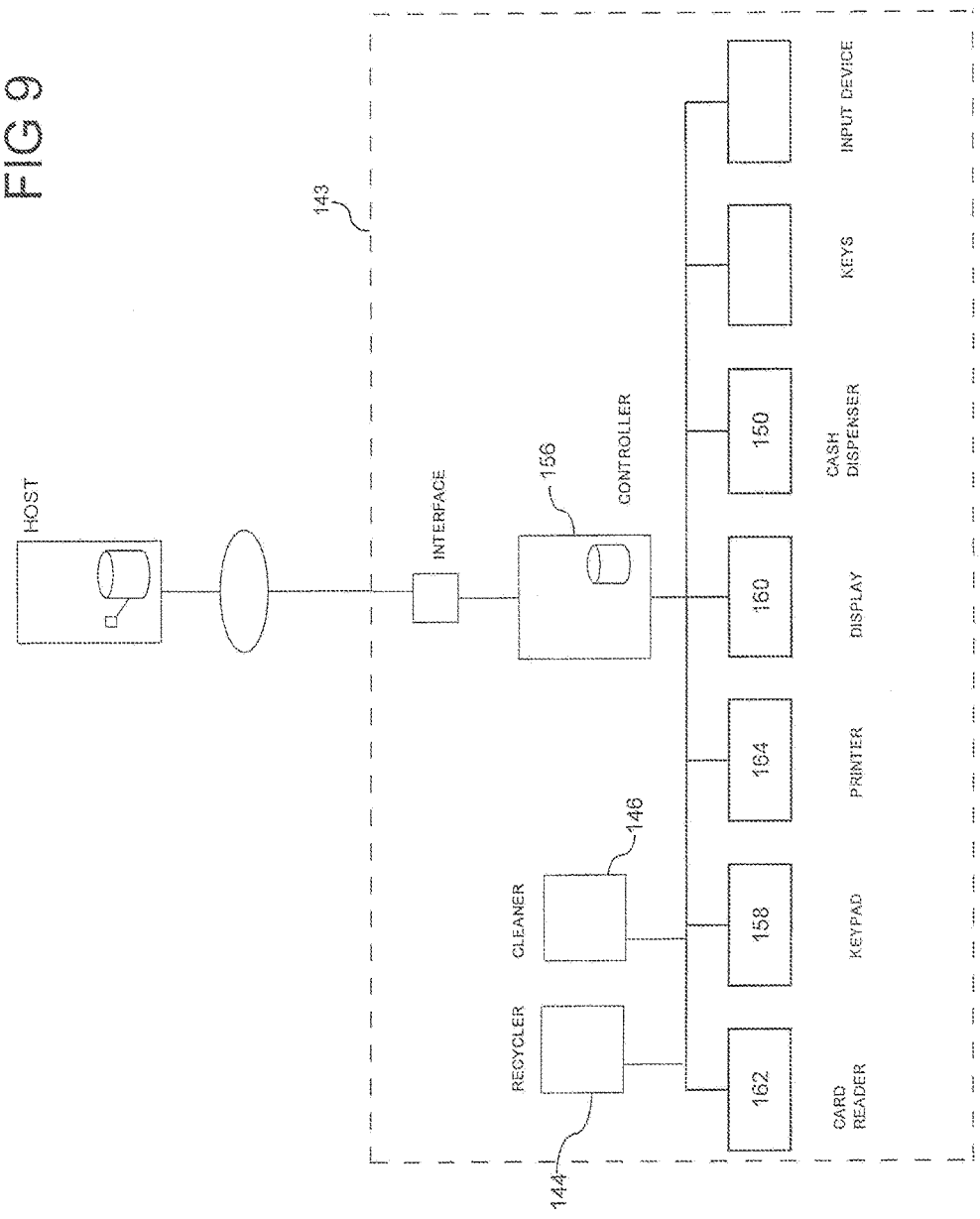
FIG. 9 is a schematic view of an alternative arrangement of an automated banking machine that provides the capability for disinfecting items dispensed from the machine.

In such arrangement the printer may operate as represented in FIG. 8 to produce a token that includes indicia that can be securely redeemed for value by the particular merchant. In this arrangement the printer 132 includes a mechanism that operates to receive a piece of token substrate material from a magazine or similar storage area generally indicated 134. The single item of substrate that is removed from the storage area is then printed upon by applying one or more patterns of metallic conductive material thereon in a printing chamber 136. The printing chamber includes a printing head that deposits the metallic material such as silver or copper inks in patterns that correspond to one or more RFID tags. This is accomplished through control provided by circuit 138. Circuit 138 includes one or more processors and one or more data stores with programmed instructions that are usable to determine the value or values corresponding to the desired tags and to produce the patterns corresponding to the RFID tags that are produced on the token.

It should be understood that in the exemplary arrangement one or more RFID tags that are produced on the substrate correspond to values that are known by the controller of the automated banking machine and that are communicated to one or more remote servers. This enables the token that is produced through operation of the printer to be identified as genuine or otherwise acceptable by RFID tag readers or other items positioned at the locations where the token may be redeemed for goods or services of the merchant. Further as can be appreciated, the RFID tags that are included on the token produced may include security features, encryption features, verification features, redemption indicating features or other items and features that are usable to prevent counterfeiting and assure that the token presented is usable and genuine.

Once the exemplary token has been produced by the printer, it is moved through operation of a suitable conveying mechanism through an opening 140 in the automated banking machine so that the token may be received by a user. As can be appreciated, the opening may be controlled by one or more suitable gate mechanisms 142 or other mechanisms to help assure that access to the interior of the machine and the 3D printer from outside the machine is prevented.

Of course it should be understood that production of tokens corresponding to value is merely exemplary of the types of items that may be produced through operation of an automated banking machine including one or more 3D printers or other printer types. For example in some exemplary arrangements the automated banking machine may be usable to produce plastic sheet materials. Such plastic sheet materials may include embedded metallic or non-metallic materials which may be usable to identify the sheets as genuine and also to indicate the value associated therewith. In addition visible and non-visible elements may also be produced within or on the sheets so as to provide a visual appearance that may indicate to a user the nature and/or value of the particular item. Such items may commonly include items such as scrip, coupons, tickets or other items that are representative of or are redeemable for value.

Further in some exemplary arrangements such items may include embedded items that are included during their production in the machine. This may include, for example, batteries, sensors, output devices, input devices or other suitable items that may be either pre-produced and embedded in the appropriate locations within the item when it is produced, or alternatively produced by multiple different types of 3D printers and/or other printers or devices included in the machine. For example and without limitation, some arrangements may include the capability of the automated banking machine to produce a token, card or similar article that in itself can be operated as a transaction terminal that can be operated by a user to carry out certain types of financial transactions. This may be accomplished by producing an item that includes a wireless transceiver, input and output devices, contact or non-contact connectors and other things necessary to accomplish financial transfers through communication. Such a produced item for example may include the capability of transferring funds in an amount up to the associated value that the user selected in connection with the transaction that resulted in production of the item. Of course this approach is exemplary and many different types of items may be produced utilizing the principles discussed herein.

In some exemplary arrangements the automated banking machine may provide tokens, cards or other articles that include circuits including microprocessors and other electronic components. In some exemplary arrangements the microprocessors and other circuitry may include organic microprocessors and other electronic components. Such components may be produced for example in some exemplary arrangements by depositing thin films of alternating layers of organic material (for example, pentacene and insulators) and metallic materials such as conductive inks for interconnections. Such layers may be deposited onto a substrate such as a plastic material to produce microprocessors and other circuit components that can execute instructions and other circuit component functions, and to provide outputs via card contacts, RF transceivers or other devices that are usable in connection with providing transaction data or other information used for purposes of transactions.

In some exemplary arrangements such technology may be utilized for purposes of providing microprocessors on or in transaction cards that can be used to provide verification of the genuineness of the card. This may include, for example, producing microprocessor circuitry from organic material that carries out algorithmic functions that identify the particular card as genuine. These algorithmic functions may be those developed by certain industry standard setting organizations such as EMV. Using such approaches data supplied as signals to circuitry on a card produces a result which indicates that the card is the genuine card and not a counterfeit. Such techniques are particularly useful in connection with magnetic stripe cards for which providing the separate circuitry including processor capability is usable to generate verification values that provide an indication that the card is not counterfeit. Thus for example in an exemplary arrangement, data from a magnetic stripe on a card may be read by a card reader to provide account number and other data related to an account on which a transaction can be conducted. In addition, certain inputs to the microprocessor circuitry can be used by the circuitry to produce one or more results. Such one or more output results may be communicated and/or compared or otherwise used for purposes of comparison to data that indicates the genuineness of the card. Different types of algorithms may be used for purposes of the programming of the microprocessors so as to utilize different input values or other parameters to produce results which can be verified as appropriate and corresponding to a genuine card. As can be appreciated, various forms of encryption and decryption and other security functions may also be included in such circuitry that includes the microprocessor.

In some exemplary arrangements an automated banking machine may be operated to apply microprocessor including circuits directly to an area of an existing card. Such microprocessor based circuitry may then be utilized thereafter to verify the genuineness of that particular card. In some exemplary arrangements the microprocessor based circuitry may communicate via direct contact with conductive contacts that engage the circuitry on the card that is applied through printing or other techniques. In other arrangements the applied microprocessor circuit on the card may communicate in a wireless manner via radio signals or other signals similar to RFID tags previously discussed.

In some exemplary arrangements the automated banking machine may operate to take an existing card and with the permission of the user, apply the appropriate circuitry thereto to add verification capabilities that are usable in the future to verify that the card is the genuine card. In other arrangements, the automated banking machine may operate to build for the user a new card or other article that includes appropriate circuitry to verify that the card or article is genuine. This may be done in some arrangements, for example, by having a stored group of cards or other items which serve as the substrate or base part for the articles to be produced. The circuits including microprocessors and other components is then applied to the substrate or base part to produce an article that can be used to provide transaction data such as account number, user name and other information, and then also provides outputs that can be used to verify that the item is genuine.

In still other arrangements, 3D printer technology may be utilized to produce an item without the use of a starting substrate or base part. In some exemplary cases the 3D printer may be operated to produce a card shaped article that includes therein circuitry and other components that enable the use of the article as a credit card or a debit card. This may include, for example, circuits including microprocessors or other devices produced via substance deposition techniques in appropriate configurations. Such circuits are operative to store and securely deliver account data, verification data and other data that can be utilized to carry out transactions. For example card-like articles that wirelessly communicate with automated banking machine card readers can provide account data to be used to carry out purchase or banking transactions through connected terminal devices.

In still other exemplary arrangements, articles may be produced that include appropriate circuits that communicate transaction data and/or other data with other devices so that a user can obtain goods or services through use of the particular item. For example in some exemplary arrangements a 3D printer may be utilized to produce a wearable article for a user that provides account data and other transaction data to systems that communicate with the device. This enables a user to make purchases, transfer funds and carry out other functions without need for interaction with dedicated financial transaction terminals. For example in a transaction environment where a user makes purchases, the user may be provided with a wrist band or pendant that the user can wear while in the area where transactions are enabled to be conducted. Articles that a user can purchase are labeled with RFID tags or other indicators of a price associated therewith. By transporting the items from a location where they can be viewed and are positioned for sale within the establishment, to another area of the establishment such as an area adjacent to the exit, wireless transceivers determine the particular articles that the user is carrying and the user's account data by communication with the wearable article worn by the user in the transaction environment. The user's account may then be automatically charged for the items that are taken.

In alternative exemplary arrangements that article may be produced via 3D printing or other techniques previously discussed, and provided to a user in an area where the user may receive and be charged for services. Such areas may include for example, theme parks, movie theaters or other areas where a user is charged based on where they travel within the establishment. The article provided to the user may wirelessly communicate with sensors located in different areas so that the user's account is automatically charged for the attractions that are visited and/or services received by the user. This may involve wirelessly sensing the presence of the article and receiving the account data therefrom as the user travels adjacent to sensors located at the entrance and/or exits of various attractions/services areas. Thus, for example, in an environment where a user is attending a theme park, the user may be charged for visiting certain premium areas of the park when their portable article is sensed within the premium area of the park.

In some exemplary arrangements, the article produced for the user may correspond to the particular transaction environment in which the article is to be used. For example if the article is to be presented in a theme park, the article may be produced as an attractive pendant including a design based on the logos of the theme park or the characters (such as cartoon or other characters) associated with the theme park. Further 3D printing techniques may be used to include in the transaction article that is produced, personalized information such as the user's name or initials or features selected by a user. For example if a theme park is associated with several different cartoon characters, the article produced for the user could be in the shape of the user's chosen character that is selected via inputs to the automated banking machine that operates to produce the item via 3D printing techniques. Of course these approaches are exemplary and in other arrangements, other approaches may be used.

In still other arrangements, the transaction articles produced may be suitable for generally continuous use in multiple different transaction environments. This would enable the user to use the article that is produced in making purchases of goods and/or services in any establishment where the account data and verification data can be read by suitable sensing equipment. Alternatively such articles produced may be programmed so that they are limited and can only be used during a given period of time. For example in the case of a theme park where a user has purchased a one-day pass, and the transaction article produced through operation of the banking machine may be operable to provide transaction data only during that day. In still other arrangements wireless or contact communication with the article may be used to selectively turn the transaction capabilities of the item on and off. Thus for example if the particular article is a token that is usable for making purchases in a particular type of store, wireless communication or other communication with a transceiver may be utilized to turn on the capabilities of the article to provide account or other transaction data when a user enters the store and the capabilities of the article may be turned off automatically when the user exits. This may be done securely so that user transaction data cannot be obtained from the item by unauthorized persons. Alternatively or in addition provision may be made for the transaction capabilities of the article to be selectively turned on and off by a user. This may be done, for example, by inputs to switches, keypads or other input devices that are included in the article. Such input devices may be included through the 3D printing techniques or other printing techniques for including circuitry and other features in articles as previously discussed.

Further some exemplary arrangements may include using an automated banking machine to produce an article that has additional verification features. Such features may include, for example, circuit components and microprocessors that have the capabilities to receive inputs from users. As previously discussed, such articles may include input devices such as user actuatable keypads or similar devices that can receive personal identification numbers or other codes from a user. Thus for example in some exemplary arrangements an article can be produced for a user that includes a small keypad into which a user can provide a selected input that enables the device to output user account data and/or otherwise carry out transactions until the capability is disabled. Such disabling capability may be provided by the user providing an additional input through the keypad or other device. Alternatively in other arrangements the article may be made so that use of the device in connection with conducting a transaction causes the circuitry therein to be operable responsive to the programming of the circuitry, to disable the operation of the device after a single transaction has been conducted. Thereafter the user would have to provide inputs or otherwise enable the article again if the user desired to conduct another transaction. For example in some arrangements if the article has been transaction enabled via inputs from a user, the article may wirelessly communicate via RF to deliver data corresponding to the user's account and data which indicates the genuineness of the article, in response to signals received from a transceiver associated with a particular merchant terminal or a merchant establishment. In situations where the article was not transaction enabled, the article would not provide such communications and no such transactions could be conducted.

In other arrangements other types of input devices may be included in transaction articles that are produced through operation of the automated banking machine. Such input devices may include, for example, sensors that are suitable for reading biometric inputs such as fingerprints. For example layers of suitable materials for sensing the ridges of a user's fingerprints may be utilized to receive the unique data associated with contact with an authorized user's finger. For example in some arrangements if the user's finger is not currently in contact with the sensing area of a given article, the article will not operate to communicate account data with transceivers that are connected to a transaction system. Alternatively in other arrangements, programming associated with the article may be enabled to remain operative to deliver account or other data for a period of time after the sensing area has been in contact with an authorized user's fingerprint. In still other arrangements other types of sensing devices may be utilized for purposes of verifying codes, images, audible words, voice recognition or other things that are uniquely associated with a user for purposes of verifying that the article is in possession of and is being used by an authorized user to conduct transactions. Of course these approaches are exemplary and in other arrangements other approaches may be used.

In still other exemplary embodiments enhanced security for card based transactions may be accomplished by providing a user with a card, token or other device that may be used as an adjunct to their transaction card when carrying out transactions. As previously discussed, enhanced security for card based transactions is achieved by including a circuit including a microprocessor on or in a card, which circuit executes algorithms and produces results which indicate that the card is genuine. Processor chips may be included on magnetic stripe cards for purposes of verifying card genuineness and reducing the risk that the magnetic stripe card has been counterfeited. In such arrangements the fact that the magnetic stripe of the card includes proper data identifying the user and/or their account and the chip on the card, when properly supplied with certain input signals and/or values produces a particular result, shows that the card is genuine. However, providing users with a card with both a magnetic stripe and a chip may be more expensive or have other drawbacks than providing to the user a card with a magnetic stripe alone. This is particularly true if the user has already received a magnetic stripe card that does not include a processor chip.

In exemplary arrangements in order to provide enhanced security, the user is provided with a separate article that can be used in conjunction with the magnetic stripe card. In some exemplary arrangements the user is provided with a card or token that includes a circuit including a processor programmed with suitable program instructions to produce results that can be used to verify authenticity of a card. Such programmed instructions may correspond to the algorithms developed by EMV Co. and which have been adopted by many transaction processors and card issuers. Of course these approaches are exemplary and in other embodiments other types of algorithms for card verification routines may be utilized.

In some exemplary arrangements the circuitry embedded in the validation device may include wireless communication capabilities so as to enable non-contact communication with a transaction terminal such as an automated banking machine. Such communication may include radio frequency communication of messages with a transceiver positioned in the machine. Such a transceiver may include an RF transceiver positioned within the card reading device of the banking machine that reads the magnetic stripe data on a card. Alternatively the transceiver may be located in another location on the automated banking machine. An advantage of positioning the transceiver in the card reader is that it may be used to communicate with circuits including microprocessors that are embedded in cards that include a magnetic stripe, as well as with separate verification articles that are separate from the magnetic stripe card. For example in some arrangements the transceiver may operate to communicate with the verification article which is positioned in close proximity to the card slot of the automated banking machine. In such arrangement while the card bearing the magnetic stripe is received and read by the card reader, the verification article is placed in close proximity to the card reader slot and communicates with the transceiver so as to receive the initiation messages and provide the results in response thereto so as to confirm the genuineness of the associated magnetic stripe card. Further in exemplary arrangements, the verification article is programmably changeable through communication with the transceiver so that in subsequent transactions the verification results data produced through operation of the circuit and microprocessor on the verification article corresponds to different results required to verify the identity of the magnetic stripe card in such subsequent transactions.

In other arrangements the verification article may include other types of devices. For example in some arrangements the verification article may comprise a wearable computer device which is worn by a user. In such arrangements the programming associated with providing the results data to the transaction terminal which confirms the authenticity of the magnetic stripe card, is provided through communication with the RF transceiver and processor circuitry included in the wearable computer article. The processor included in the wearable computer executes the algorithms that provides the results which verify the authenticity of the card. Further one or more data stores associated with the wearable computer article enables the results to be modified and to correspond to what is required to authenticate the card in subsequent transactions. Further in some exemplary arrangements the wearable computer article may include data for multiple magnetic stripe cards so that each may be authenticated through communication with the wearable article. As a result the wearable computer device can serve as the verification article for multiple magnetic stripe cards.

In still other exemplary arrangements a portable communication device such as a smart phone may include programs that cause the at least one processor in the smart phone to execute the verification algorithms that receive inputs and produce results that can be used to authenticate one or more magnetic stripe cards. Such a smart phone may communicate via radio frequency communication with a transceiver in an automated banking machine so as to receive the initiation data and provide the necessary results which help to prove the authenticity of the card. This may be done via communication by a near field communication, Bluetooth or other suitable communication type.

Thus these exemplary arrangements enable a magnetic stripe card that does not include a processor thereon to nonetheless be verified as a genuine card by a user having possession of the verification article which executes the verification algorithms and provides to a transaction terminal the one or more results that indicate that the card is genuine. Such approaches can be used to avoid the need to deploy magnetic stripe cards that have included thereon processors which execute algorithms to verify the genuineness of the card. Of course these approaches are exemplary and in other embodiments other approaches may be used.

In still other exemplary arrangements remote communications may be utilized for purposes of verifying the genuineness of a transaction card such as a magnetic stripe card. In such exemplary arrangements, a portable device such as a smart phone with the ability to communicate over a wide area network may execute the algorithms that produce results which demonstrate the genuineness of a card. These may include, for example, the EMV algorithms or other algorithms that are normally executed on a microprocessor chip that is resident on a card. Rather than providing short distance RF communication as in the previously described embodiment, such a smart phone or other device may provide other wide area network communications such as via cellular phone or wireless Internet connections to the transaction processing host that processes the card data. The communication of the verification data via the wide area network may be encrypted to further assure that such communications are not fraudulent. Further in order to avoid the risk of fraudulent communications, the location of the verification article which comprises a portable wireless device such as the smart phone, can be determined by the one or more computers associated with the system via global positioning system signals to verify that the device is in proximity to the transaction terminal. This may be done using features such as those disclosed in U.S. Pat. Nos. 8,479,983; 8,505,814; 8,540,147 and/or 8,561,889 the disclosures of each of which are incorporated herein by reference in their entirety.

Of course it should be understood that these approaches may be combined or used in conjunction with other approaches that are described in the incorporated disclosures for purposes of verifying that a transaction that a user is requesting at an automated banking machine or other transaction terminal, is authorized by the user. Such approaches may include, for example, approaches where the user is contacted via their smart phone or other mobile wireless device through an automated system, and requested to provide at least one input to verify that the transaction should proceed. In such arrangements the portable wireless device of the user may operate not only to provide a message to the system to indicate that the transaction should proceed, but may also communicate with the system to receive the necessary initiation data and provide the results which demonstrate that the user card being utilized in connection with the transaction, is genuine. Such systems may utilize features such as those described in U.S. Pat. No. 8,353,450 the disclosure of which is incorporated herein by reference in its entirety. Of course these approaches are exemplary and in other arrangements other approaches may be used.

FIGS. 9-17 describe an alternative automated banking machine generally indicated 143. Machine 143 is generally similar to machine 12 previously described except as otherwise indicated.

Machine 143 includes at least one recycler module generally indicated 144. In exemplary embodiments the recycler may be a belt type recycler. Exemplary arrangements may include features like those described in U.S. Pat. Nos. 6,367,692; 6,367,691; and/or 6,264,102 the disclosures of each of which are incorporated herein by reference in their entirety.

The exemplary embodiment further includes one or more cleaner/disinfecting devices generally indicated 146. In exemplary embodiments the cleaner/disinfecting devices may include one or more ultraviolet radiation emitting devices. Such a device may be used in an ultraviolet germicidal irradiation (UVGI) cleaning/disinfecting method. Such devices may be operative to emit UV-C or other radiation that operates to kill bacteria and viruses on surfaces, including the surfaces of currency bills (which are alternatively referred to herein as notes). In addition or in the alternative the cleaner/disinfecting devices may also include devices that operate to scrub currency notes and to apply vacuum or other forces designed to cleanse the surfaces thereof of impurities and other unwanted substances. In some arrangements the cleaner/disinfecting devices may be usable to kill disease transmitting organisms that may reside on the surfaces of currency bills. Alternatively or in addition in some arrangements such cleaner/disinfecting devices may be usable to remove undesirable substances such as the residue of illegal drugs or contaminants or other impurities that may be present on bills, so that such substances cannot be detected or absorbed through the skin by persons who receive and handle such bills.

Figure 10:
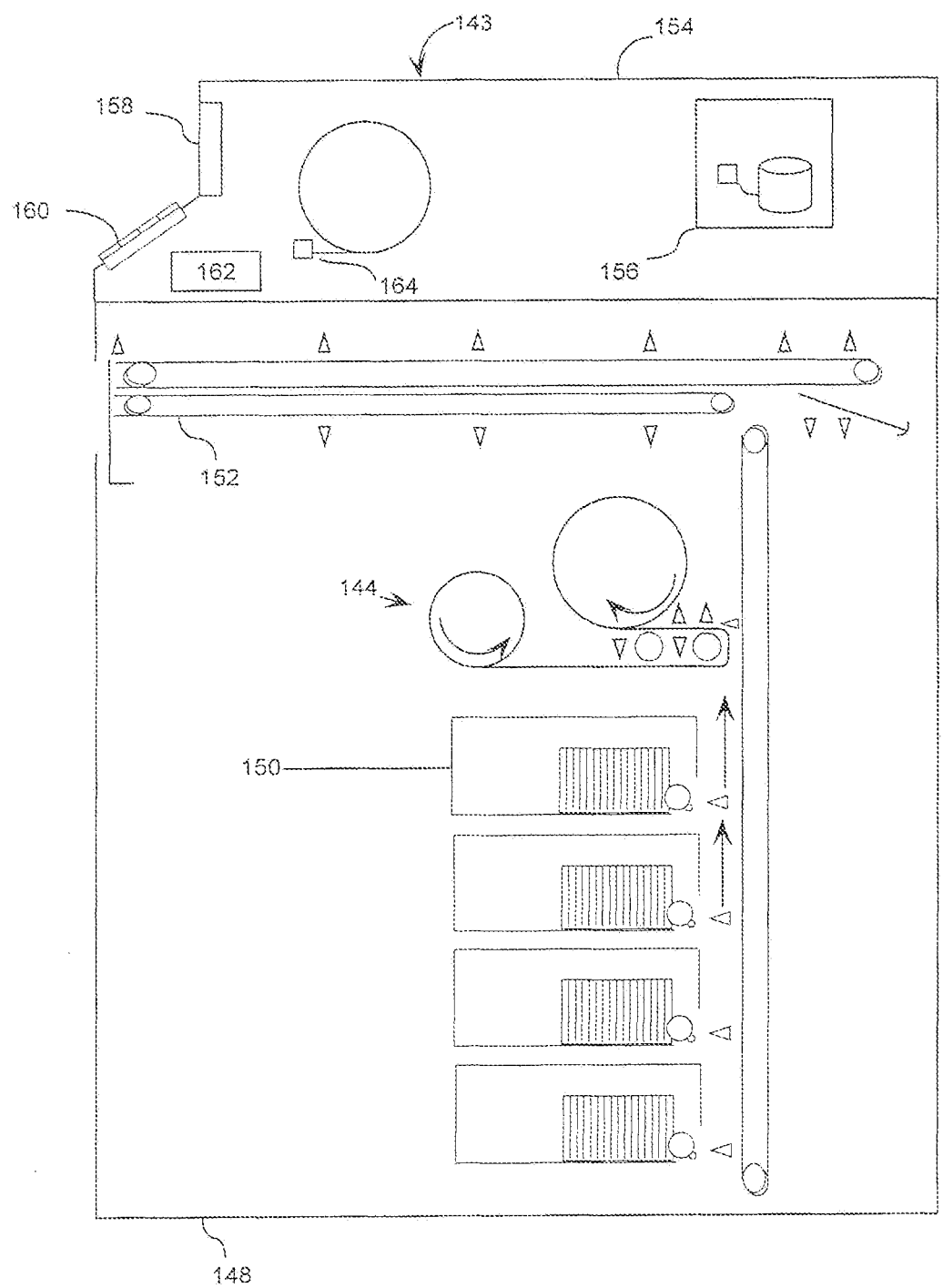
FIGS. 10-12 are schematic views demonstrating operation of the exemplary automated banking machine shown in FIG. 9 in connection with dispensing disinfected items.
Figure 11:
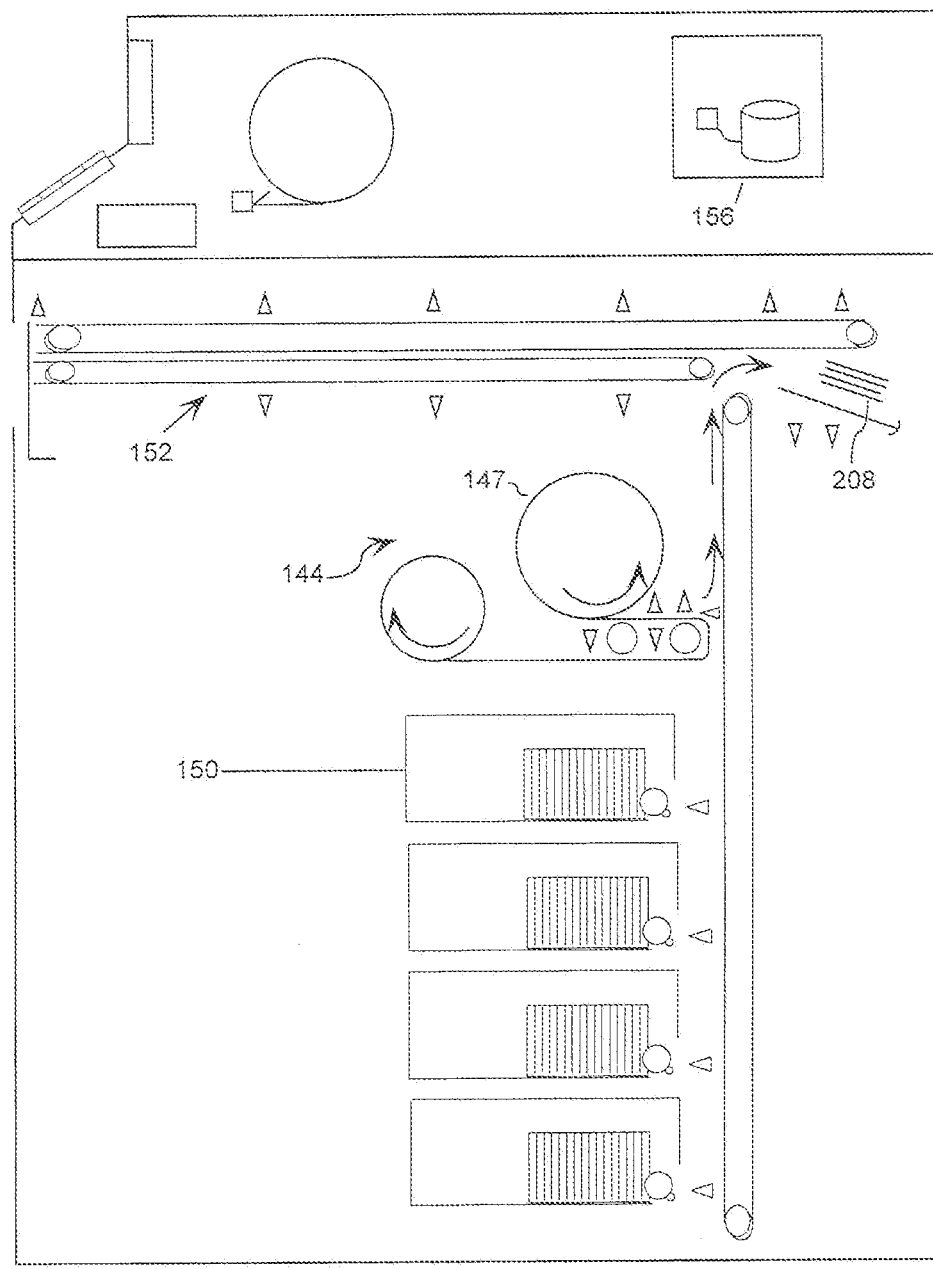
Figure 12:
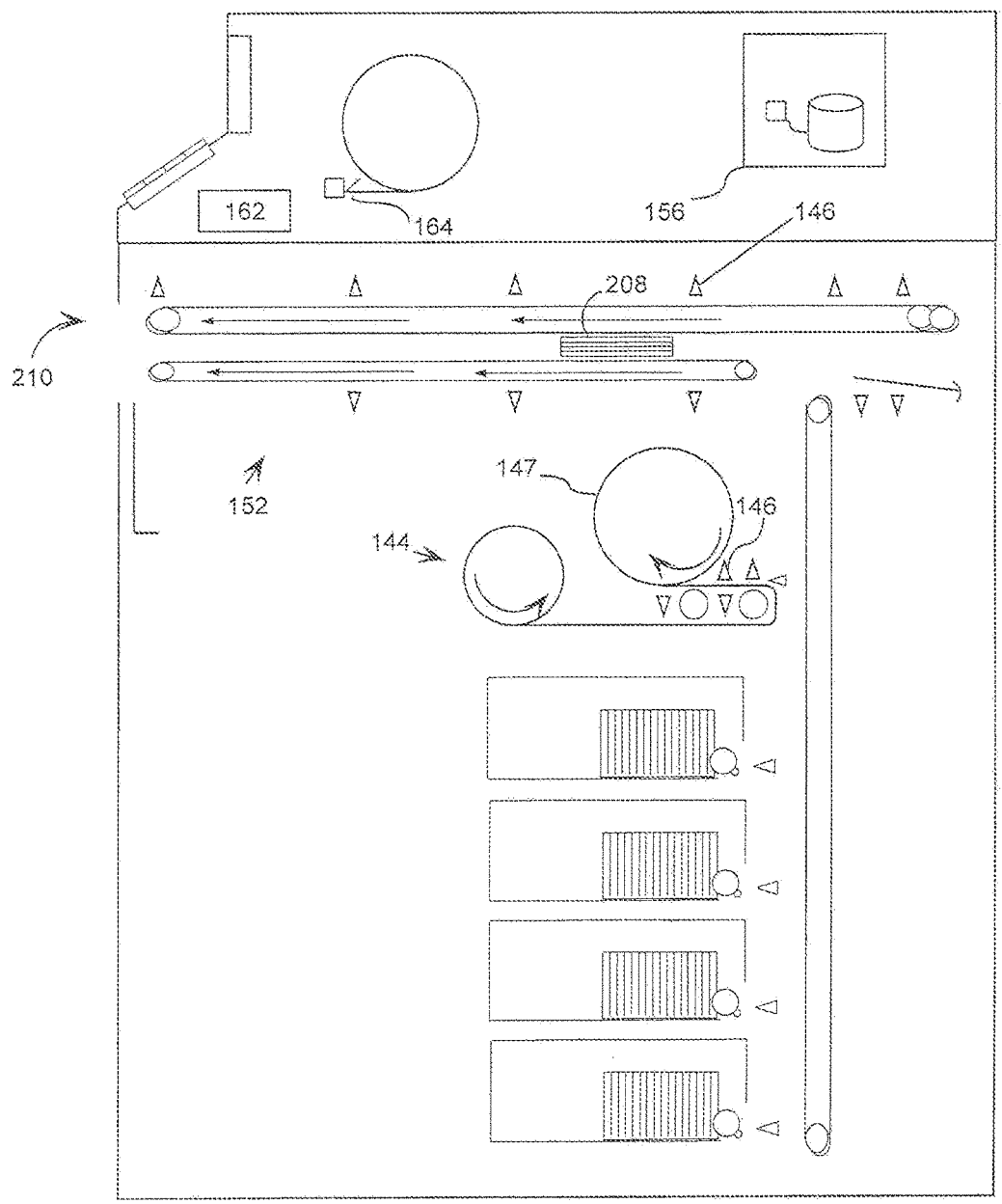
Figure 13:
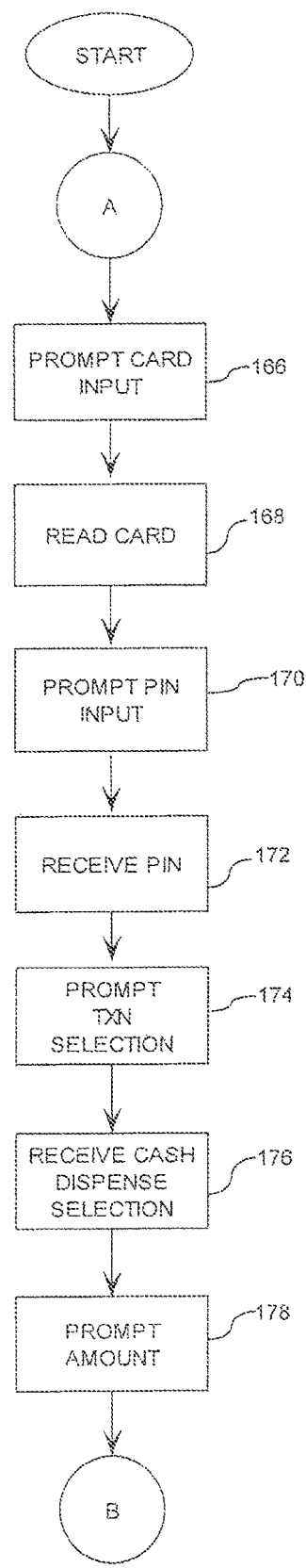
Figure 14:
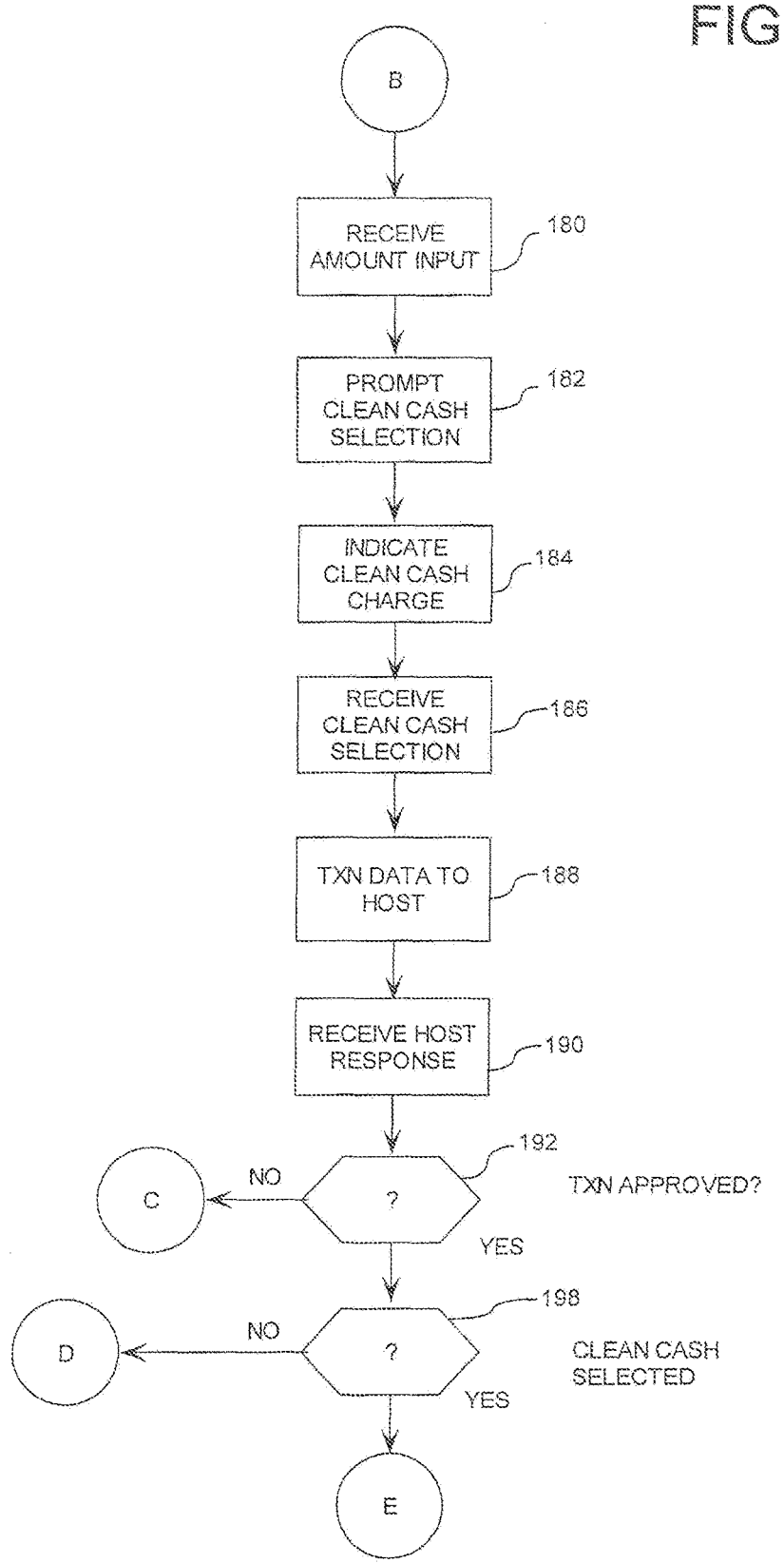

FIGS. 10-12 schematically show certain components of exemplary automated banking machine 143. In the exemplary arrangement the automated banking machine includes a lower chest portion 148. Chest portion 148 includes bill dispenser mechanisms 150. The exemplary bill dispenser mechanisms 150 may operate to selectively dispense currency bills that are stored in the machine and deliver them to machine users through a presenter 152. The bill dispenser mechanisms include features of the type shown in U.S. Pat. No. 7,780,073, the disclosure of which is incorporated herein by reference in its entirety. In other exemplary arrangements the bill dispenser mechanisms may include bill recycler mechanisms. These may include mechanisms that both receive and store currency bills and also selectively dispense currency bills from storage. These currency recycler mechanisms may operate in the manner of incorporated disclosures, including U.S. Pat. Nos. 6,331,000 and 8,356,748, the disclosures of each of which are incorporated herein by reference in their entirety. Further in some exemplary arrangements the automated banking machine may include some mechanisms that are suitable only for dispensing sheets from storage, while others are usable to both receive and store as well as dispense sheets. The particular configuration utilized will depend on the particular requirements of the machine. Further in the exemplary arrangement the chest 148 houses the belt type recycler mechanism of the exemplary arrangement 144. Of course it should be understood that the exemplary embodiments include actuators, controllers, sensors and many other mechanisms not specifically shown that enable the machine to carry out the functions that are hereinafter described.

The exemplary automated banking machine 143 further includes a top housing portion 154. The top housing portion 154 is positioned above the chest and houses the machine controller 156. The top housing 154 also supports the display 158 and the keypad 160. The exemplary top housing further supports the card reader 162 and the printer 164. The top housing also may support additional devices such as function keys, input devices, output devices, transceivers and other suitable devices for the operation of the machine.

In the exemplary arrangement the automated banking machine 143 is operative to utilize the cleaner/disinfecting devices 146 to produce currency bills that are generally free of bacteria, viruses and other potentially harmful items so as to reduce the risk of disease (or other illnesses) that may occur from handling such items. This is done in the exemplary embodiment by operating the currency dispenser mechanisms responsive to the at least one controller 156 when the machine is not performing transactions for a user. This is done as represented in FIG. 10 by the machine operating to move currency bills from at least one bill dispenser mechanism 150 into storage on the belt recycler 144. During the exemplary operation the cleaner/disinfecting devices operate so as to irradiate the bills before they are loaded onto storage in the belt recycler device using UV-C emitters. In the exemplary arrangement the bills moving into storage on the bill recycler move in supported connection with sets of transversely staggered belts. These belts which move the bills into engagement with a bill storage roll 147 of the belt recycler are offset so that all of the surface areas of all the bills are irradiated.

Further, in some exemplary arrangements the belts which move the previously irradiated bills include impregnated silver or other substances that are operative to retard the growth of harmful bacteria. Similarly, the storage roll, tape, or other storage media can include such substances that will retard and/or prevent the growth of undesirable bacteria and viruses on currency bills. In this way the machine operates to store a supply of clean, disinfected bills on the storage roll 147 of the bill recycler 144. In alternative embodiments, cleaned or disinfected currency bills can be stored by the machine in one or more currency cassettes instead of (or in addition to) on the storage roll 147. Such a currency cassette can be designated (or recognized) by the controller (or the machine) to only contain (or hold) cleaned or disinfected currency bills.

Further in some exemplary arrangements the cleaning/disinfecting devices may operate to not only irradiate the bills but also to clean the bills so as to remove undesirable substances. This may include, for example, passing the bills through a cleaning mechanism such as sets of moving brushes or other devices to loosen particulate materials or other materials that are adhering to the bills.

Further in exemplary arrangements a vacuum system may operate to pull and collect the impurities that are dislodged from the bills so as to carry the impurities away from the bill surfaces. Such systems may be used for example to remove residues of narcotics that may be present on the surfaces of bills that have been passed by persons who use or deal in illegal drugs. This may avoid, for example, persons receiving from the machine currency bills that may cause drug sniffing dogs or other narcotics sensing systems to be triggered from the use of the particular bills. Of course it should be appreciated that additional or alternative methods for cleansing bills and disinfecting bills may be used. This may depend on the quality of the particular bills. For example in some countries where plastic currency notes are used, certain solvent or other cleaning materials may be appropriate for use in connection with disinfecting such bills that would not be appropriate for use in connection with paper or cloth bills. Alternatively in some arrangements heating or cooling devices may change the temperature of bills to kill undesirable organisms. Of course the particular type of cleaner/disinfecting devices included in the automated banking machine will depend on a number of different circumstances that are involved and the particular substances and organic material that is desired to be removed or neutralized.

The exemplary embodiment of the automated banking machine may be operated responsive to programmable instructions stored in the one or more data stores associated with controller 156. The exemplary logic flow carried out by machine 143 is represented in FIGS. 13-17. In operation of the exemplary machine, the user may be prompted through an initial display screen output to input their user card to the card reader of the machine. This is represented in step 166. The controller 156 in the machine operates to cause the card reader to read data from the card that is usable to identify the financial account. This is represented in the step 168. The controller then operates in accordance with its programming to output through the display a prompt message which instructs the user to input their personal identification number (PIN). This is represented in a step 170. The controller then operates to receive the user input of the PIN through the keypad in a step 172.

The controller 156 then operates to cause the display to output at least one screen that prompts the user to make a transaction selection. This may include a step that presents the user with a display prompt to select a particular account on which their transaction is to be conducted, such as checking or savings. This is represented in a step 174. For purposes of this example, it will be assumed that the user requests the transaction that includes a dispense of cash from the machine. The controller operates to receive the user's input request to receive cash through one or more input devices. This is represented in a step 176. Once the user has input their selection to receive a cash dispense, the controller operates to provide at least one output through the display that prompts the user to input the amount of cash they wish to have dispensed. This is represented in step 178. The controller then operates to receive the user input amount through a user input device on the machine. This is represented in a step 180.

In the exemplary arrangement the program steps stored in the at least one data store associated with controller 156 include data that enables the controller to output a display that prompts a user to provide at least one input concerning whether they wish to receive clean and disinfected cash from the machine. This is represented in a step 182. The machine also provides at least one output that indicates to a user that a charge will be assessed for receiving clean and disinfected cash from the machine. This is represented in a step 184. Steps 182 and 184 may be combined as a single step. In response to these outputs, the machine operates to receive at least one input from the user which indicates whether they wish to receive clean and disinfected cash from the machine or not. The receipt of this indicating input is represented in the step 186.

After receiving the input from the user concerning whether they wish to receive disinfected and cleaned cash, the at least one controller 156 operates in accordance with its programming to send the transaction data associated with the user selected transaction to the remote host computer. This is represented by step 188. The host computer of the exemplary embodiment operates in a manner like that previously described to obtain a determination whether the transaction is authorized or not. It should be appreciated that in this exemplary embodiment the user has selected to receive cleaned cash from the machine. The associated surcharge associated with receiving the cleaned cash will be included in the amount to be assessed to a user's account if the transaction is approved. If the user has not elected to receive cleaned and disinfected cash from the machine, the surcharge is not included in the transaction data sent to the host concerning the amount of the transaction. Of course it should be understood that this approach is exemplary and other approaches, such as independently assessing the surcharge fee through separate machine communications with the host or another computer (e.g., a remote server), may alternatively be used.

As represented in a step 190, the automated banking machine receives a response from the host which indicates whether the transaction is approved or not approved. The at least one controller operates responsive to the received host message in a step 192. If the transaction is not approved, the at least one controller 156 operates to cause the display to provide an output that the transaction has been denied. This is represented in a step 194. The controller also operates to return the user's card in a step 196 and returns the machine to a wait state for the next transaction.

If in step 192 the transaction is indicated to be approved, the at least one controller 156 then makes a determination whether the user has elected to receive cleaned and disinfected cash from the machine. This is indicated in a step 198. If the user has not elected to receive cleaned and disinfected cash from the machine, the at least one controller operates in accordance with its programming to dispense the cash from the bill dispensing mechanisms 150. This cash has not been cleaned or disinfected through operation of the machine. This is represented by a step 200. The machine is operated to dispense the cash to the user and provide (e.g., print) a receipt as reflected in step 202. The controller then operates the machine in step 204 to cause the card reader to return the card to the user. The controller 156 then operates to notify the host that the cash was successfully dispensed to the user so that the host or other connected server may assess the user's account for the value of the cash dispensed. This is represented in a step 206. In the exemplary embodiment if the user has elected in step 198 to receive (high) quality cash (e.g., uncirculated, new, cleaned, and/or disinfected cash), then the at least one controller operates at step 212 (in FIG. 17) to cause the quality cash stored in the recycler 144 to be dispensed to the user. This is accomplished by the controller operating to remove bills from the storage roll of the belt recycler 144 and to stack the clean bills in a stack 208 of the presenter 152, as shown in FIG. 11. Once the stack of cleaned and disinfected currency bills has been built in the presenter, the stack 208 is moved through operation of the presenter through a bill outlet opening 210 from which the bill stack may be taken by the user. This is represented in FIG. 12. In some exemplary embodiments the bill cleaning and disinfecting devices such as ultraviolet emitters or other irradiation devices may operate during the time period when the bills are being delivered from the belt recycler 144 and to the presenter. Further UV disinfecting devices and other devices 146 may be operated in various other locations in the machine to help assure that the bills which have been disinfected do not attract contaminants as they are moved from the belt recycler to the user. Of course this approach is exemplary and in other embodiments, other approaches may be used.

In an exemplary embodiment a clean currency bill has at least one higher factor of cleanness relative to a non clean currency bill. For example, factors of bill cleanness can include newness, age, received a cleaning treatment (e.g., radiation treated), timeliness of cleaning treatment received, type of cleaning treatment received, material quality (e.g., paper quality) of the bill, uncirculated versus circulated, etc. A non clean currency bill can include for example a bill that has been used in public circulation, or a bill that has at least one defect detected by a note analyzer of the machine, or a bill that has not been treated by the machine, etc. A factor of cleanness can be deemed (or recognized or designated or determined) by at least one controller associated with the machine. Again, an exemplary automated banking machine can dispense both clean and non clean currency bills (or notes) of the same denomination value.

As represented in FIG. 17, the machine operates to dispense the cleaned and/or disinfected cash to the user from the machine as represented in step 212. Thereafter the machine operates in accordance with its programming to provide (e.g., print) a receipt for the user as represented in step 214. The at least one controller 156 then operates to cause the card reader to return the card to the user in a step 216. The controller then operates to notify the host computer that the cash was dispensed successfully from the machine. This is represented in a step 218. As previously explained, the messages from the automated banking machine cause the host to assess the user's account for the value of the cash dispensed including the surcharge for the user receiving the cleaned and disinfected cash. Further in this exemplary arrangement the at least one controller 156 operates in accordance with its programming to then (if determined necessary) replenish the supply of cleaned and disinfected cash stored in the recycling mechanism 144. This is done in the manner previously described by moving currency bills from the dispensers 150 into the storage roll of the recycler 144. This is represented by a step 220. Of course it should be understood that these transaction flows are exemplary and in other automated banking machine arrangements, other or alternative approaches may be used for providing a user with bills that have been cleansed of potentially harmful or undesirable impurities.

In other exemplary embodiments the machine 143 can operate to analyze the quality of currency notes stored in the cash dispenser 150. For example, during a cash reloading process the cash dispenser 150 is supplied with currency notes. The added currency notes may be inside currency cassettes that get inserted into the cash dispenser 150. The controller is programmed to cause notes to be removed from these currency cassettes and then moved past a note analyzer, which can measure several factors of note quality. The note analyzer can be used to determine whether a note is of high quality. For example, a high quality note may not need to be cleaned and/or disinfected. As a result, a high quality note can be directly placed (without cleaning) onto a storage roll of the recycler 144. Of course notes determined to be of high quality may also be thoroughly cleaned before being stored onto a storage roll of the recycler 144.

In another exemplary embodiment a designated portion of the cash dispenser 150 includes currency cassettes that hold uncirculated (brand new) currency notes. That is, these notes have never been in public circulation. Thus, these notes should be relatively free of any dirt, disease, germs, viruses, harmful bacteria, etc. The controller is operable to maintain a real time count of the quantity of uncirculated notes (and their respective denominations) that are available to be dispensed by the machine. Uncirculated notes can be dispensed to user for an extra fee. The fee assessed to a user can vary. For example, the extra fee may be on a per note basis, a single fee for a specific quantity of notes (e.g., three notes), or a single fee for the entire cash dispense, etc. The uncirculated note fee may be waived for select users, such as VIP customers. Also, some machine users may be permitted the option to withdraw more uncirculated notes than other users.

The uncirculated notes stored in the machine may also be of higher denominational value than regular (unclean) notes stored in the machine. For example, an uncirculated note may be a $50 and/or a $100 bill, whereas a regular note may be a $20 bill. As can be appreciated, the arrangements allow a user of an automated banking machine (e.g., an ATM) the ability to easily obtain an uncirculated note, such for use as a gift.

Figure 24:
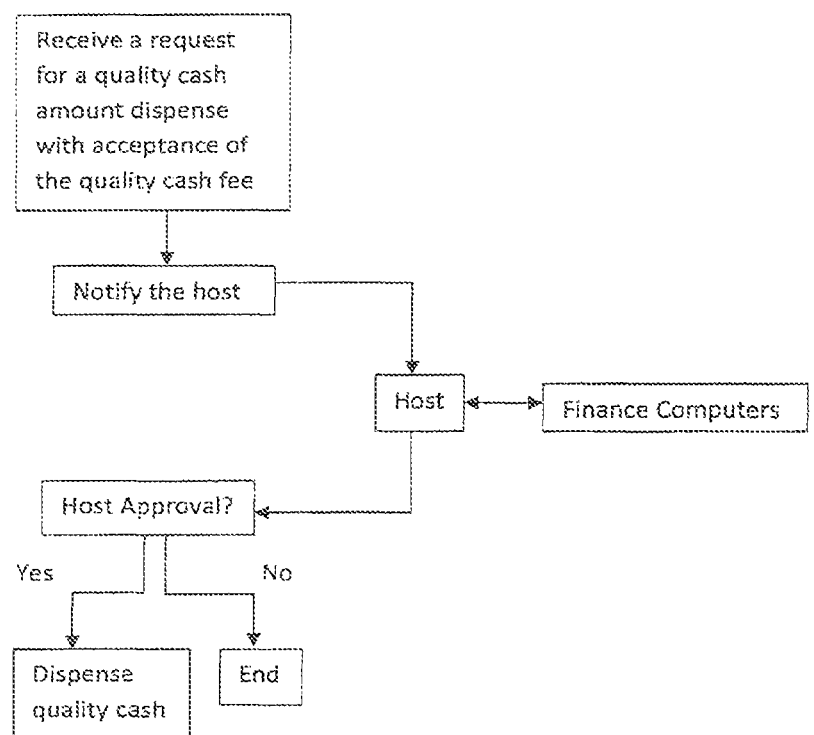
FIGS. 24-27 are schematic representations of steps carried out by logic flow associated with automated banking machine transactions involving quality cash.

FIG. 24 shows a further exemplary programming logic flow that can be carried out by the machine 143. As can be seen, the machine can receive a user request for a cash withdrawal transaction which includes quality cash and user acceptance of the extra quality cash fee. The machine sends a transaction authorization request to the host. The authorization request includes the cash withdraw amount and the extra fee amount. The amounts are presented to the host to be assessed against the user's account. The amounts may be combined by the machine into a single total value that is presented to the host. Upon host approval of the transaction, the machine operates to dispense the requested amount of quality cash. Upon host disapproval of the transaction, the machine operates to notify the user that the transaction request is denied, which may include ending the user session with the machine.

Figure 25:
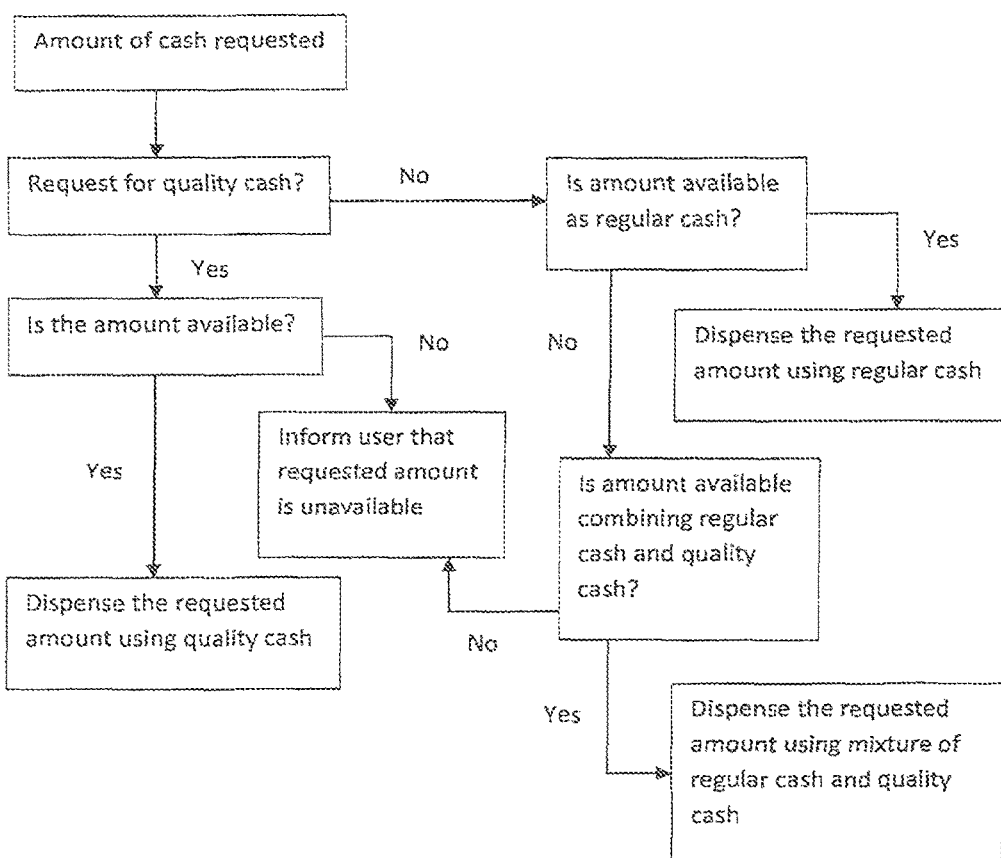

FIG. 25 shows a further exemplary programming logic flow that can be carried out by the machine 143. As can be seen, the machine can determine the real time quantity and denomination of both clean (quality) and unclean (regular) notes currently available to be dispensed.

The machine can compare a requested amount of quality cash to the amount of quality cash currently available. If available, then the total amount of quality cash can be dispensed. Otherwise the user can be informed that the requested amount of quality cash is unavailable. The logic flow may then lead the user back to a screen where a smaller amount of quality cash can be requested. For example, the machine may notify the user of the total amount of quality cash available to the user. The machine may also provide the user an option to mix regular notes with quality cash to meet the total cash withdrawal amount. The logic flow may eventually lead the user back to a screen where a regular cash dispense can be requested.

The machine can also compare a requested amount of regular cash to the amount of regular cash currently available. If available, then the total amount of regular cash can be dispensed. Otherwise the user can be informed that the requested amount of regular cash is unavailable. Alternatively, the machine logic flow may try to meet the requested total cash withdrawal amount by mixing the available regular notes with some quality cash (e.g., a small amount, such as one note). The user would not be charged a fee for receiving the quality cash.

Figure 26:
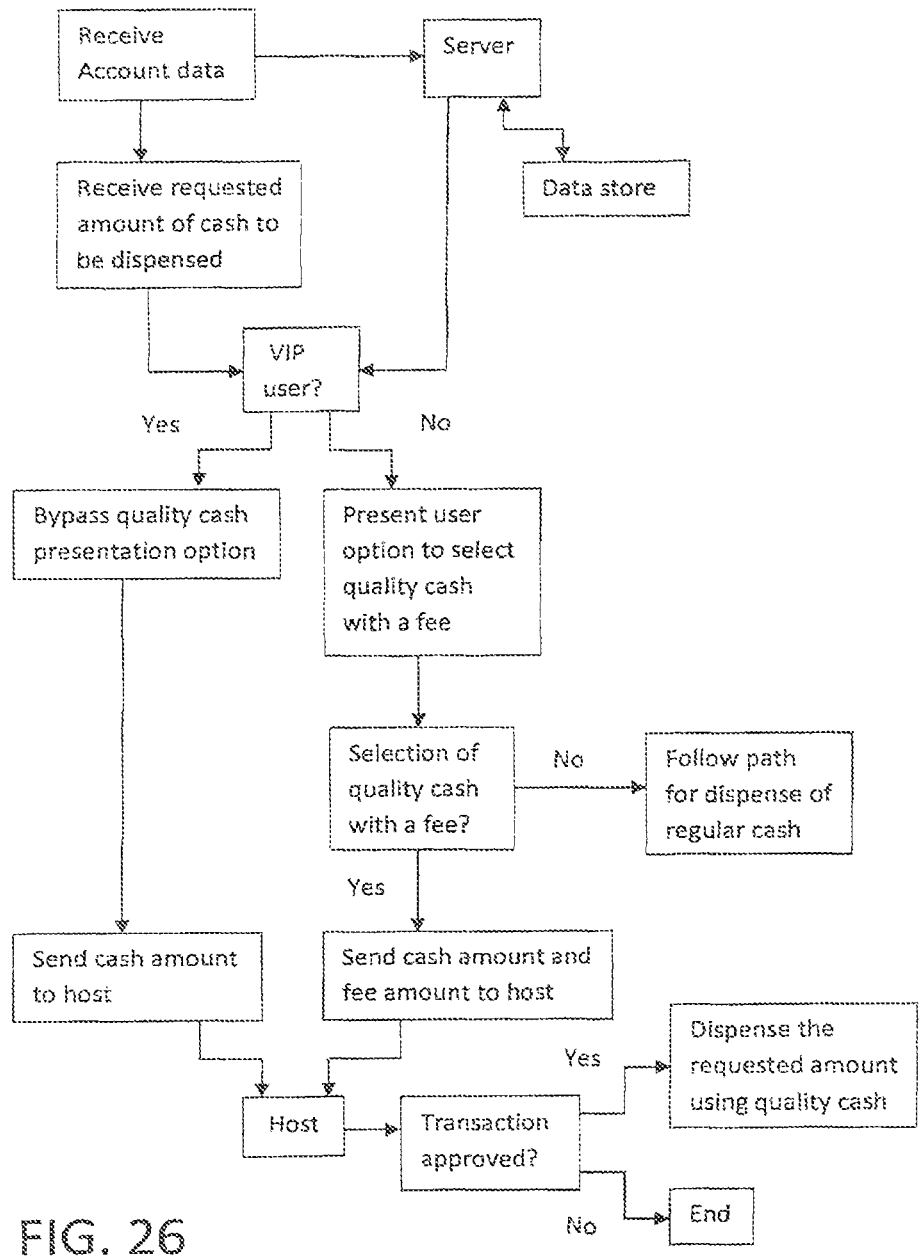

FIG. 26 shows a further exemplary programming logic flow that can be carried out by the machine 143. As can be seen, the machine can communicate with a server to determine whether the current user is in a special program (e.g., a VIP user). The machine-to-server communication is independent of the transaction host. That is, the machine can (directly) communicate with the server without involving the host in the communication path.

The machine sends user data (e.g., account data or other user identifying data) to the server. The server operates to determine whether the user data corresponds to VIP user data. The server can access a data store that includes the VIP user data for a plurality of users that are to automatically receive quality cash. Depending on the VIP program, the user may or may not be assessed the extra fee. As can be seen, if the user is determined to be a VIP then the logic flow causes the machine to bypass presenting the normal user option to select purchasing quality cash. The machine can send a transaction authorization request to the host. Again, the machine has an ability to send an authorization request that does not include the extra fee that is normally assessed to a user account for receiving quality cash.

As can be seen, if the user is determined not to be a VIP then the logic flow causes the machine to present the user option to select purchasing quality cash. If the non VIP user selects to pay the fee to receive quality cash then the machine sends a transaction authorization request to the host that includes the extra fee for receiving quality cash. The extra fee can be assessed to the user's account through operation of the host. As discussed in more detail later, in other embodiments the extra fee can be assessed by use of an independent server instead of the host.

Figure 27:
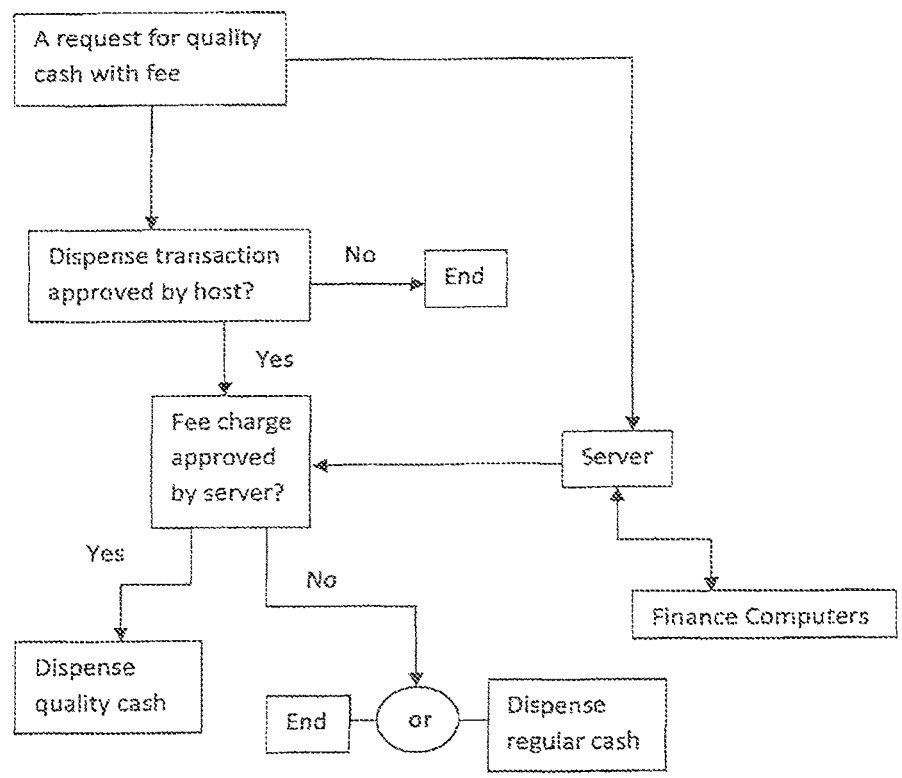

FIG. 27 shows a further exemplary programming logic flow that can be carried out by the machine 143. As can be seen, the machine can independently communicate with a server which can assess the extra fee associated with a quality cash dispense. The charging of the extra fee amount can be a separate financial transaction that is carried out independent of the cash withdrawal transaction. That is, the extra fee transaction can be performed independent of host involvement. The host can still handle (and approve) the cash withdrawal transaction.

As shown, user data (e.g., a user account number or data usable to determine a user or an account) can be sent from the machine to the server. The server can communicate with one or more financial computers to determine whether the user account can cover (is good for) the extra fee. The server may assess (debit or charge) the fee at this time in the logic flow or may wait until later receiving a confirmation message from the machine that the amount of quality cash was properly dispensed from the machine. The server notifies the machine of the determination. Upon receiving a fee approval message from the server, the machine operates to carry out the dispense of the requested amount of quality cash. However, upon receiving a disapproval message from the server the machine operates to either end the user session or allow the user an option to request a cash withdrawal involving regular cash. It should be understood the steps shown are exemplary, and in other embodiments other arrangements of the steps can be used. For example, the machine may be notified of the server's determination regarding the extra fee assessment before the machine sends the transaction authorization request message to the host for approval of the cash withdrawal transaction. Again, the machine logic flow allows for both one transaction portion carried out through machine-to-host communication and another transaction portion carried out through machine-to-server communication. Each communication portion can be independent of the other.

It should be understood that the logic flows shown in FIGS. 24-27 are exemplary. That is, in other automated banking machine logic flow arrangements, other or alternative approaches or programming may be used for providing a user with quality cash. Likewise, other or alternative approaches or programming may be used for assessing (if necessary) the extra fee.

In alternative embodiments automated banking machines may accept and/or dispense other types of documents that may be desirably disinfected. For example, such machines may accept and disinfect financial checks, tickets, vouchers or other types of documents representative of value. Disinfecting such documents may reduce the risks of contacting viruses or bacteria by persons who subsequently receive or handle such documents. Machines for handling such documents may include features like those described in the following U.S. patents, the disclosures of each of which are incorporated herein by reference in their entirety: U.S. Pat. Nos. 8,763,897; 8,695,874; 8,695,873; 8,701,985; 8,613,388; 8,608,060; 8,608,055; 8,573,483; and 8,517,260.

Figure 19:
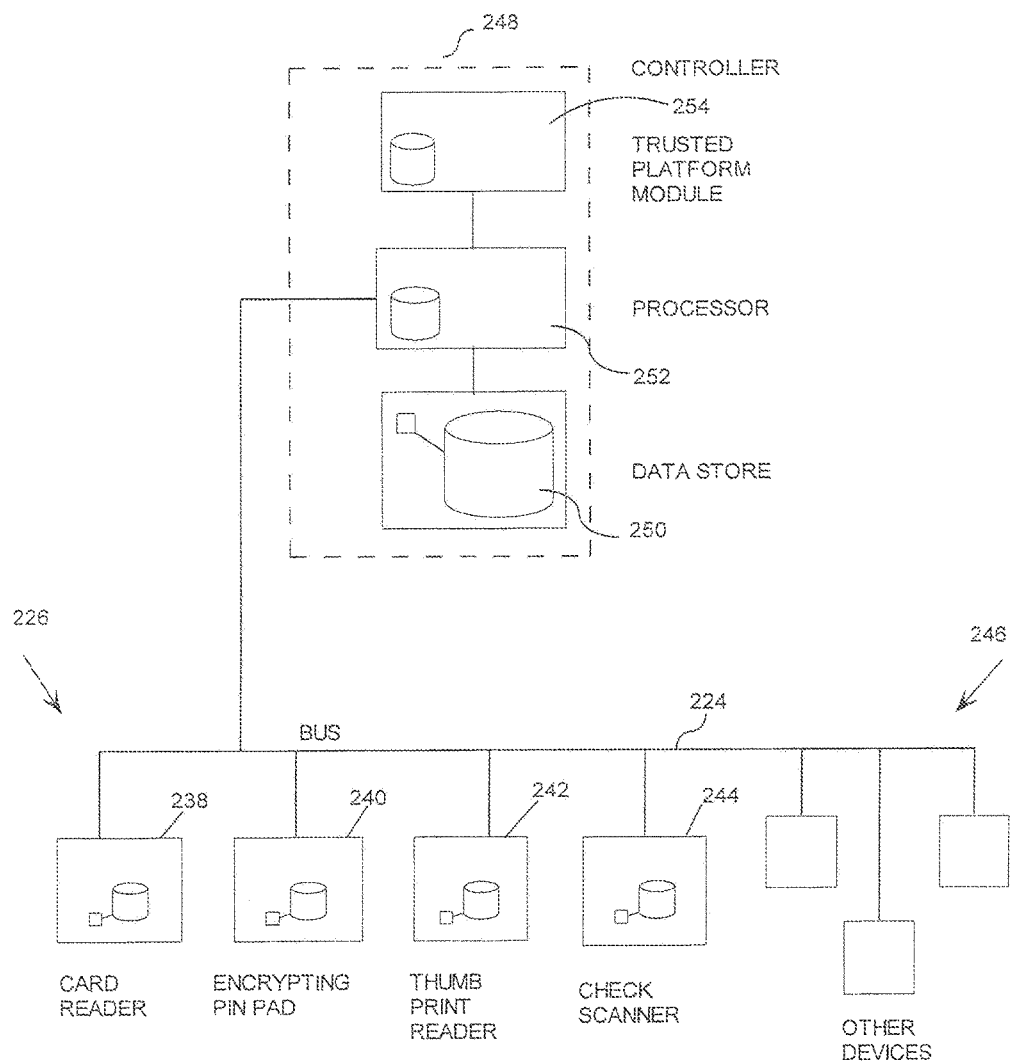
FIG. 19 is a schematic view of a controller and devices used in an exemplary automated banking machine.

FIGS. 18 and 19 represent the software and controller architecture associated with an alternative exemplary automated banking machine. As can be appreciated in exemplary embodiments the controller includes circuitry which has one or more processors that execute computer executable instructions. Computer executable instructions corresponding to various types of computer programs are stored in the at least one data store associated with the processor. These computer executable instructions when executed cause the machine to operate to carry out the transaction functions such as the functions previously described.

The exemplary computer executable instructions include a number of different software programs. These software programs as represented in FIG. 18 may include an operating system schematically indicated 222. Operating system 222 may include, for example, a Windows® operating system, a Linux operating system, a Chrome operating system or other suitable operating system for the particular environment in which the processor and associated software operate. The operating system also communicates via a communications bus schematically indicated 224. Communications bus 224 may include a proprietary or non-proprietary communications bus such as for example a Universal Serial Bus communications architecture that is suitable for communicating with transaction function devices generally indicated 226, which are later described in detail. The exemplary software architecture includes a plurality of device drivers schematically indicated 228. Device drivers 228 provide an electronic communication interface to the transaction function devices 226. In the exemplary arrangement specific device drivers for each particular transaction function device are included in the software architecture.

In the exemplary arrangement the device drivers 228 are in operative communication with an XFS interface 230. The XFS interface may in some exemplary arrangements comprise a device interface layer that meets the requirements of the CEN Extensions for Financial Services Standard. This Standard provides a standardized software interface for numerous different types of devices that are used in financial systems. By including an XFS interface the exemplary software architecture provides a standardized software interface to which different software developers may interface their machine operating software applications. This is possible because the communications that are necessary to operate and receive data from the devices are presented in a standardized format which is available to application developers. Of course this approach is exemplary.

Further in the exemplary software architecture a software application 232 is included. In the exemplary embodiment the software application includes the computer executable instructions that are executed by the at least one processor of the at least one controller to cause the machine to carry out the transaction functions of the machine. In exemplary arrangements the application software is what causes the machine to perform the necessary activities and to operate the various devices so as to enable the machine to carry out the various types of financial transactions of which it is capable.

The exemplary software architecture further includes some other programs including security software programs represented 234. The security software 234 may include types of software that are suitable for the particular type of automated banking machine. Such security software may include, for example, firewall software that prevents the machine from connecting to unauthorized network addresses. Security software may also include software that is usable to identify viruses or other exploits that might execute on the machine. The security software may also include software that operates to enable security features of the machine and provide secure communications of the type hereinafter described. The exemplary software architecture further includes certain utilities schematically represented 236. Utility software may include, for example, software that is needed to perform ancillary functions associated with the machine. This may include, for example, software that keeps track of currency stored in the machine so that the machine can report its current status to one or more remote computers. The utility software may also include in some arrangements predictive maintenance software which monitors aspects of machine operation and reports conditions that are likely to need attention in the near future. This may include potential device failures, replenishment of supplies such as paper, cash or other things that will likely need to be done to the machine. Various types of utility software may be included in the software of the machine depending on the particular type of automated banking machine involved.

As represented in FIG. 18, the exemplary transaction function devices communicate messages through the bus 224 with the controller that includes the representative software stack. The transaction function devices in the exemplary arrangement include a card reader 238. Another transaction function device of the exemplary arrangement includes an encrypting PIN pad 240. A thumbprint reader 242 which is an input device usable to receive identifying inputs from users is also included in this exemplary arrangement. As schematically represented each of the devices 238, 240 and 242 include one or more circuits which have respective processors and data stores. The circuits are capable of carrying out computer executable instructions stored in their respective data stores to enable these devices to not only carry out functions but also to provide security features in a manner hereinafter discussed.

Another exemplary transaction function device that is included in this automated banking machine is a check scanner 244. Check scanner 244 operates to produce images of financial checks that are received through the check scanner. The check scanner also includes circuitry which includes at least one processor and at least one data store as schematically represented. Check scanners and other devices used in exemplary arrangements may include features like those described in U.S. Pat. Nos. 8,418,916; 7,922,098; 7,837,096; 7,815,104; and/or 7,595,816 the disclosures of each of which are incorporated herein by reference in their entirety. In addition numerous other types of devices generally referred to as 246 may be included in the machine. Devices 246 may be of the types previously described such as displays, portals, output devices, input devices, sensing devices or other types of devices that may be included in the machine. Of course additional or different devices may be included in various embodiments.

Shown in FIG. 19, the software components referred to in FIG. 18 are executed in a controller 248 of the exemplary machine. The controller includes one or more circuits that include one or more data stores schematically indicated 250. Data store 250 of the exemplary embodiment may include a processor controlled hard drive or other suitable data storage unit that is controlled through operation of at least one associated processor. The control circuitry of the exemplary embodiment further includes at least one processor schematically indicated 252. The processor 252 may include an Intel iCore processor or other suitable processor that is capable of executing the instructions stored in the at least one data store.

The exemplary controller further includes a trusted platform module (TPM) schematically represented 254. The trusted platform module of the exemplary embodiment operates in accordance with programmed instructions and provides a security device to reduce the risk of unauthorized devices operating in the machine. Further the trusted platform module may also be used to assure that the devices which operate in the machine have not had their software programming modified from documented secure programming conditions. Such changes in software in the devices may result from attempts to conduct exploits on the machine. Further in exemplary arrangements the trusted platform module may operate to provide secure communication between the controller and one or more of the transaction function devices in the machine. Exemplary embodiments may include features like those described in the following U.S. Patents, the disclosures of which are incorporated herein by reference in their entirety: U.S. Pat. Nos. 8,474,698; 8,342,395; 7,988,039; 8,448,850; 7,967,193; 8,100,323; 8,052,048; 8,052,047; 8,038,057; 7,988,039; and 7,229,009. Of course it should be appreciated that although in some exemplary arrangements the trusted platform module is utilized to provide secure communications and secure operation of the controller and the associated devices, in other arrangements other hardware and software may be utilized to accomplish these functions.

In exemplary embodiments the software architecture operates to avoid possible security problems that might otherwise arise due to compliance with the CEN XFS Standards, particularly security vulnerabilities are possible due to the required standardized interface between the application and the device drivers, and which requires that certain data that is received through or produced by the transaction function devices must be presented to the application so that the application can carry out the necessary transaction steps. Presenting the data to the application in the required standard and/or unencrypted format may present issues as criminals may be able to intercept the data within the machine at the standardized interface.

In the exemplary arrangement the devices that are enabled to provide secure communication between the devices and the controllers are operated to prevent the transmission of sensitive data through the XFS device interface. This is accomplished by using substitute data which can then be correlated through operation of the originating device with the actual data that is needed for the transaction. Such actual data may then be sent from the device to the controller in a secure and encrypted manner to avoid the unauthorized interception thereof.

In exemplary arrangements a card reader may read card data from the magnetic stripe of a user card. Alternatively or in addition the card reader may operate to read data from a chip of a smart card. This may be done via electrical contacts or via wireless communications. Such data read through operation of the card reader may be caused to be stored in accordance with the programming of the processor associated with the circuitry of the card reader in the at least one data store of the circuitry. In some exemplary arrangements the circuitry of the card reader may operate to cause the card data and/or chip data to be stored in an encrypted manner.

Responsive to the programming of the circuitry of the card reader, instead of sending the card and/or chip data to the XFS interface software layer, the card reader operates to produce substitute data that can be correlated through operation of the circuitry in the card reader with the actual read data from the card. Substitute data produced by the card reader may then be utilized and passed through the XFS interface to the application. The application may be configured to operate to then securely recover the actual card data at an appropriate place in the transaction steps when such data is needed. Alternatively in some arrangements the security software included with the software installed on the machine may operate to determine when the card data is needed and take the necessary steps to cause communication with the card reader to recover the actual data. In the exemplary arrangement when the application calls for the card data, the at least one controller operates in accordance with its programming to communicate securely with the control circuitry in the card reader 238. The application and/or the security software communicates the substitute data to the card reader that then operates in accordance with its programming to recover the actual card data. Such card data can then be recovered from the data store in the card reader and transmitted in a secure and encrypted manner to the application layer or the security layer where the actual card data needed for carrying out the transaction is resolved and utilized for purposes of further carrying out the transaction steps. As can be appreciated, this approach avoids passing the card and/or chip data in a clear and unencrypted manner through the XFS interface.

Similar approaches may be utilized with certain secure input devices such as the exemplary thumbprint reader 242. Again the thumbprint reader may operate in accordance with its programmed control circuitry to provide data that is a substitute for the actual data which is read from the user's thumbprint. Instead the substitute data is utilized by the thumbprint reader to recover the actual data. The controller operates in accordance with the software programming to transfer the substitute data through the XFS software interface to the software application. Again the security related software for the application operates to cause communication with the thumbprint reader so that when the actual data is needed, secure communication of the substitute data is sent to the thumbprint reader. The thumbprint reader then recovers the actual data and transmits it in a secure and encrypted manner to the application which then may utilize it for purposes of carrying out the transaction.

Other exemplary embodiments may include secure operation of the check scanner. The check scanner produces images of checks that are received through operation of the machine. These checks include private data such as the check writer's account number, the check writer's name and address and other information that may present privacy concerns. In exemplary arrangements to minimize the risks associated with transmitting this data and/or images in the clear through a standardized interface, substitute data is generated through operation of the circuitry in the check scanner. The substitute data is then correlated with stored data in the data store of the check scanner. Again as with the other examples the substitute data is processed and passed through the software layers. The substitute data is utilized until the actual data is needed by the application. At the point in the transaction where the actual data is required, secure communication of the substitute data to the check scanner is made. The substitute data is then utilized to recover the actual data which is then sent in an encrypted and secure format to the application. The application can then use this data for purposes of processing the transactions in a manner like that described in the incorporated disclosures. As can be appreciated, numerous applications of these approaches may be utilized in exemplary embodiments to avoid having to store or to pass data in the clear between software applications at the XFS interface. Thus the exemplary embodiment enables the configuration of software architectures in machines in accordance with the XFS standards or other suitable standards but avoids the possible security risks that compliance with such standards may impose. Of course it should be understood that the principles may be utilized in various types of automated banking machine environments to help in providing enhanced security.

Figure 20:
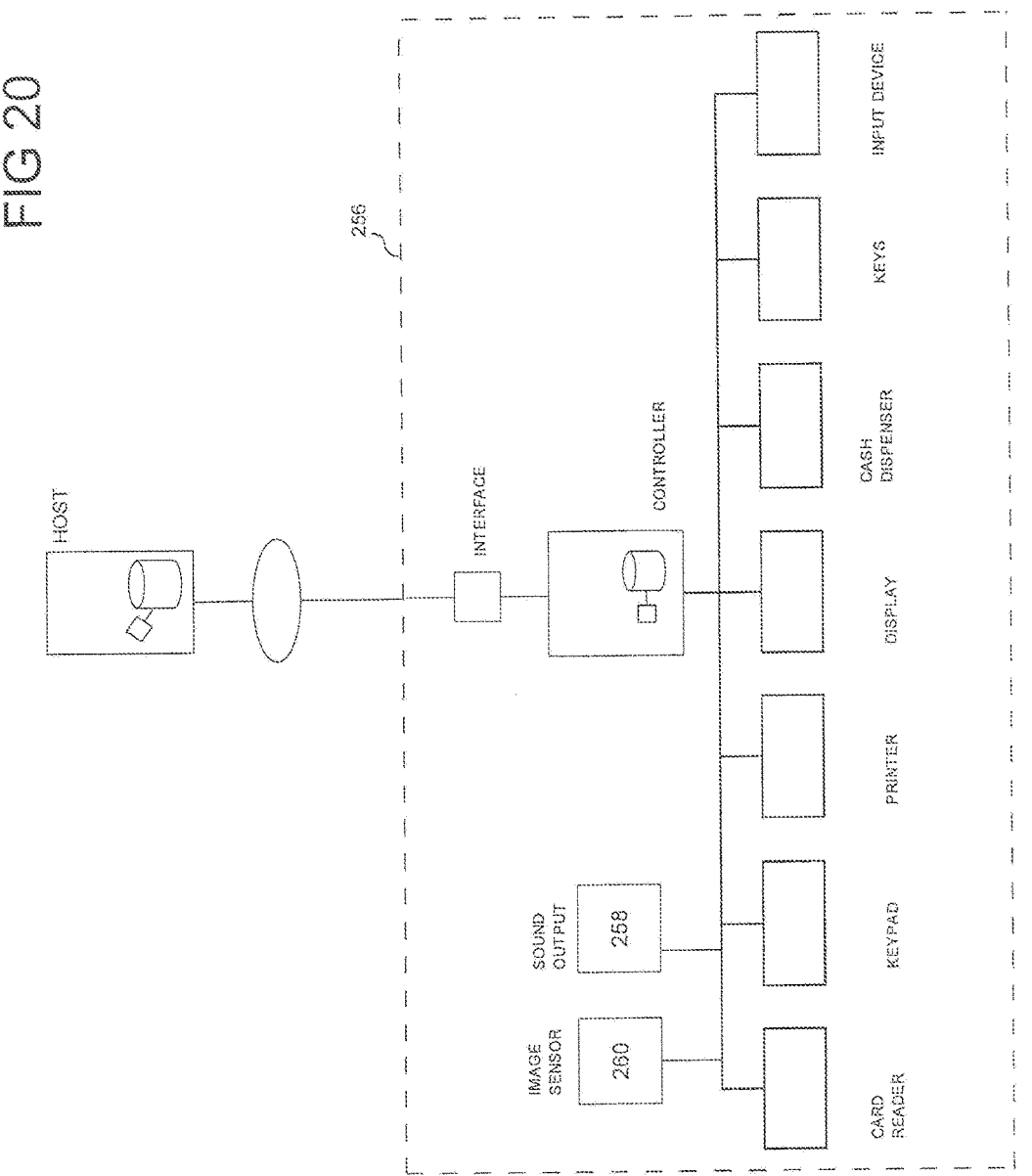
FIG. 20 is a schematic view of components included in an exemplary alternative automated banking machine that has a user interface that facilitates operation by blind or sight impaired users.

FIG. 20 shows yet a further alternative embodiment of an automated banking machine generally indicated 256. Automated banking machine 256 may include devices of the types previously described and may operate in a manner similar to that described in connection with automated banking machine 12 except as hereinafter specifically discussed. Automated banking machine 256 includes improved capabilities for operation of the machine by users that are blind or that have impaired vision. In order to facilitate the operation of the machine by blind or other disabled users, the exemplary machine 256 includes at least one sound output device schematically indicated 258. Sound output device 258 may include devices that are usable to produce audible outputs corresponding to instructions for operation of the machine. Such sound outputs may include in some exemplary embodiments a headphone jack, audio speakers, wireless transmitter or other suitable devices for providing signals which can be directly or indirectly audibly perceived by users and which instruct the user in how to operate the particular machine in the absence of the ability to visually see the output or input devices of the machine. Exemplary machines may include features like those described in the following U.S. Patents, the disclosures of which are each incorporated herein by reference in their entirety: U.S. Pat. Nos. 8,308,057; 8,393,534; 8,469,266; and/or 7,988,041.

The exemplary automated banking machine further includes a user interface having an imaging sensor schematically indicated 260. In exemplary embodiments the imaging sensor 260 may include an active pixel sensor which is operative in accordance with its programming to capture numerous images of adjacent structures in rapid succession so as to determine the direction of movement of an adjacent object. Such imaging sensors may include photo diodes or complementary metal oxide semiconductor (CMOS) sensors that are operative to detect movement of an adjacent structure. Such imaging sensors and related circuitry which are used in optical computer mice, cameras and other types of devices may be operative to analyze the successive images that are captured from an object and to compare the relative movement between successive images. This enables determining the amount and direction of movement of the adjacent object. This enables providing selected types of inputs to the machine through the detected movement by the imaging sensor. Of course it should be understood that while only one imaging sensor is discussed, multiple imaging sensors may also be utilized for purposes of determining movement and resolving inputs.

Figure 21:
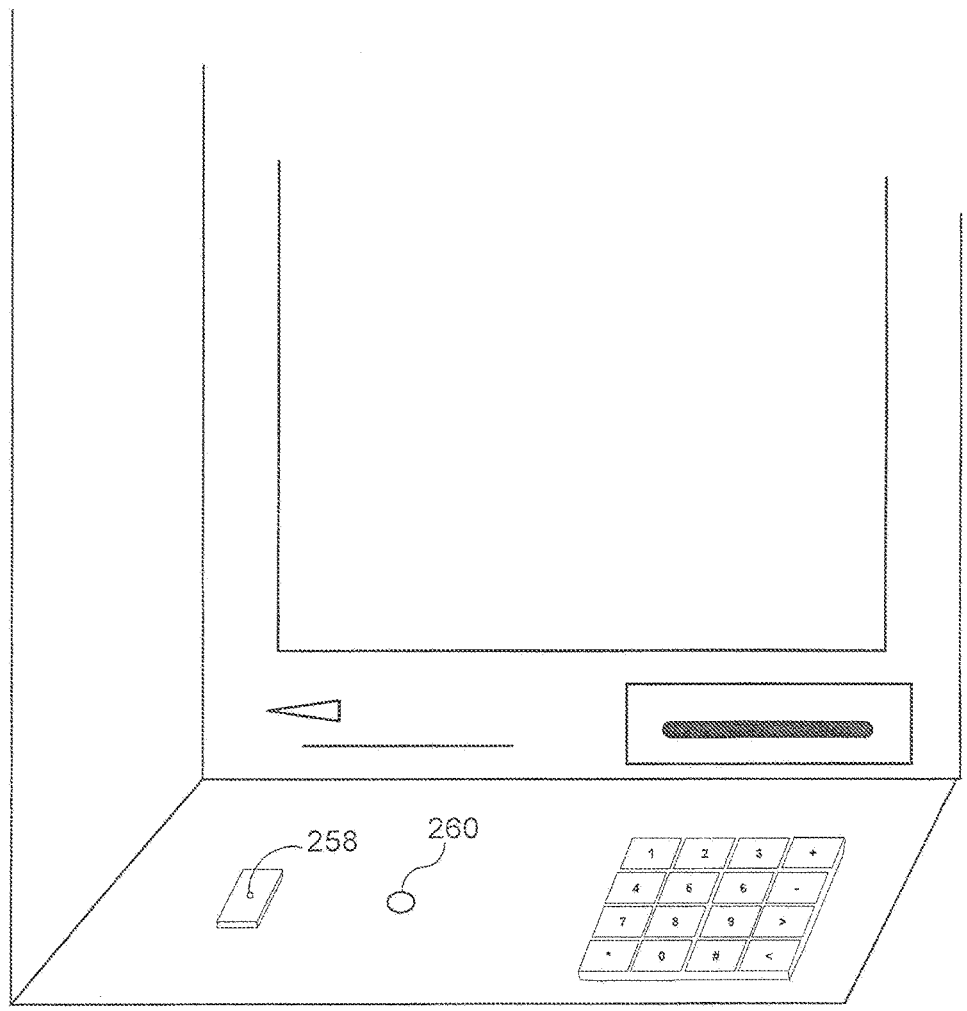
FIGS. 21-23 show different alternative user interface arrangements for an automated banking machine of the type shown in FIG. 20.

In the exemplary arrangement, the one or more imaging sensors 250 is utilized to detect movement of a machine user's body part such as a hand, finger or other body surface to provide inputs to the machine. For example as represented in FIG. 21, the imaging sensor 260 may be placed adjacent to the keypad or other input devices of the machine. As represented in FIG. 21, the user interface of the automated banking machine includes a sound output device in the form of a headphone jack. In the exemplary embodiment the at least one controller operates in accordance with its programming to provide output instructions to the user and to receive inputs based on movement of a user's hand adjacent to the imaging sensor.

For example in the exemplary arrangement shown in FIG. 21, the controller may operate in accordance with its programming and a suitable interface circuit to detect the insertion of a headphone connector into the headphone jack 258. Responsive to detecting this connection, the controller may provide outputs that produce audible signals in the headphones that advise the user to move their hand in an area of the machine to the right of the headphone jack. The exemplary controller may then operate in accordance with its programmed instructions to produce audible outputs that advise the user to move their hand to the right if they wish to increase headphone volume or to the left if they wish to decrease volume. The controller may then sense movement of the user's hand to the right or the left through operation of the imaging sensor 260 and cause the associated circuitry to adjust the volume output accordingly.

In an exemplary arrangement the user may then be instructed to move their hand in a direction away from the machine if the wish to blank the display of the machine during their transaction. The controller upon sensing through operation of the imaging sensor that the user has moved their hand in a direction away from the machine, operates to cause the display to go blank or otherwise display indicia that is not related to the user's transaction. If the user's hand is not sensed as moving away from the machine, the display continues to operate in a manner similar to that utilized when the machine is operated by users with normal vision.

In the exemplary arrangement the controller may operate in accordance with its programming to then provide audible outputs to the user indicating that the card accepting slot is positioned approximately ten inches to the right, and two inches above where the user's hand is currently sensed. The user may then move their hand to the card reader slot and input their card. The controller then operates in accordance with its programming to sense that the card has been inserted and then operate the card reader to read the data from the user's card.

Upon determining that the user's card has been read, the controller may operate in accordance with its programming to indicate to the user that they can input their PIN number through a keypad that is located eight inches to the right of the headphone jack. The user may then locate the keys on the keypad to provide their PIN input. Generally one or more keys of the keypad may include an indicator so that the user can locate a particular key. For example in some arrangements the "5" key of the keypad may include a raised dimple which facilitates a blind user finding the central 5 key of the keypad. The user may then input their PIN in this manner.

Alternatively in some arrangements the programming of the controller may cause audible outputs that instruct the user to move their hand in certain ways to provide a selected PIN input. For example the controller may operate to advise the user to move their hand in the area of the sensor to the left and then to the right to start audible outputs corresponding to a series of digits. The user may be instructed to move their hand toward the machine when they hear a digit that they wish to input. The controller may then operate in accordance with its programming to provide audible outputs of the series of numerals until the user moves their hand in the manner which indicates that they have selected that particular output digit. The user may then be advised that they have selected the particular digit and to move their hand in a certain way if they would like to select a second digit by having the machine output a series of numerals and to again move their hand in a particular way when they want to select a second digit of their PIN. This process may be repeated until the user has provided all of their PIN digit inputs. Of course it should be understood that this approach is exemplary and in other embodiments, other approaches may be used.

In exemplary arrangements the controller may then operate in accordance with its programming to provide audible outputs to the user to have them select a particular type of transaction. This may be done in some arrangements such as those described in the incorporated disclosures by having the user provide inputs through the keypad. In this manner the user may select the type of transaction they wish to conduct in the machine. For example the user may provide key inputs to select balance inquiry, a cash withdrawal, a deposit transaction, a check accepting transaction or other transactions that are available through operation of the machine. The user can then provide the appropriate key inputs to select their desired transaction.

Alternatively in some embodiments the controller 176 may operate in accordance with its associated programming to instruct the user to move their hand in certain ways adjacent to the imaging sensor to make selections. For example the user may be instructed to move their hand to the left to select a balance inquiry and to the right to select a cash withdrawal. A user may be further instructed to move their hand toward the machine to select a deposit transaction and away from the machine to select a check cashing transaction. Further for additional transactions, additional types of movements or series of movements may be indicated through audible instructions to the user so that the user may select their transaction by moving their hand a certain way or thorough a series of movements. After the controller has determined that the user has moved their hand a certain way, the user may be given the option to indicate that they agree that that is their selected transaction by moving their hand one way, or to reset and select a different transaction by moving their hand an opposite way. Of course these approaches are exemplary.

In exemplary embodiments the user once they have selected a transaction type, is instructed to enter an amount associated with the transaction. For example in cases of cash withdrawal, the user may be instructed to enter the amount of cash they wish to receive through the keypad. The user may be instructed in the manner of the incorporated disclosures to provide their input amount through the keypad and then provide a further input confirming the amount. Alternatively the user may be instructed to provide an input through the keypad the amount associated with a deposit, a check cashing transaction or other transaction that involves a financial transfer. Audible outputs produced through operation of the exemplary controller may advise the user of the selected input and ask them to provide a further input to confirm the amount selected.

Alternatively in other arrangements the controller may operate in accordance with its programming to cause audible outputs to be presented that enable the user to select an amount associated with their transaction through hand movements adjacent to the imaging sensor. For example the audible outputs may instruct the user to move their hand a certain way to indicate the first digit of the amount that they wish to receive. As the user moves their hand in the particular direction instructed, the amount may increment to the desired first digit. When the user stops moving their hand, the machine controller may operate in accordance with its programming to indicate that the user has selected the first digit. Thereafter the controller may operate in accordance with its programming to instruct the user to select a second digit. The controller may operate in this manner until the user has selected all of the digits of their selected transaction through hand movements. Further once the digits have been selected, the controller may prompt the user to move their hand adjacent to the imaging sensor in a certain way to confirm the amount that they have selected. In exemplary embodiments the controller may operate in accordance with its programming after it has received the necessary transaction data to instruct the user to provide at least one input which is indicative that the user wants to proceed with the transaction. The controller may operate in accordance with its programming to indicate the transaction type and amount that the user has selected. The user may then be instructed to provide a particular input to confirm the transaction should proceed. This may be done for example by the user providing at least one input through an input device such as the keypad. Alternatively the at least one controller may operate to advise the user to move their hand in a certain way adjacent to the imaging sensor in order to indicate that they wish to proceed with the transaction.

Once the user has provided the confirming input, the automated banking machine operates to then provide the particular transaction functions through operation of the devices. For example if a user has requested a cash withdrawal transaction, the controller operates the cash dispenser to make the cash available to the user. The controller then operates to indicate through audible outputs to the user where to place their hand to take the cash. For example the controller may indicate to the user that they may take the cash through the cash dispensing slot that is located six inches to the right and five inches below the headphone jack.

In exemplary arrangements the controller may then operate after the user has taken their cash to ask whether they wish to conduct another transaction or end the session. Again in exemplary embodiments the controller may operate in accordance with its programming to accept inputs either through the keypad or other input devices or by sensing hand movements through the imaging sensor. If a user requests another transaction, the controller may operate in accordance with its programming to instruct the user how to provide the inputs to identify the transaction type and the amount. Alternatively if the user wishes to terminate the transaction session, the controller will provide audible outputs to indicate to the user where to position their hand to take their card, printed receipt and to perform other actions the user should take. As can be appreciated, exemplary embodiments may enable the operation of the machine through use of keypads or alternatively imaging sensors of the type described. In this way users who wish to utilize hand movements to provide inputs may do so. An advantage of utilizing hand movements for providing machine inputs is that the user does not touch the keys of the keypad. This helps to avoid the risk of unauthorized persons intercepting the user's confidential PIN or other inputs. Further utilizing the imaging sensor to receive inputs also helps to reduce the risk that unauthorized persons can determine the type and amount of transaction that a blind user may be requesting at the automated banking machine. Additional benefits may be obtained depending on the particular type of transaction involved.

Figure 22:
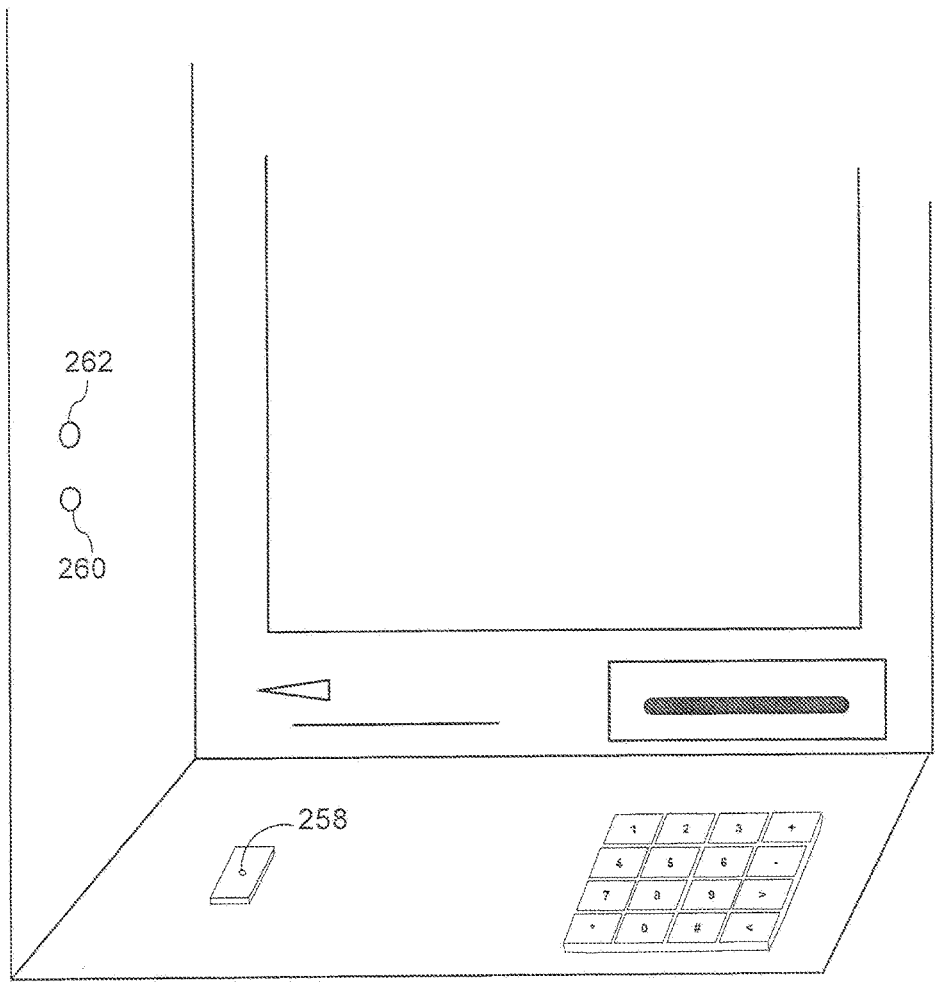

Other exemplary arrangements utilizing imaging sensors are represented by the alternative automated banking machine user interface represented in FIG. 22. In this alternative arrangement an imaging sensor 260 is positioned on a side surface which extends generally outward from the fascia of the automated banking machine. A speaker opening 262 is positioned adjacent to the imaging sensor 260. The speaker opening is associated with an audio speaker that produces outputs that can be perceived by a user by placing their ear in generally close proximity with the speaker opening.

This exemplary arrangement may be utilized to enable a user to operate the machine through voice guidance without the need for having a headphone connector. In this exemplary arrangement the user may place their ear in generally close relation with the speaker opening 262. Instructions provided responsive to operation of the controller may instruct the user to move their head in certain ways so as to provide inputs, select transaction types and to select amounts. By the user moving their head in the user desired manner, various inputs may be provided to the machine. In exemplary arrangements the user's ear may be positioned in generally close proximity to the speaker opening. The risk of interception of any of the audible outputs to the user may be reduced to the same level as would be achieved through the use of headphones. Further in this exemplary arrangement the user could avoid generally having contact with keys or other input devices of the machine in order to achieve operation.

Figure 23:
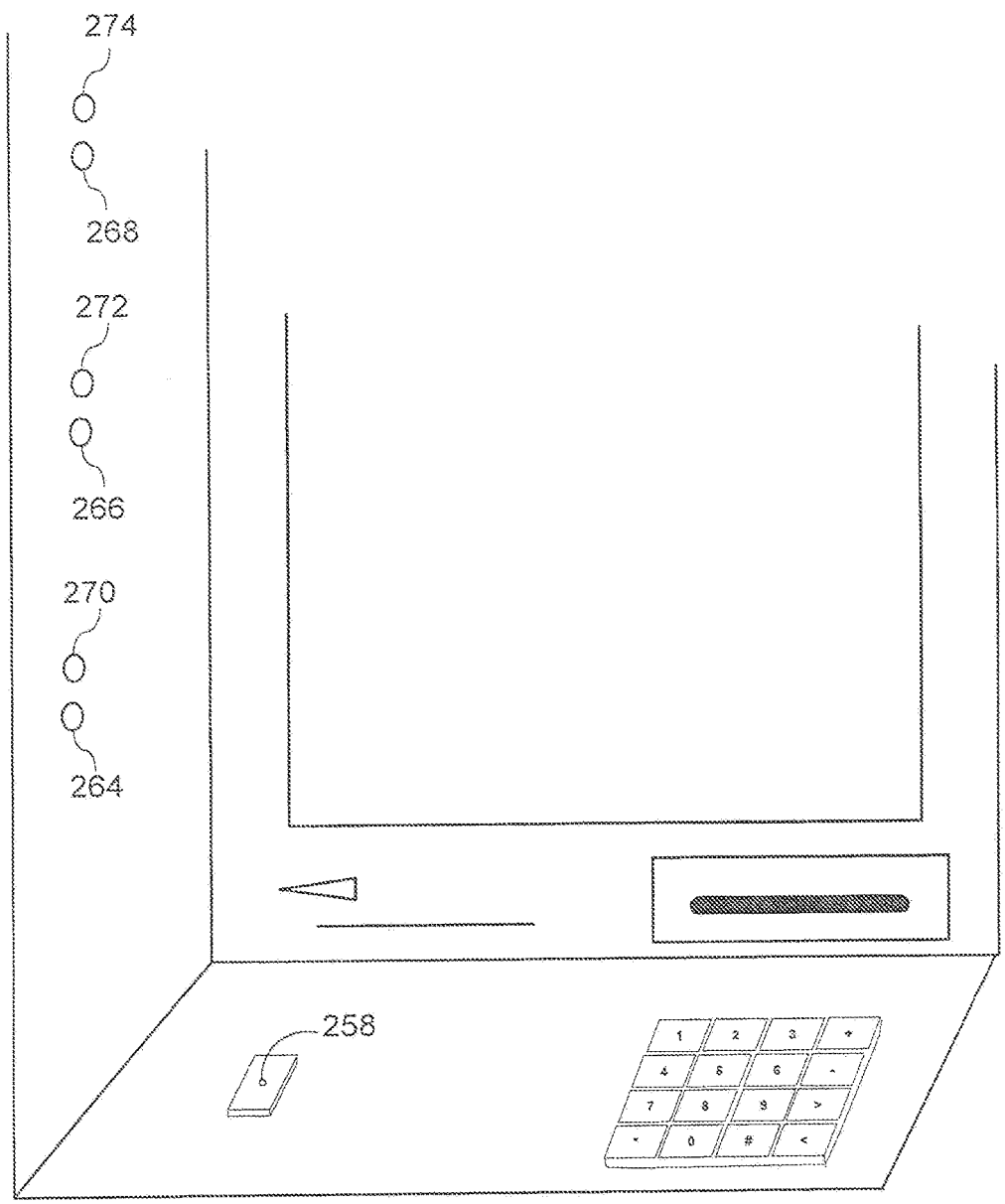

A further alternative arrangement is represented by the automated banking machine fascia shown in FIG. 23. In this exemplary arrangement three spaced imaging sensors 264, 266 and 268 are arranged in various positions of an outward vertically extending fascia wall of the machine. Each of the imaging sensors is associated with a respective adjacent speaker opening 270, 272 and 274.

As with the previously described arrangement this exemplary arrangement is configured to provide audible instructions through the speaker openings and to receive user inputs responsive to movement of the user's adjacent head or ear by an imaging sensor. In this exemplary arrangement by having multiple spaced imaging sensors and speaker openings, users of various stature may operate the machine by placing their head and ear adjacent to the sensor and speaker opening that is the most convenient for them. The exemplary controller may operate in accordance with its programming to sense the user's ear in proximity to the selected one of the imaging sensors and to provide the audible outputs through the associated speaker opening. In some exemplary arrangements the other speaker openings operate to provide masking sounds while the selected speaker opening is providing audible instructions so as to reduce the risk of unauthorized reception of instructions to the user. As with the other described arrangements the user may provide inputs including PIN data, transaction selection data, amounts and confirming inputs through movement in response to audible prompts that are generated through operation of the controller. Such a configuration may enable numerous different types of users to operate the machine in a suitable secure manner. Of course it should be understood that these arrangements of imaging sensors and audio output devices are exemplary and in other embodiments other approaches and arrangements may be used.

Figure 28:
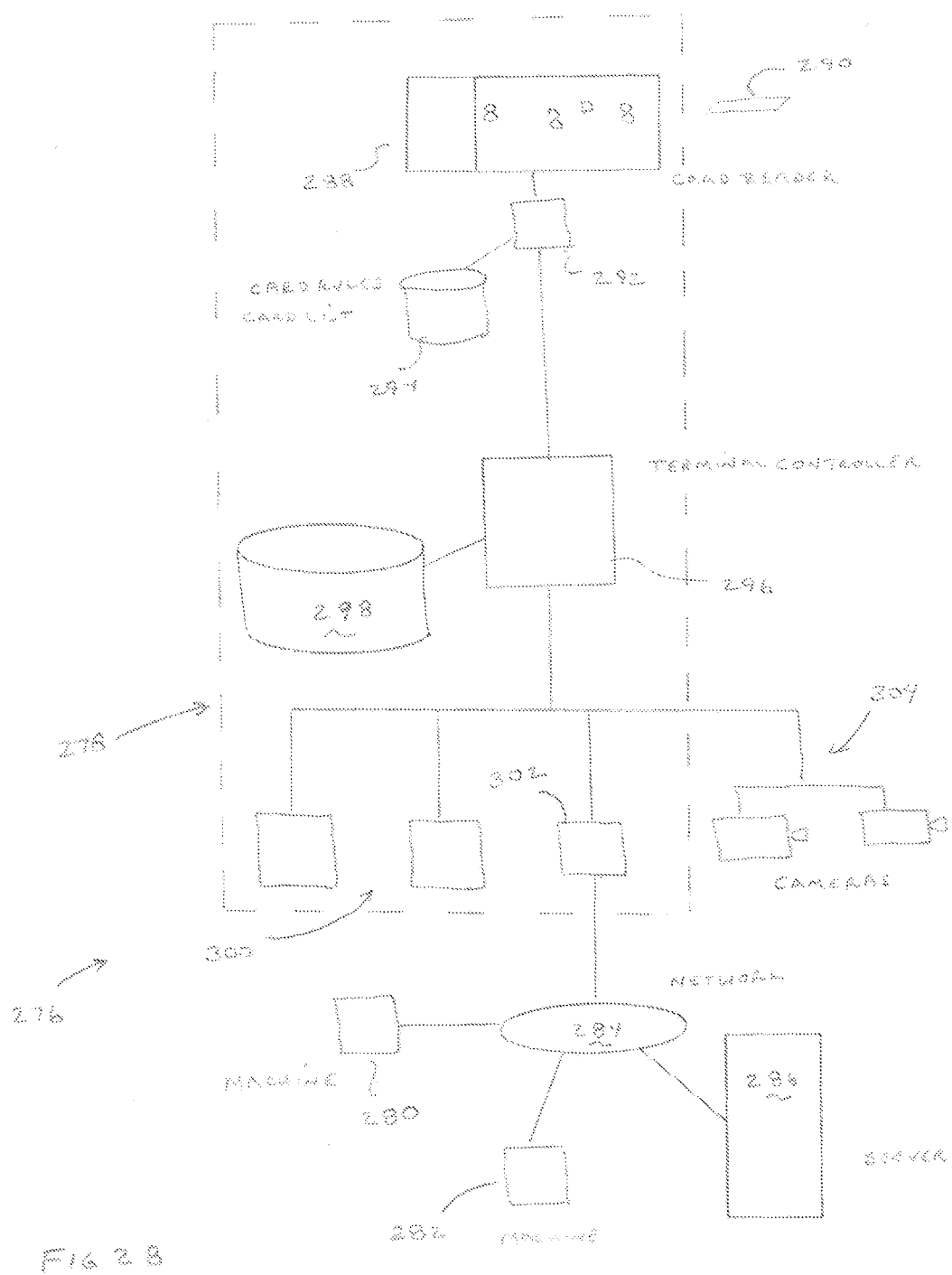
FIG. 28 is a schematic view showing a system that operates to identify activities that may correspond to installation of a card skimming device on an automated banking machine.

FIG. 28 is a schematic view of an alternative automated banking machine and system which operates to identify circumstances which correspond to installation of a card skimming device or other illegal interception device on the automated banking machine. The system 276 includes automated banking machines 278, 280 and 282. The machines are in operative connection with one or more networks 284. The one or more networks are in operative communication with one or more remote computers such as servers schematically indicated 286. Communications between the automated banking machines and the servers are operative to cause financial transfers in a manner similar to that previously discussed in connection with other embodiments.

Automated banking machine 278 includes a reader 288. Reader 288 may include a contact or contactless card reader or other suitable reading device for reading data bearing records. Records from which data corresponding to financial accounts may be read are schematically represented by a card 290. Exemplary reader 288 includes or is in operative connection with at least one microprocessor 292 which is in operative connection with at least one data store 294.

Automated banking machine 278 further includes a terminal controller 296 which may be similar to the terminal controllers previously discussed. The terminal controller is in operative connection with one or more data stores 298 which data store is operative to hold executable instructions, data and other information used by the machine in connection with carrying out transactions.

The exemplary machine further includes transaction function devices generally referred to as 300. The transaction function devices may include devices such as those previously discussed which are suited to carrying out the transaction types for which the machine is adapted. Such devices may include cash acceptors, check acceptors, cash dispensers, input devices, output devices, wireless communication devices and other devices suitable for carrying out transactions. The exemplary automated banking machine further includes an interface 302 which is suitable for communicating with the network or other connected systems. The exemplary machine further is in operative connection with image capture devices 304 which may include cameras or other systems which are suitable for capturing images or other data in response to instructions from the terminal controller.

In the exemplary embodiment the automated banking machine is operative to identify conditions which likely correspond to attempts to install an unauthorized card reading device on or in connection with the reader 288 of the machine. A criminal's attempt to install such a unauthorized reading device may utilize a card type that is not suitable for conducting transactions with the automated banking machine, to test whether the unauthorized device interferes with the operation of the card reader and to determine that data read from the card can be accurately captured via the illegal device. In many circumstances the card would be inserted into the card reader one or more times to accomplish this testing. Further if the card is operatively engaged with the reader for purposes of criminal testing activities, the criminal will not generally attempt a transaction using the card. As a result often the programming of the terminal controller will not result in any messages being sent to the network in connection with the criminal testing activity because no transaction is requested.

Figure 29:
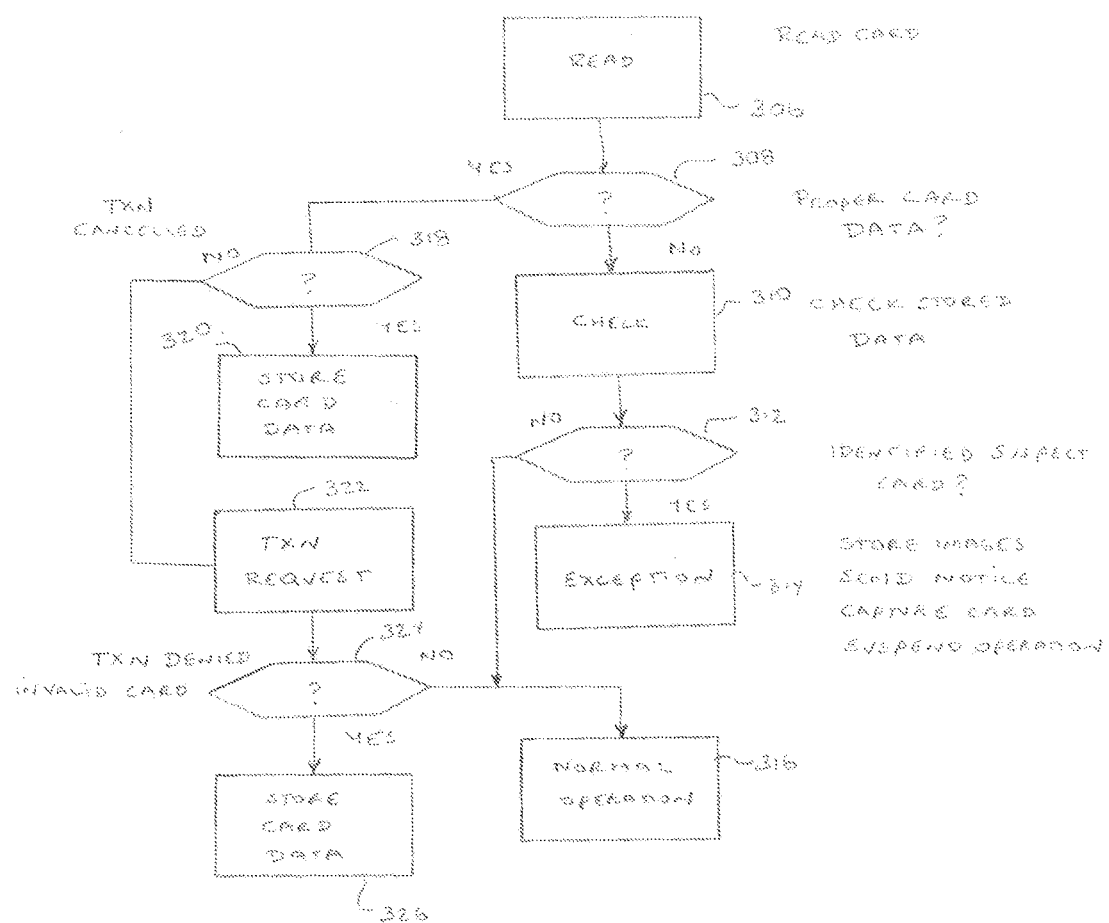
FIG. 29 is a schematic representation of program logic carried out by at least one processor identifying possible installation of a skimming device.

In the exemplary arrangement provisions are made so that card reading activity that may correspond to such criminal testing is identified. The exemplary program logic flow associated with an embodiment of such a system is shown in FIG. 29. The exemplary program logic flow may be carried out by the microprocessor 292 associated with the card reader, the terminal controller 296 or may be shared between the two components.

In the exemplary arrangement the reader 288 operates to accept and read a card. This is represented by a step 306. The card reader 288 operates to read the data from the card. As can be appreciated, the data read from the card is indicative of whether the card is a financial card such as a credit or debit card or an alternative type of card such as a credit card size non-financial card. These cards may include library cards, transit cards, insurance cards, loyalty program cards and the like. In the exemplary embodiment in a step 308 microprocessor 292 determines if the card data corresponds to what is proper for a financial transaction. This may include analysis of the types of data available from the card. In exemplary arrangements the microprocessor 292 determines whether the card presented is a proper card type based on data stored in the data store 294. If the card data does not correspond to the type of card that could be used to carry out a transaction through operation of the machine, a check is conducted in the step 310 on whether the card data that has been read corresponds to suspect cards that have been previously been identified as possibly being used by criminals to test the installation of unauthorized interception devices. If a card is not identified as a previously suspected card in step 312, the microprocessor 292 sends a message to cause the machine to carry out normal operation as reflected in step 316.

If the card is identified as one that has already been identified as suspect in a step 312, the microprocessor 292 operates to send a notice to the terminal controller 396 which operates in accordance with its programming to carry out steps that are appropriate for purposes of responding to the probable criminal activity. This is represented in a step 314. In such circumstances, the terminal controller 296 may operate to cause the image capture devices 304 to capture images of the individuals who may be attempting to use such an improper card in the machine. In addition, the terminal controller may operate in accordance with its programming to send a notice through the network 284 to one or more servers 286 or other appropriate computers to indicate the probable criminal activity. Such notices may then be responded to by notifying security personnel or other appropriate individuals to proceed to the machine to investigate a possible criminal activity. Alternatively or in addition, the terminal controller may operate to capture the card, suspend operation of the machine and also take other steps as may be appropriate based on the programming of the terminal controller. It should be understood that these steps are exemplary and in other arrangements, other or different steps may be taken.

Alternatively if in step 308 the card data read through operation of the reader is determined to correspond to a proper card type that can be used with the machine, the microprocessor 292 in conjunction with the terminal controller 296 are operative at a step 218 to determine if the user cancelled the transaction. This is represented in step 318. Cancelling the transaction may often correspond to the criminal testing the movement of the card and for communication of card data from the unauthorized card reader. If the transaction is cancelled, the card data is stored through operation of the microprocessor 292 in data store 294. This is represented in a step 320.

If the automated banking machine is not operated to cancel the transaction, the terminal controller operates in the usual manner to submit a transaction request as represented in step 322. As can be appreciated, the transaction request will be routed through the one or more networks 284 to the appropriate remote server 286 that will either authorize or deny the transaction. One or more messages is then returned by the server to indicate if the transaction is authorized. If the message returned through the network indicates that the transaction is denied due to an invalid card, the terminal controller 296 and microprocessor 292 identify this condition as represented in a step 324. The machine then operates in accordance with its programming to store the card data in the data store 294 as represented in a step 326.

In exemplary arrangements the terminal controller 296 operates on a periodic basis or in response to messages received through the network to send updates concerning the card data associated with suspect cards that have been attempted to be used in the machine. Data corresponding to suspect cards is then sent from the machine to one or more remote servers. The one or more remote servers may then operate in accordance with their programming to cause the data concerning suspect cards to be distributed to other automated banking machines such as machines 280 and 282 in FIG. 28 so that all the machines have the updated suspect card data. This way if attempts are detected to use the same card for purposes of testing a skimmer device or other similar interception device at another one of the automated banking machines, this condition may be detected.

Further in exemplary arrangements, the remote server may also analyze the data to see if the same suspect card data has been presented at multiple machines. Such card data may not only be stored at each of the machines, but may also be associated with a special status so that further steps are taken when such a card is read at a machine. These steps may include, for example, having the machine immediately give notice to law enforcement authorities, security personnel or other entities that need to be notified of illegal activities. Alternatively or in addition in the event that the machine is in a vestibule or other enclosure, the enclosure may be immediately locked so that the criminal within the enclosure cannot escape before law enforcement authorities arrive. Alternative or additional steps may further be taken depending on programming of the automated banking machine and the system in which it is used.

Figure 30:
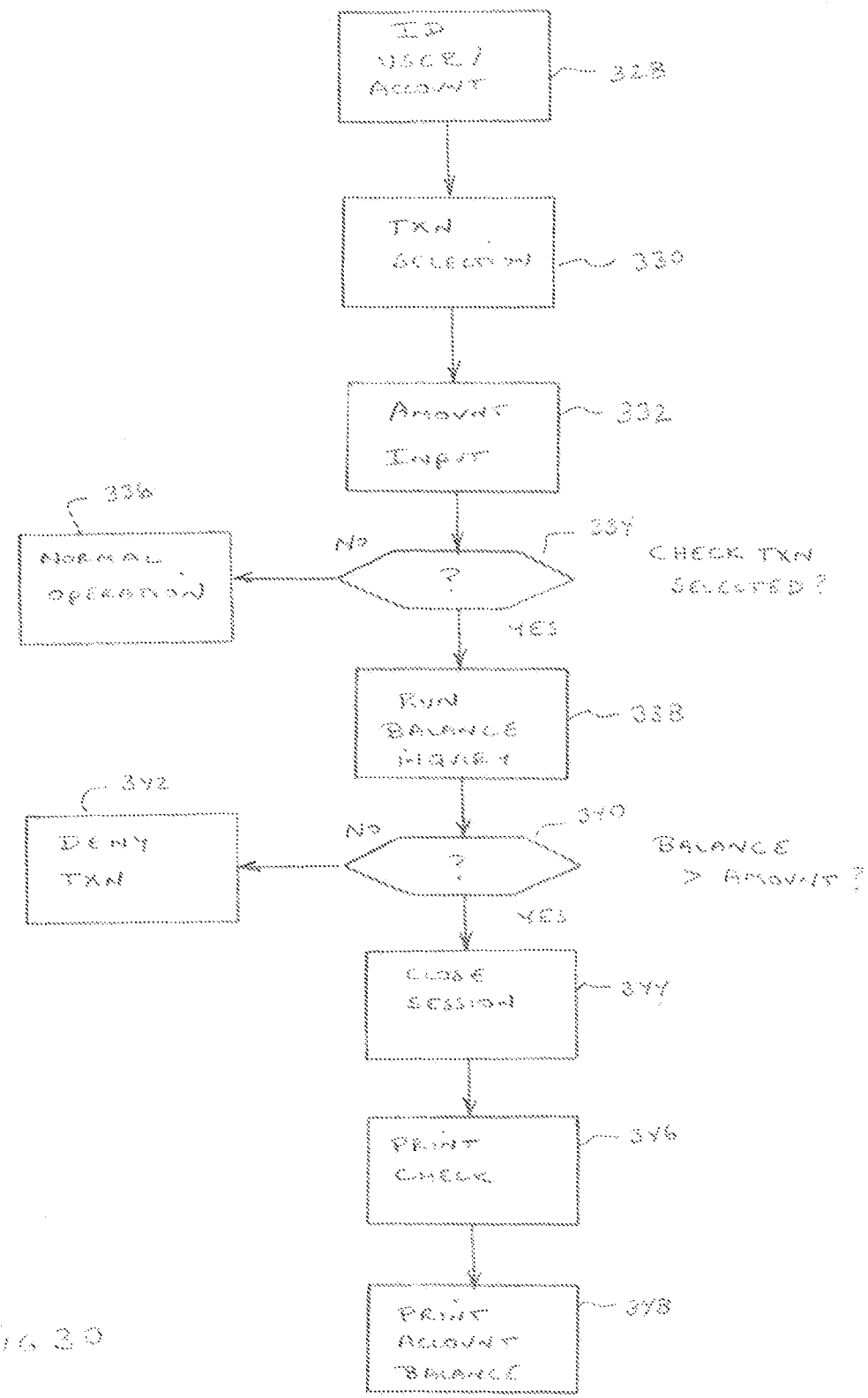
FIG. 30 is a schematic representation of program logic carried out by an automated banking machine that issues financial checks.

FIG. 30 shows a schematic view of program logic carried out through an exemplary automated banking machine that may be similar to those previously described. The exemplary automated banking machine is operative to provide users with financial checks. Such financial checks may include printed paper checks. Alternatively in some arrangements the automated banking machine may be operative to provide electronic representations of checks that can be processed as checks. In still other arrangements, electronic tokens or tangible items may be provided to a user in connection with exemplary transactions.

The exemplary program logic flow which may be carried out by one or more terminal controllers in an automated banking machine may be utilized in circumstances where a merchant or other vendor wishes to provide items of value such as goods, services or cash to a user. Such a system may be employed in some circumstances where the merchant and/or user wishes to avoid the transaction fees that may be associated with withdrawing cash or transferring value via communication with a transaction processing network. As can be appreciated in some arrangements, significant transaction surcharges are applied to cash withdrawal transactions on certain machines. Further certain network rules may cause the liability for fraudulent transactions to shift from an entity issuing a credit or debit card to a person accepting such a card if a transaction is conducted at a device or a system does not include all of the security features that the card issuer has indicated are required in order for the card issuer to have liability. An automated banking machine carrying out transaction logic as represented schematically in FIG. 30 may in some embodiments avoid such a liability shift. Of course it should be understood that these approaches are exemplary and the represented features may be used in other types of systems as well.

In the exemplary arrangement the automated banking machine executes program instructions to receive from a user data bearing records or other information that is suitable to identify the user or an account. This is represented in a step 328. Such activity may include in some arrangements the reading of account identifying data from a user card, the receipt of a PIN number, the reading of biometric data or other data through input devices on the machine so as to identify the user and/or their account. The automated banking machine then operates in accordance with its programming to present the user with transaction selection options, and the user provides a transaction selection input as represented in a step 330. In the exemplary arrangement the user may elect to receive value such as cash or goods or services through the machine by making payment by check. If the user wishes to make such a transaction selection, they may do so by providing the corresponding transaction selection input. The user also is prompted through operation of the machine to indicate the amount associated with their transaction. This is represented in a step 332. In an exemplary arrangement if the user has selected a check transaction, the user will be prompted to provide inputs corresponding to the amount of the check that they wish to have accepted by the merchant or other associated entity.

In a step 334, the terminal controller or other processor operates to determine if a check transaction has been selected by the machine user. If the machine user has not selected a check transaction, and has chosen a cash withdrawal transaction, cash acceptance transaction or other transaction that can be carried out through operation of the machine, the terminal controller operates in accordance with its programming to carry out the transaction steps associated with those other transactions. This is represented in a step 336.

If the user of the automated banking machine has selected a check transaction, the terminal controller operates in accordance with its programming to automatically formulate an account balance inquiry transaction. This account balance inquiry transaction is operative to cause the machine to communicate through one or more associated networks with computers to determine if the account corresponding to the user is valid and also whether the account has a sufficient balance and/or status so as to allow the check transaction in the selected amount to be carried out. In some exemplary arrangements the formatted transaction messages may be comparable to those carried out in response to user inputs making an account balance inquiry to check the amount of money in their account. Alternatively in other arrangements, the formulated transaction inquiry may include messages that inquire as to other features such as whether the account is in good standing, includes overdraft protection, qualifies for cash advances or other information which is appropriate for determining whether the check transaction should be carried out. The nature of the formulated inquiry messages will depend on the nature of the account on which a check has been requested to be drawn. These steps as carried out through operation of the terminal controller and associated networks is represented schematically by step 338.

If the account is determined not to have a sufficient balance or otherwise qualify for writing a check in the amount requested by the user, a determination is made at step 340 that the transaction could not be carried out. The user is so informed as represented in a step 342. This step may include, for example, the terminal controller operating in accordance with its programming to inform the user that the transaction cannot be carried out. Further in some arrangements the terminal controller may operate to return the user's card or otherwise close the transaction.

If in step 340 it is determined that the user's account balance is sufficient for writing a check in the amount, the automated banking machine operates in accordance with its programming to take steps to close the network session which was involved in making the determination. This is represented by step 344. In some arrangements, step 344 may include additional communications between the automated banking machine and other computers in the network such as obtaining appropriate information from the network about the user's account which may be utilized by the automated banking machine in producing a financial check in the amount requested by the user. The information obtained may include data that cannot be derived from the data bearing record such as the user card or other information that the user has input to the machine in connection with requesting the transaction, which information is necessary for purposes of producing the financial check. Alternatively or in addition, the automated banking machine may in step 344, communicate with computers in multiple systems which can derive the data necessary for purposes of producing the check. This may include, for example, obtaining information on bank identification numbers, routing numbers or any other information that may be required to produce the check such as for example, the data that appears in the micr line of a financial check indicating the account and routing data used for processing the check. Of course these approaches are exemplary and the exact approaches used will depend on the particular system.

The terminal controller of the exemplary arrangement then operates in a step 346 to produce a printed financial check in the amount requested by the user. The printed financial check will include the data necessary for processing and may include all of the data normally found on a preprinted check. Alternatively or in addition, the check may include extended micr line data or other data so as to cause the amount of the check to be routed and paid to the account of the merchant or other person who is to receive the amount. Further in the exemplary embodiment the terminal controller operates in a step 348 to print an account balance statement. The account balance statement of the exemplary arrangement may include information such as the user's account data and their account balance. Further in exemplary arrangements, the account balance statement may include information on whether the user account has overdraft protection, certain statuses or other information that may provide the merchant with assurance that they may accept the check. Of course it should be understood that this logic flow is exemplary and in other exemplary arrangements other or alternative approaches and additional or different steps may be utilized.

The printed financial check and account balance statement may be taken by the machine user from the machine and presented to a merchant at a transaction location who can provide value in exchange for the check. In some exemplary arrangements the merchant station may include a terminal or other device for accessing information that enables the merchant to verify that the check has been issued by the machine and that it is unaltered. This may include, for example, a merchant terminal communicating through a local network with the banking machine or through a wide area network with the systems that provided information on the account balance or other authorization to issue the check. The merchant may also physically or electronically review the account balance statement.

In exemplary arrangements if the merchant finds that everything is in order, the merchant may accept the check and provide the user with value for the check in the form of cash, goods or other agreed value. The merchant may then scan the check using a scanner connected to the merchant terminal or other system commonly employed by the merchant to scan received checks issued by the automated banking machine as well as preprinted checks. The merchant may then carry out the necessary steps to have the funds represented by the check deposited in the merchant's account by a financial institution or other financial services provider associated with the merchant's account.

In other exemplary arrangements, the automated banking machine may operate in alternative ways to provide check data or items to a user that the user can exchange for value. For example in some exemplary arrangements, the automated banking machine may operate to securely communicate with a user's portable wireless device. The data communicated to the user's portable device may correspond to a value for an electronic check. For example in some arrangements the data may correspond to a visual image of a check that a user may present on the display of a smart phone to the merchant's system. Alternatively or in addition, the automated banking machine may provide the user with an electronic token or other data which can be stored in the memory of a smart phone and then communicated to the merchant's system in exchange for receiving value. In still other alternative arrangements, the automated banking machine may issue a stored value card or other tangible item which is representative of the value that the user wishes to receive. The tangible item may then be taken to a merchant station and the value transferred in the manner of a check or similar article so the merchant can obtain a deposit of the funds in the merchant's account. The merchant may then provide inputs to a merchant terminal or take other steps to authorize the use of the card. The user can then use the card for purposes of obtaining goods or services from the merchant or other affiliated merchants which accept the card. Of course these approaches are exemplary of many different approaches that may be used.

In some exemplary arrangements the automated banking machine may be operative to cause one or more transaction messages to be communicated which place a hold on the user's account for an amount corresponding to the check. The hold can be maintained for a sufficient period of time to allow the merchant to scan and present the check to a check payment processing system. This may be done in a manner similar to that used for certain credit and debit card transactions where the actual charges that the user will incur are unknown. For example, in some arrangements the hold for the amount could be placed on the user's account for a period of one day and then automatically lifted through operation of the system. This might be done, for example, by having the machine perform in accordance with its programming on a timed basis to submit messages to the network that cause a reversal of the initial hold transaction. Alternatively or in addition, communication with a merchant terminal which would show submission of the check for processing would then cause the automated banking machine to operate so as to send transaction reversal messages that release the hold on the user's account. Further it should be understood that these approaches may be used in connection with the other types of articles or data discussed herein which represent value and which can be received from the machine. Of course these approaches are exemplary and in other arrangements, other approaches may be used.

FIGS. 31-34 show schematically program logic carried out through operation of one or more devices in connection with providing a user with cash or other value from an automated banking machine or other fulfillment point. In this exemplary arrangement the user may request a transaction using a mobile device such as a smart phone or wearable computer of the types previously discussed. The exemplary arrangement is further usable to assist the user in locating a fulfillment point that can complete the user's transaction which involves a transfer of value.

Figure 31:
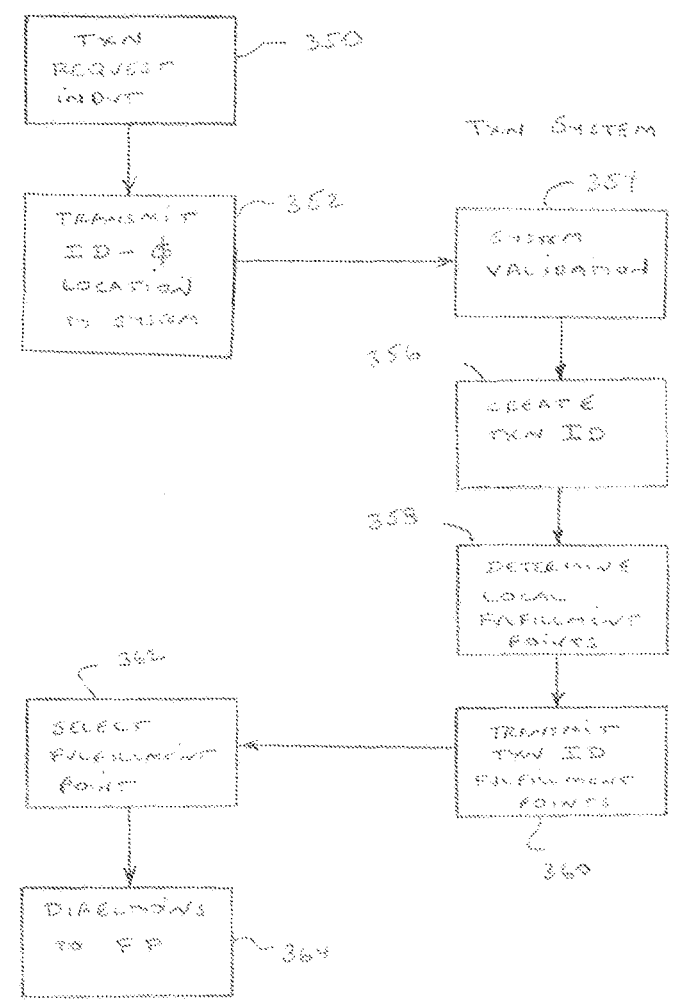
FIGS. 31-34 are a schematic view of program logic carried out in connection with a transaction that involves a wearable computer.

As represented in FIG. 31, a user who desires to receive cash may, for example, provide a transaction request input through an input device associated with a mobile device. The mobile device may include a smart phone which includes a program such as an application for receiving such a transaction request. Alternatively other arrangements may involve a wearable computer, such as in the form of glasses like those previously discussed, wallets, watches or other articles which include programming for receiving such a request. This transaction request is represented by a step 350. In response to receiving the request, the mobile device operates in accordance with its programming to transmit information that is appropriate for purposes of conveying a request for the transaction that the user wishes to conduct to a remote transaction system. For example the mobile device may submit messages including an identifying value associated with the user's account, the amount of value such as cash the user wishes to receive, and data corresponding to the user's current location, to the transaction system. It should be understood that in some exemplary arrangements the account identification may include an account number. Alternatively the identification data may include token data which can be used by the transaction system to derive data corresponding to a user account number or other information that can be associated with a user account. The use of a token instead of an actual account number may be used to enhance security associated with the system. The transmission of the data concerning the user's transaction request to the system from the mobile device is represented in a step 352.

The data transmitted in step 352 along with other data which is transmitted from the mobile device for purposes of requesting the transaction is received in an exemplary arrangement wirelessly by the remote transaction system. The exemplary transaction system includes one or more servers and data stores that are capable of validating the transaction data and carrying out financial transfers. The communications to the transaction system may include communications via cellular phone communications, wireless broadband or other suitable methods for communicating the data between the mobile wireless device and transaction system.

In a step represented 354 the transaction system receives the identifying data and other information from the mobile device. The system then operates in accordance with its programming to validate that the user identification data and other information that is transmitted corresponds to a valid user and/or account which can be used to carry out the transaction as requested by the user. The system 354 operates in accordance with its programming to create a transaction identifier (ID) for the particular transaction is represented in a step 356. The system then further operates in accordance with its programming to determine locations where the user's requested transaction can be fulfilled. In the exemplary embodiment the transaction system uses the location information received from the user to determine the fulfillment points that are in proximity to the user that can complete the transaction the user has requested. This is done based on stored data that the transaction system can access as to the locations of automated banking machines, merchant facilities or other systems that can fulfill the user request. This is represented in a step 358. The transaction system then operates in accordance with its programming to cause to be sent to the mobile device, the resolved transaction ID associated with the requested transaction as well as data corresponding to the fulfillment points that are currently in proximity to the user which can fulfill the transaction. This is represented in a step 360.

The mobile device of the user receives the data from the transaction system including the data corresponding to the fulfillment points that can carry out the requested transaction. The user's mobile device then operates in accordance with its programming to present to the user a user interface that enables the user to provide inputs to select a fulfillment point. This is represented in a step 362. The user's mobile device then operates in accordance with its programming to determine or obtain from a remote system directions from the user's current location to the selected fulfillment point. This may be done based on stored data included in one or more data stores accessible by the mobile device. Alternatively or in addition, such directions may be resolved through communication of the mobile device with remote servers such as Google Maps, MapQuest or other similar service that can provide a user with directions. The presentation of the directions to the user from the mobile device is represented by a step 364.

The user may then travel to the selected fulfillment point. The mobile device may provide turn-by-turn instructions or similar guidance to the user to help them reach the desired fulfillment point. It should be understood that in exemplary arrangements the fulfillment point may include an automated banking machine, a merchant transaction area, a particular facility or other apparatus that can fulfill the user's transaction request. It should be understood that although the exemplary arrangement may be discussed in connection with an automated banking machine, such other devices and systems may be utilized in exemplary arrangements to fulfill transactions.

Figure 32:
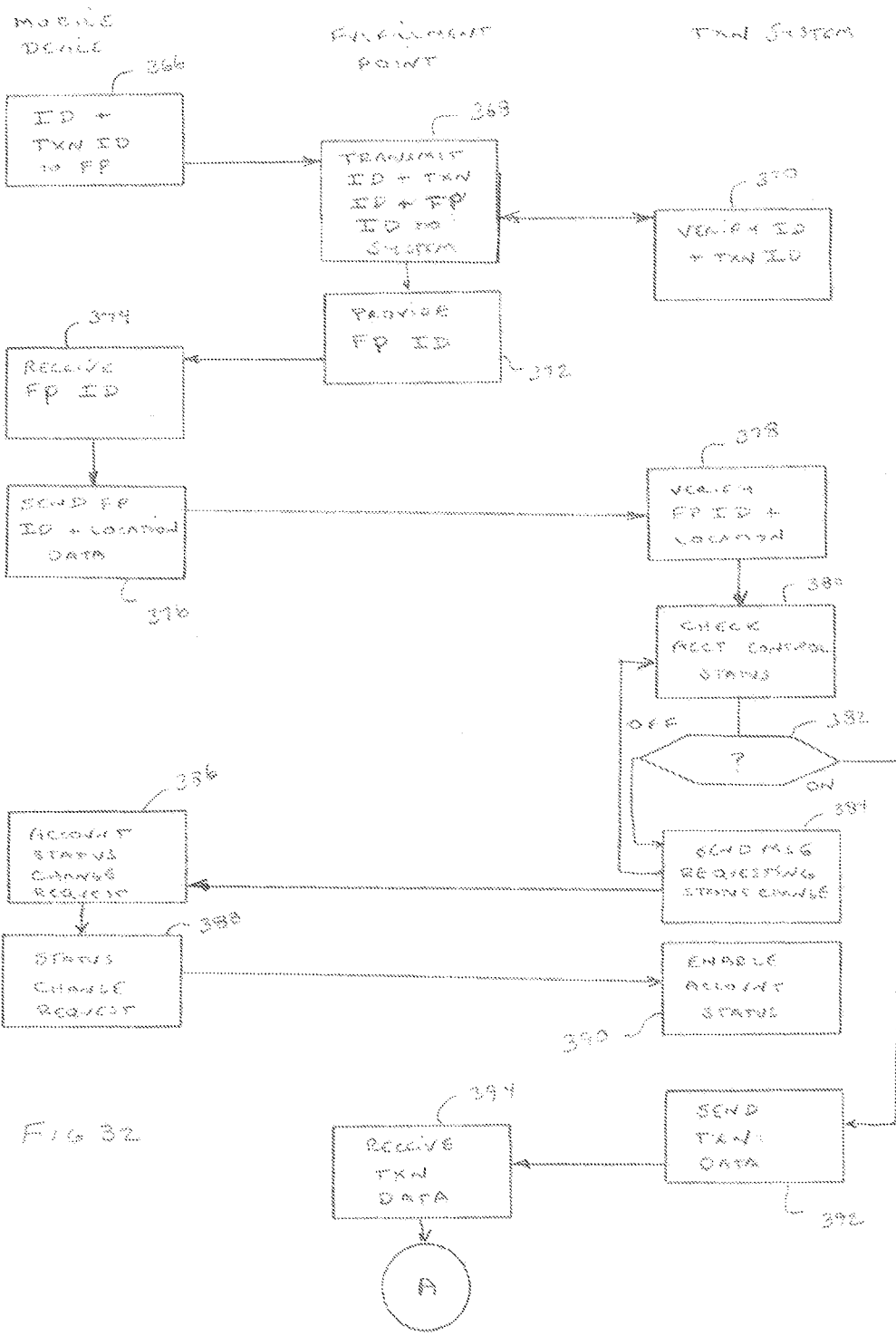
Figure 33:
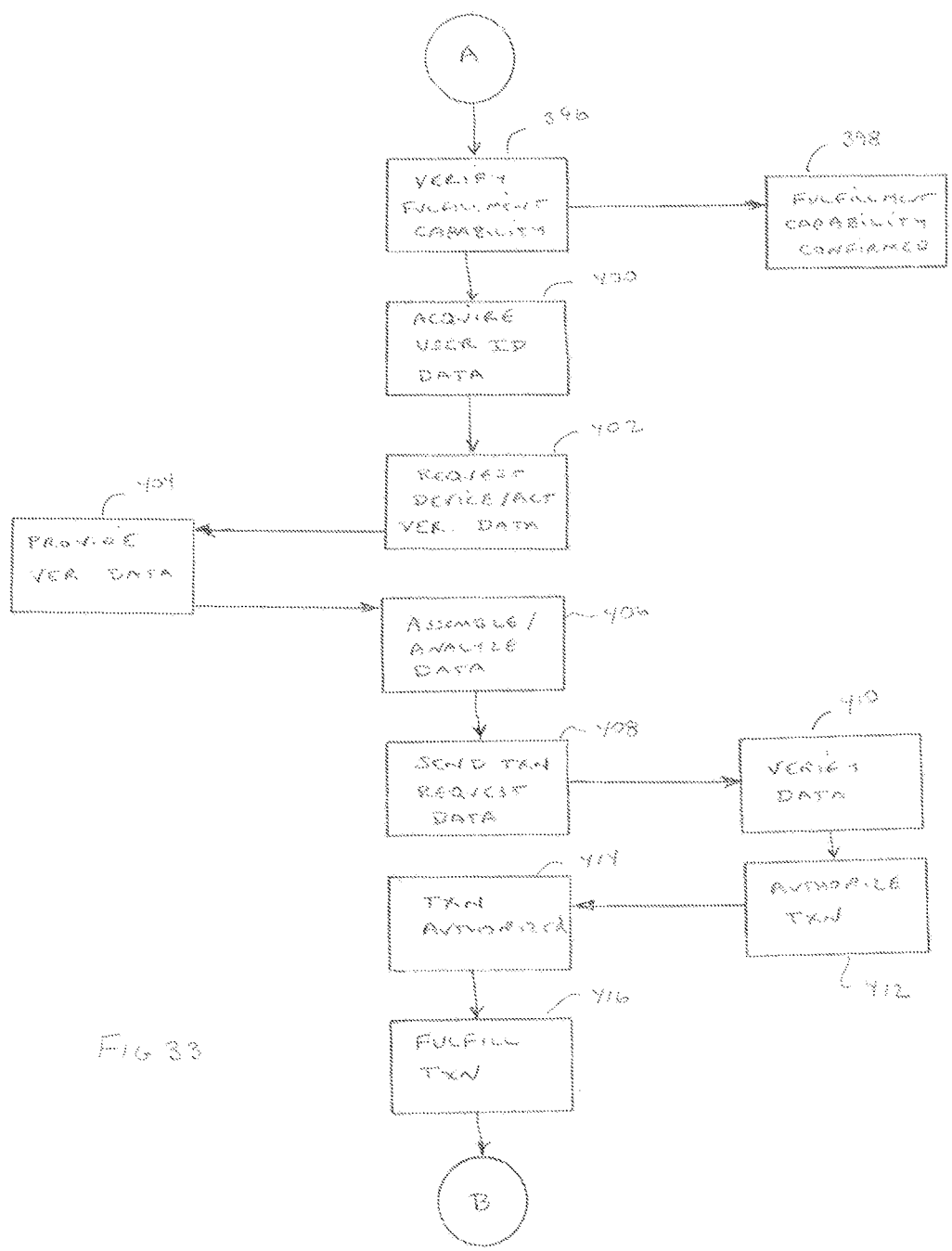
Figure 34:
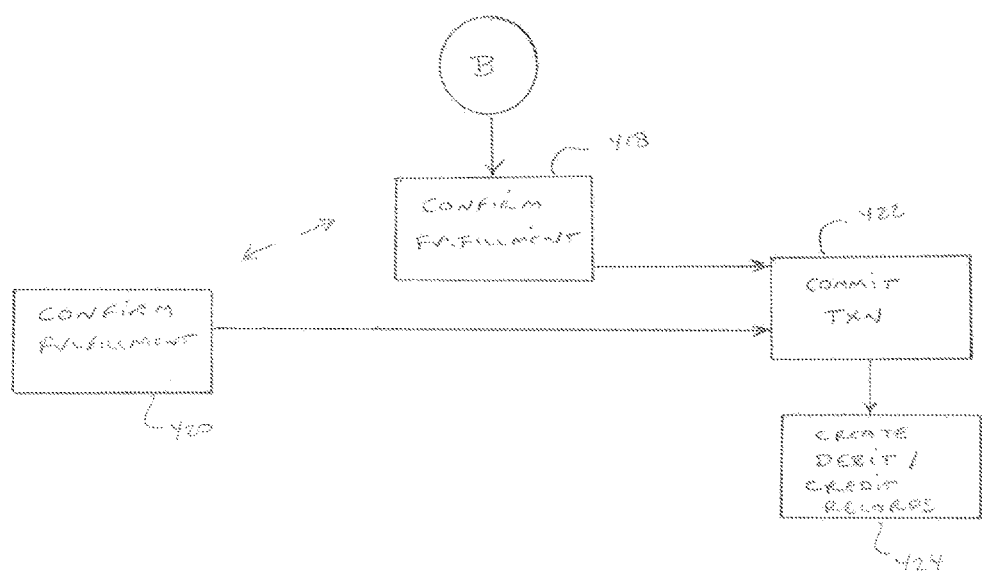

As represented in FIG. 32, when the user reaches the fulfillment point, the mobile device operates in accordance with its programming to transmit the user identifier, transaction ID and other information as may be required by the system to a device such as a terminal at the fulfillment point. This is represented by a step 366. In the exemplary arrangement the data is transmitted via radio frequency communications a short distance to a device at the fulfillment point. This may include, for example, Bluetooth or NFC communication via a wireless interface on an automated banking machine. Alternatively, other types of contact or wireless communication may be used.

In response to receiving the user identification and transaction ID information at the automated banking machine at the fulfillment point, the automated banking machine operates in accordance with its programming to send data corresponding to the user identifying information, transaction ID and an identifier associated with the fulfillment point to the transaction system. This is represented by a step 368. The one or more servers of the transaction system then operate to verify the user identification, transaction ID and other data to determine that the requested transaction is one which can be authorized. This is represented by a step 370. The transaction system communicates one or more messages to the fulfillment point to indicate that the data which has been sent is verified. In response to this communication, the automated banking machine at the fulfillment point then operates in accordance with its programming to provide to the mobile device a fulfillment point identifier which is then communicated wirelessly to the mobile device. This is represented by step 372.

The mobile device receives the fulfillment point identifier at a step 374. Of course it should be understood that in exemplary arrangements, additional data including data associated with maintaining security or authentication may also be communicated from the automated banking machine of the fulfillment point to the mobile device. The mobile device then operates in accordance with its programming to cause the fulfillment point identifier and the current location data of the mobile device to be sent wirelessly to the transaction system. This is represented by a step 376. In response to receiving the data sent in step 376, the transaction system operates in accordance with its programming to verify that the fulfillment point and the location of the mobile device correspond. The transaction system also operates to verify that the fulfillment point ID corresponds to the prior communication from the fulfillment point. Of course additional steps may be performed in connection with authentication or security of the communications by the transaction system. This is represented by a step 378.

The transaction system then operates in accordance with its programming to determine if the account associated with the requested user transaction currently is available for purposes of conducting transactions. This is done in a step 380. In the exemplary embodiment the account holder is enabled to operate their mobile device for purposes of enabling and disabling the status of their account. This capability may be used to assure that the account status is generally disabled at times when a user does not wish to conduct transactions. The user may selectively enable the account at times when the user wishes to conduct transactions, this can generally avoid unauthorized transaction activity. In this exemplary arrangement the transaction system at a step 382 determines if the account control status currently has the account disabled or "off" or enabled and "on." If in step 382 the transaction system determines that the account is currently disabled, the transaction system operates to cause one or more messages to be sent to the mobile device to indicate that if the transaction is to be conducted, the account status will need to be changed. The sending of this message is represented in a step 384.

The mobile device receives an account status change request from the transaction system in a step 386. If the user acknowledges that the transaction is to move forward, and is authorizing the transaction to proceed, the user will provide one or more inputs through input devices on the mobile device. The mobile device then operates in accordance with its programming as represented in step 388 to cause an account status change request messages to be sent wirelessly to the transaction system. The transaction system operates in accordance with its programming to change the account status so as to enable transactions as represented in step 390.

Enabling the account status then causes the transaction system to proceed at step 382 to operate in accordance with its programming to send transaction data to the automated banking machine at the fulfillment point. This is represented in step 392. The automated banking machine receives the transaction data sent by the transaction system as represented in step 394. The automated banking machine then operates in accordance with its programming to determine that it can fulfill the requested transaction. The automated banking machine, upon verifying that it can provide the requested transaction, such as dispensing the requested amount of cash, sends one or more messages to the transaction system confirming its fulfillment capability. This is represented by a step 396. The transaction system then receives the one or more messages which indicate that the machine has the fulfillment capability and will proceed with the transaction. This is represented in a step 398.

The automated banking machine at the fulfillment point then operates in accordance with its programming to prompt the user to provide user identifying data. This is represented in a step 400. In some exemplary arrangements the user identifying data may include a PIN number or other secret code for purposes of authorizing a transaction. In still other arrangements, the user identification data may include data read from a data bearing record, such as a card or biometric data such as data corresponding to a user's fingerprint or iris scan. In still other exemplary arrangements the identifying data may include audible sounds or a voiceprint. The automated banking machine in response to receiving this data in the exemplary embodiment then operates to communicate with the mobile device to request device and/or account verification data. This is represented in a step 402. The mobile wireless device in response to receiving the request operates in accordance with its programming to provide the requested verification data as represented in a step 404. Verification data is then wirelessly communicated to the automated banking machine. In some exemplary arrangements the verification data may include data such as account identifying data of the type previously discussed as being sent to the transaction system. Such verification data may also include the transaction ID data or other data that is received from the transaction system. In still other arrangements the verification data may include data resolved by the mobile device from data sent from the transaction system and data stored in one or more data stores in the mobile device. The type and nature of the verification data used may vary depending on the particular type of system and mobile device. Generally the verification data will be sufficient to verify the account, the particular transaction and device with which the transaction has been associated.

The automated banking machine which is the fulfillment point operates in accordance with its programming to receive the data from the mobile device. The machine then operates in accordance with its programming to assemble the user identifying data, data corresponding to account, transaction ID and other information so as to present the information to the transaction system. This is represented in a step 406. In step 408 the automated banking machine operates to send one or more messages to the transaction system so as to request authorization to complete the transaction. This is represented in step 408.

The transaction request messages are sent to the transaction system through one or more networks such as those described in connection with the previous embodiments. Such network communications may be wired or wireless communications and may include transmission over the Internet or other public or private networks. Encryption and other security features are included with or applied to the messages to avoid interception. One or more computers associated with the transaction system receive the messages and operate in accordance with their programming to verify the data associated with the transaction request. In verifying the data, the transaction system determines that the transaction is authorized to be conducted. This is represented in a step 410. In response to verifying the data and the propriety of the transaction, one or more servers of the transaction system operate to send one or more messages to the automated banking machine to authorize the transaction. This is represented in a step 412.

The automated banking machine operates in accordance with its programming in response to the received transaction authorization messages to verify that the messages correspond to instructions to fulfill the transaction. This is represented in a step 414. The automated banking machine then operates to fulfill the transaction as represented in a step 416. This may include in some exemplary embodiments operating to cause cash to be dispensed from the automated banking machine to a user. Of course it should be understood that this form of fulfillment is exemplary and in other arrangements other approaches and forms of delivering value may be used.

The automated banking machine operates in accordance with its programming to confirm that the cash was dispensed properly and sends one or more messages to the transaction system, confirming fulfillment of the transaction. This is represented by a step 418. In some exemplary arrangements the automated banking machine may communicate with the mobile device to prompt the user to confirm through one or more inputs through their mobile device that the cash or other value has been received. Alternatively the transaction system may communicate with the mobile device to have the user provide one or more inputs to confirm receipt of the cash or other value. The user of the mobile device then provides one or more inputs to the mobile device to confirm fulfillment. The mobile device then operates in accordance with its programming to cause one or more confirmation messages to be sent to the transaction system. This is represented in a step 420.

If the transaction system receives confirmation of fulfillment in messages from both the automated banking machine and the mobile device, one or more servers of the transaction system operate in accordance with their programming to commit the particular transaction. This is represented by a step 422. The one or more servers then operate to cause financial transfers such as debiting the account of the user for cash received and crediting the account of the entity who operates the machine or other system that has provided value that fulfilled the transaction request. This is represented by a step 424.

Of course it should be understood that in the event the user does not confirm fulfillment of the transaction or the automated banking machine is unable to fulfill the transaction, steps can be taken to again attempt to complete fulfillment in accordance with the programming of the transaction system, the fulfillment device and the mobile device. Alternatively or in addition, failure to receive appropriate confirmation messages may result in additional steps being taken such as the automated banking machine capturing images of the user receiving cash or other value from the machine so as to document that the transaction was properly completed. Alternatively or in addition, the devices included in the system may be programmed to operate so that the account of the user is not charged in the event that the transaction cannot be fulfilled.

It should be understood that although in the exemplary embodiment the fulfillment device is described as an automated banking machine of the type that automatically dispenses cash or other value to a user, in other arrangements the fulfillment device may include other types of automated banking machines. For example in some arrangements the automated banking machine which provides fulfillment may include a transaction terminal at a merchant location. The transaction terminal may include, for example, a cash register from which a merchant may remove cash and provide it directly to the user. Alternatively or in addition, other fulfillment devices may include wearable computers worn by merchant representatives who can control the wearable computers so as to provide messages that document the delivery of cash or other value to a user from merchant representatives.

Figure 35:
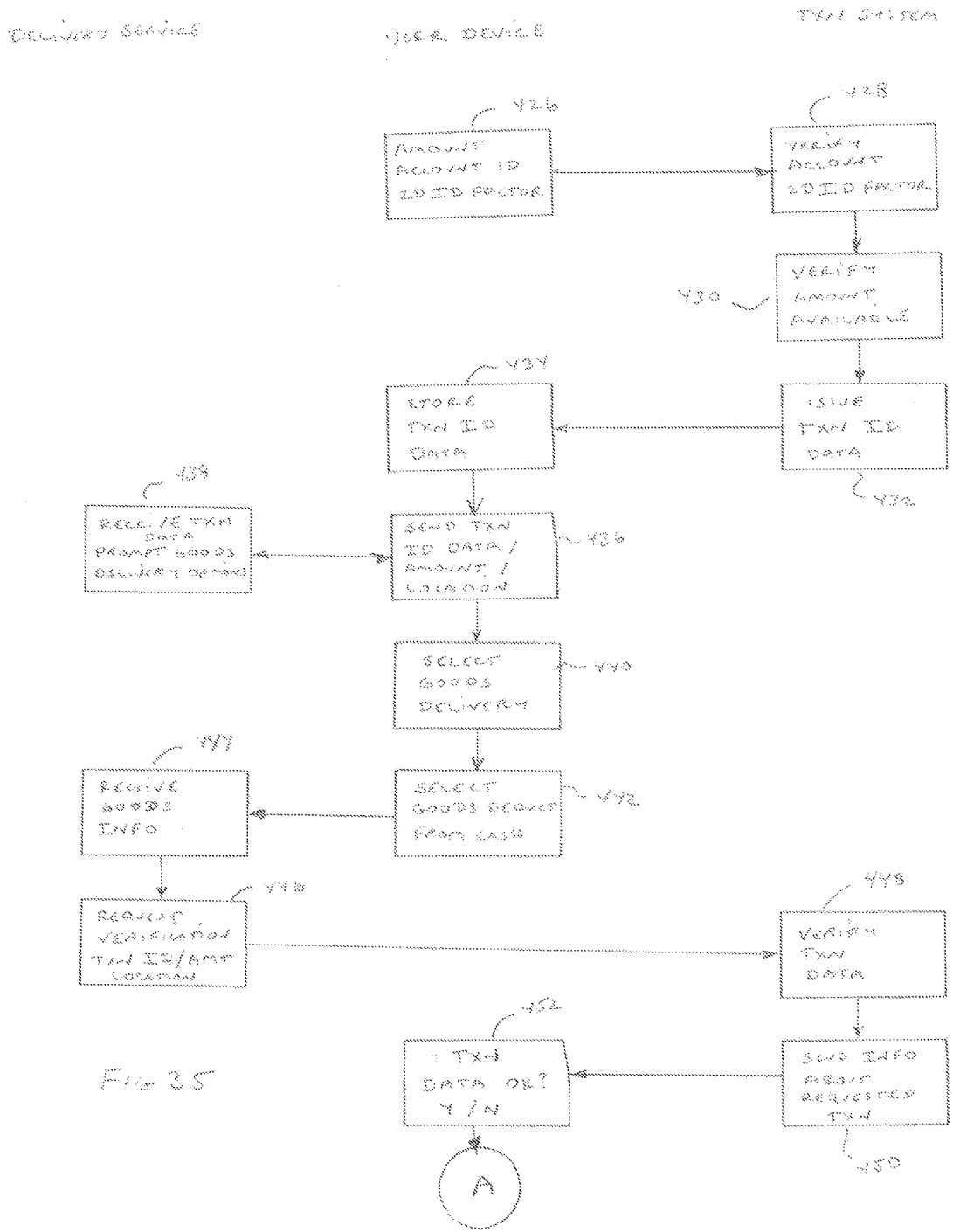
FIGS. 35-37 are a schematic representation of program logic carried out in one or more computers in connection with delivering cash or other items to a user.
Figure 36:
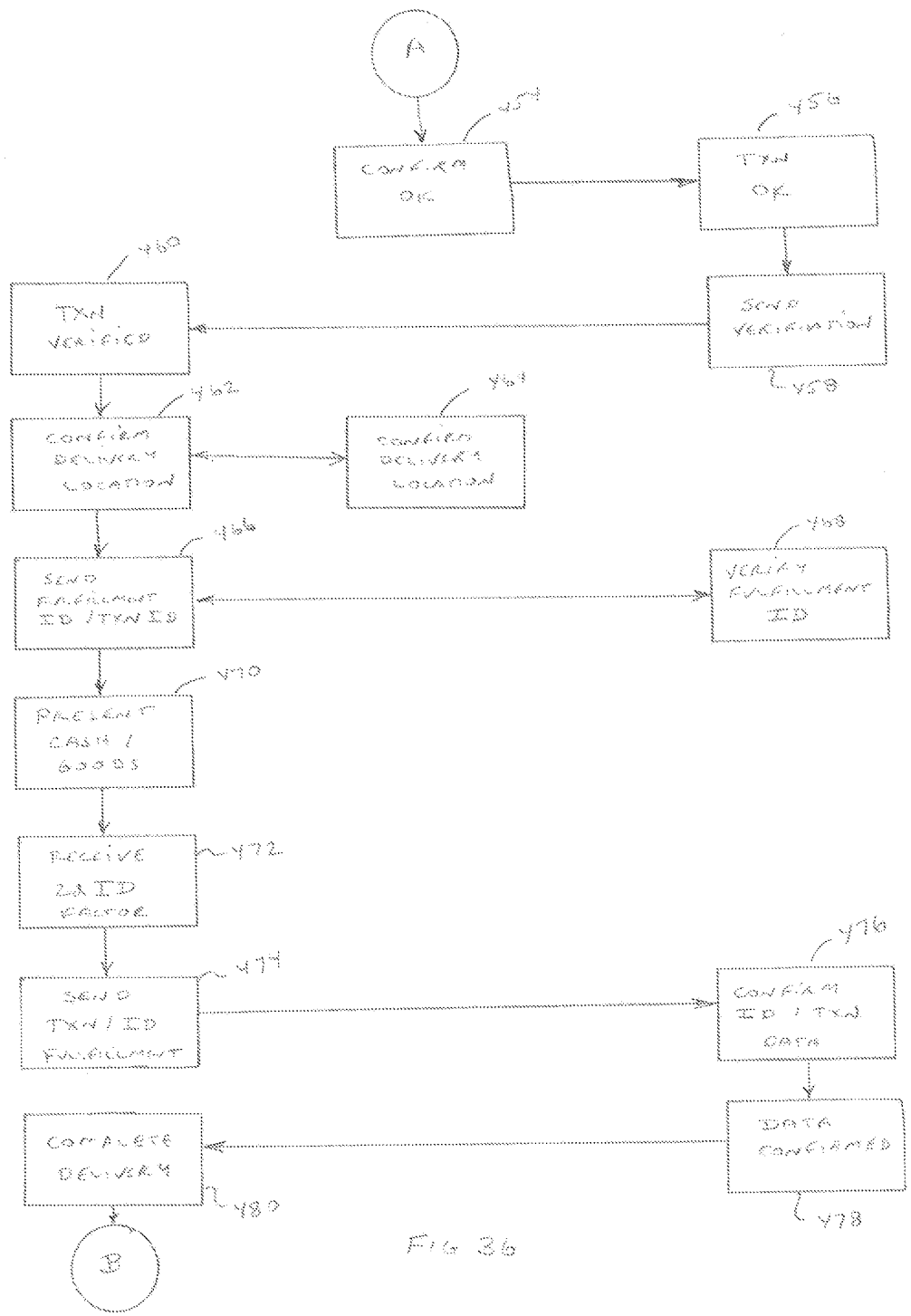
Figure 37:
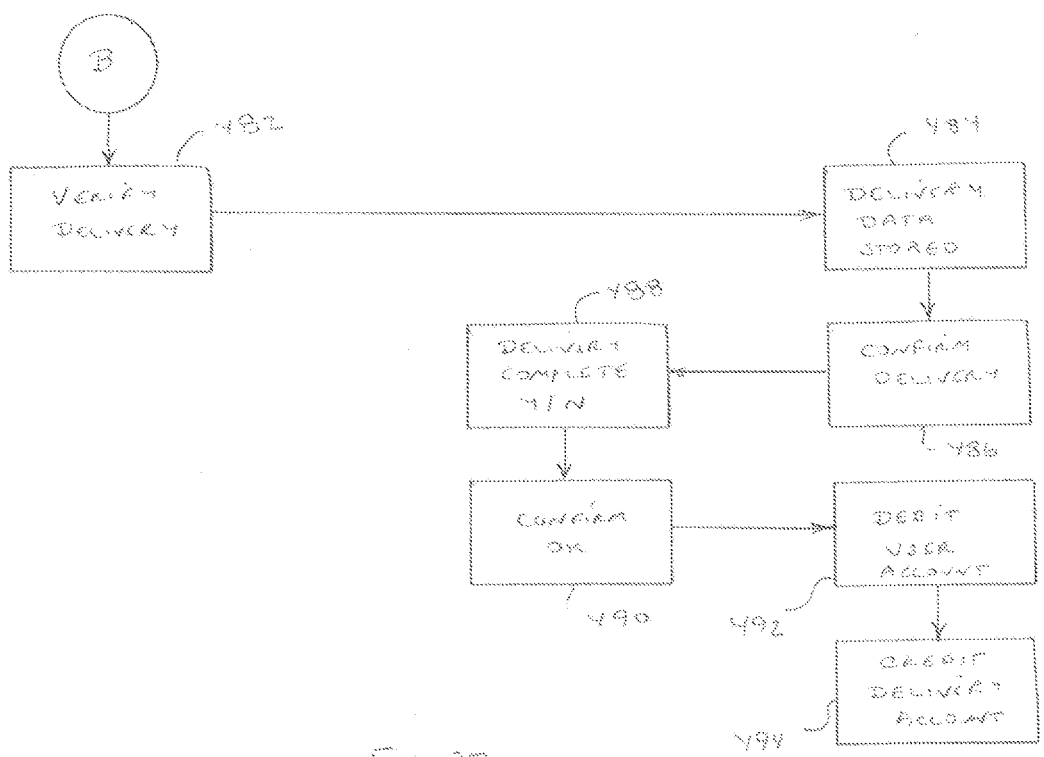

FIGS. 35-37 show schematically the program logic executed by one or more computers in an alternative system in which the user may receive cash or other value. The system described in connection with this exemplary arrangement unlike the previously described embodiment, may enable a user to have cash or other things of value delivered to them rather than the user having to travel to a fulfillment location to receive the requested value. In this exemplary arrangement a user may operate a user device such as a mobile device including a smart phone or wearable computer of the types previously described. Alternatively in some exemplary arrangements the user device may include a tablet computer or personal computer or other type of transaction terminal that is accessible by a user in connection with making transaction requests. In this exemplary arrangement the one or more devices that are operated by an entity that fulfills the user's transaction request are referred to as a delivery service. The transaction system utilized in connection with this exemplary arrangement may include one or more servers of the type previously described that operate in accordance with their programming and that may operate to cause financial transfers between the accounts of the various entities involved.

In this exemplary arrangement the user requesting a transaction operates a user device as represented in a step 426. In this exemplary embodiment the user device may include a portable wireless device through which a user provides inputs corresponding to a request for the amount of cash or other value that a user wishes to receive. The device also operates in accordance with its programming to recover from one or more data stores, data corresponding to an account. This may include an account number or alternatively token data or other data from which the transaction system can derive data corresponding to an account. In addition in this exemplary embodiment the user device operates to receive a second user identifying factor. Such an identifying factor may include, for example, a personal identification number from the user, a scan of a user's fingerprint, a user's voiceprint or spoken secret words, an iris scan or other suitable identifying factor which identifies the user as an authorized user. Of course it should be understood that additional data or other data may also be provided in connection with a particular transaction system.

The user device operates to send the transaction data to one or more servers associated with the transaction system. The servers operate in accordance with their programming to verify the account and other information which identifies the user as an authorized user and/or as the user of a valid account. This is represented by a step 428. The transaction system further operates in a step 430 to verify that the amount requested by the user is available. The transaction system then operates to generate a transaction identifier or other data that can be used to identify the user's requested transaction. This data is sent to the user device as represented in a step 432. Of course in other arrangements additional data such as data for authenticating the transaction, encrypting the communications, or that is otherwise usable in connection with the transaction may also be sent by the transaction system to the user device.

In the exemplary arrangement the user device is operative to store the transaction identifying data received from the transaction system as represented in a step 434. The user then may operate the user device at a time proximate to receiving the transaction identifying data or at a later time, to send the transaction identifying data and other data such as the amount of the cash or value requested, to a terminal device of the delivery service. Further in the exemplary embodiment the user device operates in accordance with its programming to send to the delivery service device, data corresponding to the current location of the user device and/or location data corresponding to a place of delivery. This is represented in a step 436.

In the exemplary arrangement the data communicated in step 436 from the user device is transmitted via wireless or wired communication to a terminal device including at least one microprocessor and data store operated by the delivery service. The delivery service device receives the transaction data and communicates with the user device to communicate options for the delivery of goods and/or the cash or other value that is requested by the user. This is represented in a step 438. For purposes of this exemplary arrangement, the delivery service will be described in connection with a service that provides food items for delivery. In some exemplary arrangements the services which are offered by entities who deliver food for consumption may be utilized to also provide cash or other items of value so as to make better use of the resources that are commonly used for such delivery. Of course this approach is exemplary and in other arrangements the delivery service may be solely dedicated to the delivery of cash or may deliver other types of items or value.

In the exemplary arrangement the data communicated from the device of the delivery service is received by the user device and causes the user device to operate in accordance with its programming to prompt the user to select whether the user wishes to have certain types of goods delivered along with the requested cash. This is represented in a step 440. The user provides inputs through one or more input devices of the user device to select any goods that the user also wishes to have delivered with their cash. Further as represented in a step 442 the user is prompted to provide inputs through the user device to indicate whether the value of the goods that they wish to have delivered is to be deducted from the amount of cash that they have requested. Generally in exemplary embodiments because the transaction has been previously verified for a given amount, the user will be required to agree that the cost of the goods will be deducted from the cash or other form of value that the user will additionally receive. In alternative arrangements, if the user wishes to receive goods and cash or other value which have a greater value than that originally authorized, the user device and the transaction system may operate in accordance with their respective programming to authorize the requested higher transaction amount.

In the exemplary transaction, the user agrees to have the value of the goods deducted from the initially authorized amount and communicates the goods information and such confirmation to the device operated by the delivery service as represented in a step 444. The terminal device of the delivery service then operates in accordance with its programming to cause one or more messages to be sent by the delivery service device to the transaction system. The messages in the exemplary arrangement are operative to request verification of the transaction ID, the total value of the transaction, and the location for delivery that has been provided to the delivery service device from the user device. This is represented in a step 446.

The data communicated from the delivery service device is then verified as correct through operation of the transaction system. This is represented in a step 448. Of course if the transaction data cannot be verified through operation of the transaction system, the exemplary arrangement sends appropriate messages to the delivery service that the transaction is not verified and should not proceed. In addition other steps may be taken as well in accordance with the programming of the servers which comprise the transaction system and/or the terminal device of the delivery service.

If the transaction data is verified in step 448, the transaction system of the exemplary embodiment operates in accordance with its programming to cause one or more messages to be sent to the user device indicating the information concerning the requested transaction. This is represented in a step 450. The data sent to the user device may include details of the transaction, the delivery service, the amount involved, the goods involved or other information as is necessary for the user operating the user device to evaluate whether the transaction should proceed. The data sent to the user device causes the user device to present an interface to the user which requests that the user provide inputs to either authorize or disallow the transaction. This is represented in a step 452. If the user does not confirm the transaction, then the transaction does not proceed and an appropriate message is sent to the transaction system.

Assuming that the user confirms the transaction as acceptable, one or more messages confirming such fact is sent to the transaction system is represented in step 454. The transaction system evaluates the messages and confirms that the transaction is acceptable as represented in step 456. The transaction system then operates in accordance with its programming as represented in step 458 to send one or more messages to the device of the delivery service to indicate that the transaction has been verified as authorized. The device of the delivery service receives these messages and verifies the receipt of transaction verification as represented in a step 460. In response to verifying that the transaction should proceed, the device of the delivery service operates in accordance with its programming to communicate with the user device to confirm the delivery location. This is represented by a step 462. The user device then provides communication to confirm the delivery location as represented by a step 464.

In response to confirming the delivery location, the delivery service device operates in accordance with its programming to send messages to the transaction system. The data sent by the delivery service device includes data corresponding to a fulfillment identifier (ID) associated with the delivery service as well as the transaction identifier associated with the particular transaction. The sending of this information is represented in a step 466. In response to receiving the data from the delivery service device, the transaction system verifies that it recognizes the fulfillment ID associated with the delivery service and confirms that it can complete the transaction associated with the financial transfers involved. This is represented by a step 468. In the exemplary arrangement if the transaction system determines that it cannot complete the financial transfers associated with the transaction, appropriate messages are sent to the device associated with the delivery service so as to prevent the transaction from proceeding.

In response to verifying the fulfillment ID and transaction ID by the transaction system, the delivery service device receives confirmation messages from the transaction system to proceed with delivery of the cash and the requested goods. The delivery service then transports the requested cash and goods to the location where the user is located. The transport of the goods and cash may be tracked through operation of a device associated with the delivery service such as a portable terminal, wearable computer or other device which may be the same as or may be a separate terminal device capable of being in communication with the delivery service terminal receiving the other messages. The presentment of the cash and goods is represented by a step 470. In the exemplary arrangement when the goods and cash or other value is presented to the user at the location, a portable terminal associated with the delivery service is operative to receive identifying data to identify that the user receiving the goods and cash is the appropriate recipient. This may include, for example, in some embodiments the portable terminal of the delivery service receiving data such as card data from a data bearing record provided by the user. Alternatively the portable terminal may receive a biometric identifier such as a fingerprint of the user. Alternatively or in addition, the terminal associated with the delivery service may receive identifying data from the mobile device of the user. Various types of input information or combinations of information may be so received which can be verified as associated with the authorized user. The receipt of the identifying factor or factors by the delivery service terminal is represented by step 472.

As represented in a step 474, in the exemplary arrangement the portable terminal associated with the delivery service is operative to send data indicative of the delivery of the cash and/or goods to the transaction system. In the exemplary arrangement the portable terminal of the delivery service is further operative to send the transaction data and data corresponding to at least a portion of the received user identifying data to the transaction system. Of course it should be understood that in step 474 additional data and/or other information that is usable to verify that the delivery is completed or the transaction is being fulfilled may also be sent to the transaction system.

As represented in a step 476, the transaction system of the exemplary embodiment operates to confirm the user identifying data and the transaction data associated with delivery of the goods and cash. The transaction system then operates in accordance with its programming in a step 478 to send one or more messages to the portable terminal of the delivery service to indicate that the identifying data has been confirmed. In response to receiving the confirmation data from the transaction system, the portable terminal of the delivery service prompts the individual making the delivery to complete the delivery as represented in a step 480. The delivery service terminal then prompts the user from the delivery service to verify the delivery through providing at least one input to the terminal and sends at least one message to the transaction system verifying that delivery has been completed in accordance with a step 482. In the exemplary arrangement the transaction system receives the data corresponding to the verification of delivery in a step 484. In response to receiving this data, the transaction system stores the data indicating delivery has been made. The transaction system service further operates in accordance with its programming to send to the user's portable device, one or more messages asking the user to confirm delivery of the goods and cash. This is represented in a step 486.

In response to receiving the one or more messages from the transaction system, the user device operates in accordance with its programming to present an interface to the user which prompts the user to provide an input that the delivery of the requested goods and cash has been completed. This is represented in a step 488. If the transaction is proceeding properly, the user then provides one or more inputs to the user device which causes one or more messages to be sent to the transaction system confirming that the delivery has been made in a satisfactory manner. This is represented in a step 490. Responsive to receiving the one or more messages sent by the user device in step 490, the transaction system operates to cause a charge or debit to be made against the account of the user as represented in a step 492 and to cause a credit for the amount of cash and goods or other value delivered by the delivery service as represented in a step 494.

Of course in the exemplary arrangement if the user does not confirm appropriate delivery of the goods, additional steps are taken so as to resolve the discrepancy. This may include, for example, additional communications between the delivery service terminal, the user terminal and the transaction system so as to prevent or revoke the delivery of the goods, cash or other value to unauthorized persons. In addition, the user terminal and delivery service terminal may include image capture devices or other devices for obtaining information so as to document the circumstances of delivery if the delivery is going to be completed so that the recipient cannot deny delivery at a later date. The particular steps taken will depend on the capabilities of the particular system and the devices involved. Further it should be understood that additional or different steps may also be taken through operation of the various devices in connection with the exemplary steps described. Further numerous different variations may be utilized in connection with various embodiments. Further although cash and goods delivery has been described as the form of value delivered in connection with this exemplary embodiment, it should be understood that other types of delivery may also be made. This may include, for example, other types of value such as prepaid cards, stored value cards, gift cards, scrip or other things that can be redeemed for goods or services. Of course it should be understood that numerous different combinations of goods, services, cash or other items of value may also be delivered through systems of this type.

Figure 38:
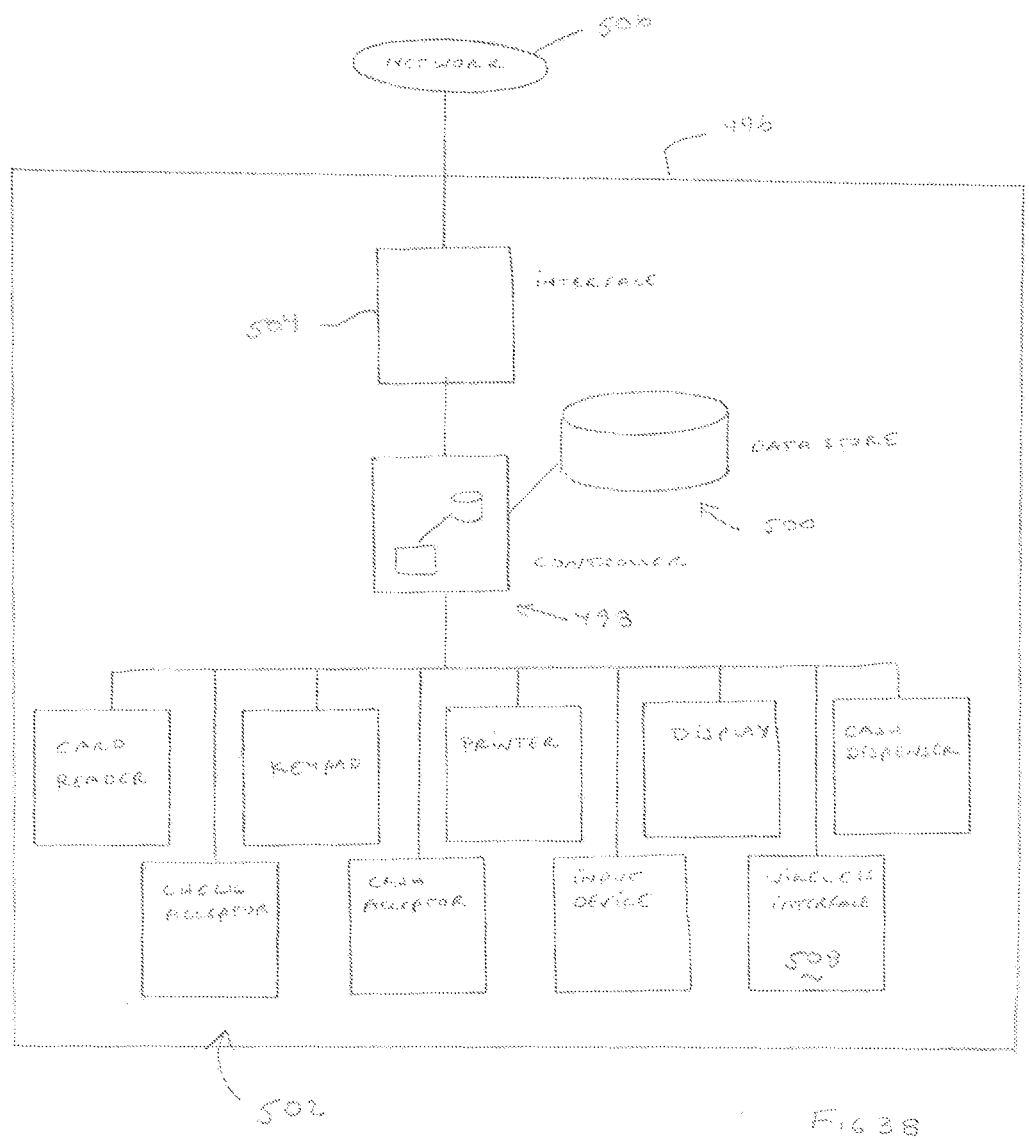
FIG. 38 is a schematic view of an automated banking machine which communicates with mobile user devices.

FIG. 38 shows schematically a further alternative embodiment of an automated banking machine 496. Automated banking machine 496 may include features like the automated banking machines previously described and may be used for carrying out transactions including transfers of value. The exemplary automated banking machine includes a controller 498 including a microprocessor. The controller further includes one or more data stores schematically indicated 500 which store computer executable instructions, data and other information associated with operation of the automated banking machine. The automated banking machine further includes a number of transaction function devices collectively referred to as 502 that are in operative connection with the controller. The transaction function devices may include, for example, in some embodiments card readers, key pads, printers, displays, cash dispensers, check acceptors, cash acceptors, input devices, output devices and various other types of devices that are used in connection with the particular types of transactions that are carried out by the automated banking machine. The exemplary machine further includes a suitable interface 504. Interface 504 is usable to provide communications with one or more networks 506. Networks 506 are in operative connection with one or more transaction systems including remote computers such as servers and other systems which enable carrying out transactions of the type for which the automated banking machine is specifically adapted.

The exemplary automated banking machine 498 further includes a wireless interface 508. The wireless interface 508 of the exemplary embodiment is suitable for radio frequency communication with relatively nearby mobile devices. Such mobile devices may include smart phones, tablet computers, wearable computers or other portable computing devices commonly carried by users which may come into proximity with the machine. In the exemplary arrangement the terminal controller 498 or other microprocessor device in association with the machine may be operative to provide communications with one or more types of mobile devices and applications operating therein. Further in some exemplary arrangements the communication provided is operative to inform a user mobile device that the automated banking machine may provide a particular type of service or transaction function that a user associated with the mobile device may be seeking to obtain.

For example in an exemplary embodiment a mobile device of the user may include a particular application or other suitable programming that enables a user to establish parameters for things that they wish to purchase or otherwise acquire. Such an application may enable the user to indicate a request to obtain cash in a particular amount and to not incur a transaction fee for receipt of the cash above a particular threshold. For example the user may program their mobile device to seek to obtain cash in the amount of $300 without incurring a transaction fee in excess of $2.00. Of course it should be understood that this amount and transaction fee are merely exemplary.

The exemplary automated banking machine 496 may include data in its one or more data stores 500 that it is willing to offer the dispense of cash in certain amounts for certain transaction fees. The controller of the machine may further include programming so as to communicate this information when a request of this type is received by the machine through the wireless interface. Further in some exemplary embodiments the programming of the automated banking machine may be such that normal transactions attract transaction fees that are higher than those that the owner of the machine is willing to offer to those which are seeking lower transaction fees through communications with transient mobile devices through the wireless interface.

In the exemplary embodiment the mobile device of the user is carried by the user and transmits wireless messages corresponding to those items that the user is seeking nearby terminals which can receive such messages. The automated banking machine is operative to receive through its wireless interface the messages from the user's mobile device including messages which indicate that the user is seeking to receive cash in the particular amount for a transaction fee that is no more than the indicated fee. In response to receiving these messages, the controller of the automated banking machine is operative to determine that the machine is programmed to offer transactions that satisfy the parameters that the user is seeking. The controller then operates in accordance with its programming to communicate with the user's mobile device through the wireless interface. The controller operates to indicate to the user device the fact that the requested transaction is available and the location where the machine is located. The user may also be prompted to receive directions to travel to the machine if the user is interested in completing the transaction. Further in exemplary embodiments the user may also be informed through messages from the machine that in order to obtain the cash for the requested fee, the user can use a certain code or token which is provided by the machine to the user device. In the exemplary embodiment the user operating the mobile device may operate the device to receive the data or token from the machine at the time of the initial communication. Alternatively in other arrangements the user may be advised that they can obtain the discounted transaction fees by taking other steps when they are present at the machine.

If the user elects to travel to the machine, the user may commence a transaction in the usual manner such as by presenting a card and PIN number. In the exemplary arrangement the programming of the automated banking machine is configured to prompt the user to provide an input to indicate that they are conducting a transaction in response to a promotional offer received through their mobile device. In response to selecting this particular transaction selection, the user is enabled to provide the code or token previously delivered to their mobile device. This can be provided by communication of the user's device with the machine or the user providing manual inputs to the machine. Alternatively the user can commence another communication session through their mobile device while at the machine so as to indicate to the machine that they are responding to the promotional offer to receive the cash for the reduced transaction fee. In response to receiving the information from the user, the machine operates in accordance with its programming to fulfill the transaction requested by the user. This would include in the exemplary embodiment the delivery of cash with the assessment of only the $2.00 transaction fee as agreed to by the user. In this exemplary arrangement the machine is programmed to cause any additional charges that may be associated with the transaction to be absorbed by the machine owner or the owner of the establishment in which the machine is located. Alternatively in some alternative arrangements the machine user may be assessed the usual transaction fee, but may be issued a receipt, token or instructions that allow the user to receive cash or other value from the establishment where the machine is located that corresponds to the excess fee charged over what the user requested. The owner of the machine or the establishment may do this in order to obtain the benefit associated with having the user present in their establishment with cash that can be used to acquire goods and services from the merchant. Alternatively and/or in addition the user may be required to watch certain advertising or other information output by the machine about goods and services of the establishment or the machine owner while receiving the cash for the discounted fee. In this manner the exemplary embodiment provides for the user to receive the discounted transaction fee they requested and the operator of the machine and/or the establishment in which the machine is located, to receive the additional benefit associated with more customers present within the establishment and/or reviewing advertising messages associated with the establishment.

Although the particular mobile device request described that provides for the receipt of cash for a discounted transaction fee may be fulfilled through operation of exemplary automated banking machines, other mobile device request offers may also be responded to. This may include, for example, offering to fulfill requests associated with other types of goods and services that can be obtained through operation of the automated banking machine. Such goods and services may include the provision of items such as tickets for events, gaming materials or other items that can be offered through operation of the automated banking machine. Alternatively and/or in addition offers to fulfill requests may be associated with the goods or services provided by the particular establishment. For example if the particular mobile device user application enables the user to transmit requests to receive particular goods or services at certain prices or within particular ranges, the automated banking machine may be programmed to communicate with the user devices that the particular establishment in which the machine is located, will offer the particular things that the user is looking for. Further as can be appreciated, the programming of the automated banking machine may enable the machine to be programmed so as to identify particular thresholds at which the machine and/or establishment is willing to offer particular goods and services.

Alternatively or in addition other exemplary embodiments may enable communications between the controller of the machine and other terminals within the merchant establishment to indicate that there is a user in proximity who is looking for something that may correspond to that which the merchant has to offer, but the user's request parameters do not correspond to that which the establishment has currently programmed the machine to offer. In such cases communication with a merchant terminal may enable a merchant user to agree to meet the particular parameters being requested by the user of the mobile device. Inputs to the merchant terminal which operatively communicates with the machine may then enable the machine to inform a user through their mobile device that the particular merchant establishment is prepared to offer what it is that the user is looking for. Alternatively, in some arrangements the merchant terminal may communicate with the user's mobile device directly. Those exemplary arrangements may enable a user of a mobile device to use the device to look for things at particular prices and to obtain those things from automated banking machines or from merchant establishments as they travel in proximity to such locations. Of course it should be understood that these approaches are exemplary and in other embodiments other approaches may be used.

Figure 39:
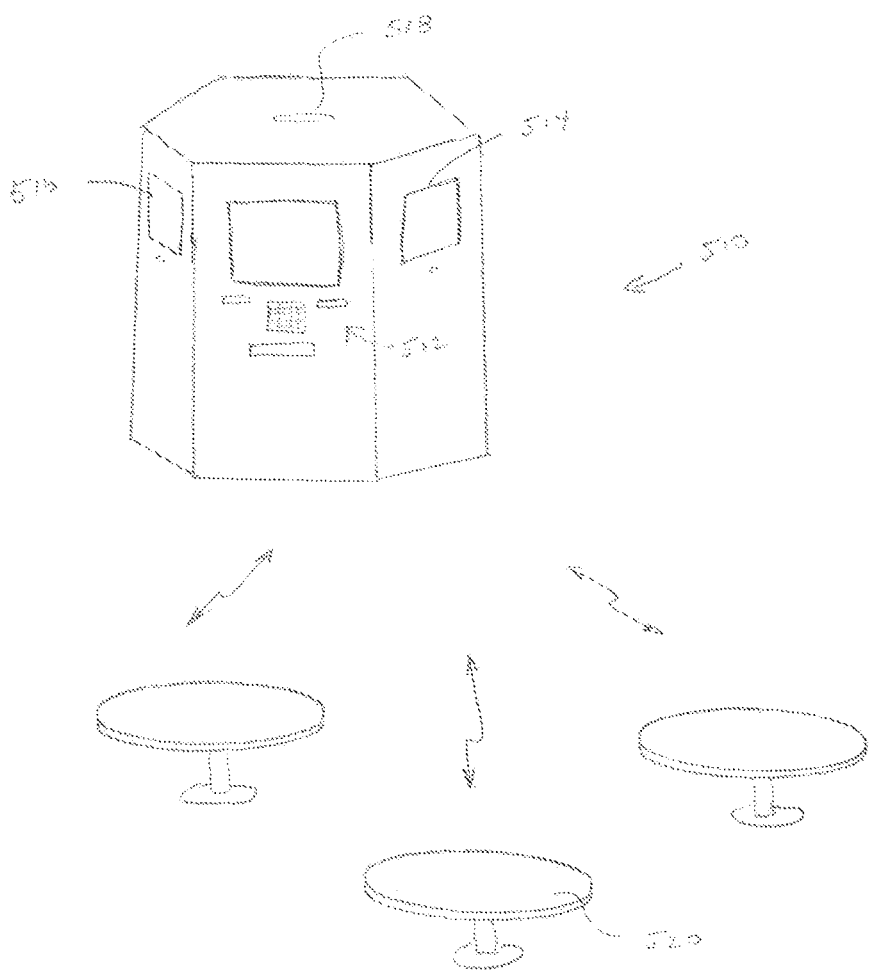
FIG. 39 is a schematic view of an automated banking machine and system that provides displays for mobile computers and carries out multiple transaction types.

A further exemplary embodiment of an automated banking machine 510 is schematically represented in FIG. 39. The automated banking machine 510 may include features and devices similar to those previously described except as otherwise mentioned herein. The exemplary automated banking machine 510 may be used for carrying out transactions of the types previously discussed at a transaction user interface area 512. Interface area 512 of the exemplary embodiment may include items for communicating with a user during transactions such as a display, key pad, card reader, acceptor slot, printer delivery slot, cash accepting slot, cash delivery slot, check accepting slot or other appropriate interface elements for carrying out transactions with users.

Exemplary automated banking machine 510 further includes additional visual displays 514 and 516. In the exemplary embodiment, these visual displays are provided for purposes of facilitating activities by individuals who carry mobile devices and wearable computers that do not have visual displays and/or which may not have visual displays of a suitable size or configuration to carry out certain types of desired functions. The exemplary automated banking machine includes one or more wireless interfaces that are suitable for communicating with such mobile devices and which can facilitate the use of such devices or multiple devices that are carried by multiple users.

For example in some exemplary arrangements mobile devices may include a device such as a watch-like wearable computer, pendant or other mobile computing device that includes no visual display or only a small visual display. Bringing such a mobile device in proximity with a display such as display 514 causes the automated banking machine to operate in accordance with its programming to prompt the user to provide an input if they wish to utilize the display on the machine in connection with their device. In the exemplary arrangement the displays comprise touch screen displays which enable a user to select whether they wish to utilize the display or not. By selecting an option presented through the display to connect to the mobile device, the mobile device can then present a user interface to the user through the display which provides multiple options and selections to the user. The user can then interface with their mobile device through the touch screen display on the automated banking machine. Further in exemplary arrangements the interface may also provide outputs from remote sources such as outputs produced by various Internet or other network connections that the user is able to make through their mobile device. Thus the user is able to utilize their mobile device while using the display in connection with the automated banking machine as the input and output user interface for the mobile device.

Further in exemplary embodiments the automated banking machine may provide a printer which enables the user of the mobile device to print an item selected via the particular interface that is output through the display. The printer of the automated banking machine may deliver to the user the printed information that they have caused to be selected through or presented on the display. The automated banking machine may include one or more printer outlets 518 for this purpose. Further in exemplary embodiments the automated banking machine may operate in accordance with its programming to charge the user for use of the printing function or for other functions that a user may choose to execute when using the display interface provided on the machine. For example if a user uses the display interface in order to request that funds be added to a mobile wallet associated with the mobile device, the automated banking machine terminal controller may operate in response to the user's selected inputs to cause data representative of value to be included in the mobile wallet and to cause communications with appropriate networks so as to cause the user's account to be charged. Alternatively or in addition the automated banking machine may operate to cause money to be transferred to or from stored value accounts associated with the user's mobile device. Of course these approaches are exemplary and in other embodiments other approaches may be used.

In addition when the automated banking machine is located at a merchant establishment, provision may be made to have user interfaces which provide visual outputs from user mobile devices and which can receive user inputs to such devices located in other devices within the establishment. For example in some arrangements the automated banking machine may be located in a coffee shop or restaurant environment in which there are tables with input/output devices such as surface computers 520. The surface computers 520 may comprise input and output devices which communicate with a user's mobile device and enable the user to employ the surface computer of the table or similar structure as the display and input device for the mobile device.

In still other exemplary embodiments the displays in operative connection with the automated banking machine may be usable for purposes of facilitating transfers of value between mobile devices of multiple users. When mobile devices of users do not have suitable displays such as certain wearable computers, visual outputs may be presented to the user's mobile devices on the displays in communication with the automated banking machine. In situations where a user wishes to transfer value from a stored value account or other account, to another user who has a mobile device, both users may bring their devices in proximity to a touch screen display associated with the automated banking machine. In such circumstances, devices may communicate with the machine to provide outputs through the display and the users may provide inputs so as to use the interface presented by the machine for communication with one or both devices. In such circumstances the display may be used to provide inputs and receive outputs to cause value to be transferred from one device to another and/or to the accounts of the respective users. Thus for example if a user of a mobile device wishes to transfer funds to a user of another mobile device, they may do so using the interface provided on or through communication with the automated banking machine. Further in exemplary embodiments the automated banking machine may include encryption features or other security features that help to assure that the communication of the messages which communicate the value or cause the value to be transferred are secured in a manner that is more effective than occurs when mobile devices communicate directly. Such encryption functions may be controlled or initiated through inputs provided to the displays that are connected to the automated banking machine. For example the automated banking machine may have its controller operate in accordance with its programming to provide to mobile devices, one-time session keys and/or encryption keys that are usable to provide communication on a secure basis between the mobile devices while they are operated in connection with the automated banking machine. Thus the automated banking machine may provide additional value that facilitates the carrying out of transactions between wearable computers, particularly such computers that do not include user displays.

Further in exemplary embodiments the automated banking machine 510 may be utilized for purposes of providing electronic tokens to wearable computers that can be used as a substitute for account numbers or account verification data in connection with carrying out financial transactions. For example it may be desirable in some transaction arrangements to use a token which can be used by a remote computer system to resolve a user's account number, rather than the actual account number for purposes of carrying out transactions. In addition tokens may also be provided for other data such as data corresponding to biometric data, PIN numbers or other values which a user may not want to have available in transmissions which could be intercepted or utilized by unauthorized persons if they are stored in a mobile device that is lost or stolen.

The exemplary automated banking machine operates in accordance with its programming to provide one or more tokens to users which can be stored in a user's mobile device. For example the automated banking machine may operate to receive a user's credit or debit card data as well as a PIN number or biometric data that authenticates the identity of the user. In response to the user providing inputs through the automated banking machine indicating that the user wishes to receive a token for a mobile device, the automated banking machine operates in accordance with its programming to communicate with a remote transaction system. The remote transaction system verifies the authenticity of the card data and PIN or other data to determine that the user is an authorized user. In response to messages corresponding to token data from the remote system, the automated banking machine may then deliver through the wireless interface, a token that is stored in the memory of the user's mobile device. As can be appreciated, the token corresponds to data which a remote transaction system may receive, validate and associate with the user's account data. However, the token data has no relationship to the user's account data and thus if the token data is compromised, the user's account number is not obtained. Thus in exemplary arrangements once the user has received token data and stored it on their mobile device, the user can conduct transactions on their account using the token data in communications directly with the transaction system without transmitting their account number directly.

In other exemplary embodiments the automated banking machine may also operate to dispense token data corresponding to parameters other than a user's account number. This may include for example, token data corresponding to a user's biometric data, which token data may be stored in a user's mobile device. Such data may be sent from the mobile device in lieu of actual biometric data when it is required for purposes of verifying transactions. Alternatively or in addition the token data may be used and correlated by a remote system to compare fingerprint data that is scanned either on the user's mobile device or at a separate transaction terminal, with the remote system stored data so as to verify the user. Using a token stored on the mobile device instead of the biometric data itself produces the risk of compromise of the data.

Further in other exemplary arrangements the automated banking machine may be utilized to help users to avoid fraudulent transactions that may be conducted via other methods. For example a user may prefer to order goods or services by phone or using a personal computer which uses only the user account data which can be read from a card. Such transactions where the actual card is not presented to the merchant or a merchant's transaction terminal, can present risks because the data that is stored on a chip associated with a genuine card is not available to verify that the card is genuine. This is because in a transaction that is carried out either on the phone or at a PC or other terminal that cannot read the data from the chip on the card or communicate with the chip, only the visible data on the card can be used in connection with presenting the transaction.

Exemplary embodiments of automated banking machines may operate to provide the user with additional information or capabilities that can be used in transactions that are conducted with merchants when the card is not present. This may include, for example, the automated banking machine operating to verify the authenticity of the user's card including chip data included on the card. The user may also be authenticated by other factors such as the user's PIN, biometric identifiers or other data. With the user and their card authenticated, the terminal may operate to provide the user with an additional authenticating factor or a device that can provide such a factor that can be used when transactions are conducted with a merchant where the card is not physically presented to the merchant. In some arrangements this may include an additional secret code that is provided to the user from the automated banking machine. The secret code may be stored in a remote system for use in connection with transactions that are conducted by a merchant when the card is not present. Thus for example if the user places an order for goods on the phone or through a PC, the user can additionally provide the secret code in addition to the data on the card so as to further authenticate the transaction as authorized. Alternatively in some embodiments the machine may provide the user with an article in a manner like that previously discussed, which article can output data which can be used as an additional authenticating factor.

Alternatively and/or in addition, if the user normally conducts transactions such as purchase transactions by phone, when using the automated banking machine to receive transaction authenticating credentials for use in future "card not present" transactions, the user may be requested to provide an input to the automated banking machine of a spoken code word that the user will use in connection with transactions that are conducted in the future by phone. The automated banking machine may operate in accordance with its programming to communicate data corresponding to the code word and/or a voice print to the remote transaction system. The data is then securely stored in memory. When the user later wishes to place an order for goods via telephone, the communications by phone may include the user presenting the code word verbally to the order system in addition to data that is read from the card. This provides an additional authenticating factor that the merchant receiving the order can use to have higher assurance that the transaction being presented by the user is authorized. Of course these are but examples of things that an automated banking machine may provide as additional authenticating factors to help assure that transactions requested of a merchant in circumstances where the card is not present at the merchant location, are not fraudulent.

Thus the exemplary embodiments achieve improved operation, eliminate difficulties encountered in the use of prior devices and systems, and attain the useful results described herein.

In the foregoing description certain terms have been used for brevity, clarity and understanding. However, no unnecessary limitations are to be implied therefrom because such terms are used for descriptive purposes and are intended to be broadly construed. Moreover, the descriptions and illustrations herein are by way of examples and the invention is not limited to the features shown and described.

Further in the following claims any feature described as a means for performing a function shall be construed as encompassing any means known to those skilled in the art as being capable of carrying out the recited function and shall not be deemed limited to the particular means shown or described for performing the recited function in the foregoing description or mere equivalents thereof.

It should be understood that features and/or relationships associated with one embodiment can be combined with features and/or relationships from another embodiment. That is, various features and/or relationships from various embodiments can be combined in further embodiments. The inventive scope of the disclosure is not limited to only the embodiments shown or described herein.

It should be understood that language which refers to a list of items such as "at least one of A, B, or C" (example 1) means "at least one of A, B and/or C." Likewise, it should be understood that language which refers to a list of items such as "at least one of A, B, and C" (example 2) means "at least one of A, B and/or C." The list of items in example 2 is not required to include one of each item. The lists of items in both examples 1 and 2 can mean "only one item from the list or any combination of items in the list." That is, the lists of items (in both examples 1 and 2) can mean only A, or only B, or only C, or any combination of A, B, and C (e.g., AB, AC, BC, or ABC).

The term "non-transitory" with regard to computer readable medium is intended to exclude only the subject matter of a transitory signal per se, where the medium itself is transitory. The term "non-transitory" is not intended to exclude any other form of computer readable media, include, but not limited to, media comprising data that is only temporarily stored or stored in a transitory fashion. Should the law change to allow computer readable medium itself to be transitory, then this exclusion is no longer valid or binding.

Having described the features, discoveries and principles of the exemplary embodiment, the manner in which it is constructed and operated and the advantages and useful results attained, the new and useful structures, devices, elements, arrangements, parts, combinations, systems, equipment, operations, methods, processes and relationships are set forth in the appended claims.

We claim:

1. Apparatus comprising:
   an automated banking machine operable responsive at least in part to read user data to cause financial transfers,
      wherein the machine includes at least one user input device, wherein the at least one user input device includes at least one data reader,
   wherein the at least one data reader is operable to read user data usable to identify a financial account of a machine user,
wherein the machine includes at least one display,
wherein the machine includes at least one document reader,
wherein the at least one document reader is operative to electronically read data from documents,
wherein the machine includes a cash dispenser,
wherein the cash dispenser is operable to selectively dispense currency bills from the machine,
wherein the machine is associated with at least one controller,
wherein the at least one controller is in operative connection with at least one data store,
wherein the at least one controller is configured to cause a determination to be made that user data read by the at least one data reader is associated with a financial account on which a transaction is authorized to be conducted through operation of the machine,
wherein the at least one controller is operable responsive at least in part to the determination to cause
   the cash dispenser to operate to provide currency bills from the machine,
   the financial account to be assessed a value corresponding to the provided currency bills,
wherein the at least one document reader is configured to read bill identifying data from machine dispensable currency bills,
wherein the at least one controller is operative to cause data corresponding to the bill identifying data to be stored in at least one data store,
at least one wearable computer device configured to be at least one of worn or carried by an individual,
wherein the at least one wearable computer device includes at least one wearable device reader,
wherein the at least one wearable device reader is configured to read identifying data from an individual received currency bill,
wherein the at least one wearable computer device is in operative connection with the at least one data store,
wherein the at least one wearable computer device is configured to cause a bill source comparison to be made concerning whether bill identifying data read from the received currency bill through operation of the at least one wearable device reader corresponds to identifying data of a bill dispensed through operation of the automated banking machine within a set prior time period.

2. The apparatus according to claim 1,
wherein the automated banking machine and the at least one wearable computer device are located within a single business establishment, wherein the wearable computer device is configured to be worn or carried by an individual employee of the establishment.

3. The apparatus according to claim 1 wherein at least one of
   the bill identifying data corresponds to at least a portion of a bill serial number, and
   the set prior time period is not greater than one day.

4. The apparatus according to claim 1
wherein the at least one wearable computer device includes at least one output device,
wherein the at least one output device is configured to provide at least one output perceivable by the individual indicative of a result of the bill source comparison.

5. The apparatus according to claim 1
wherein the at least one wearable computer device includes at least one biometric feature reader, wherein the at least one biometric feature reader includes an inward facing camera configured to read at least one biometric feature of the wearer individual while being worn,
wherein the at least one wearable computer device is configured to
   make an identity determination that a wearer individual is an authorized operator of the at least one wearable computer device responsive at least in part to the at least one read biometric feature,
   enable at least one function to be performed by the wearable computer device responsive at least in part to the identity determination.

6. The apparatus according to claim 5, wherein the at least one function enabled to be performed by the at least one wearable computer device while being worn includes at least one of
   bill source comparison,
   bill genuineness evaluation,
   check image data production, and
   card genuineness determination.

7. Apparatus comprising:
   a wearable computer device, wherein the wearable computer device is configured to be worn by an individual and includes a configuration of at least one of wearable glasses, a wrist watch, a medallion, a hat and an article of clothing,
   wherein the wearable computer device includes at least one wearable computer reader and at least one output device configured to provide outputs perceivable by the individual,
   wherein the at least one wearable computer reader is configured to read bill indicia from a currency bill while the device is being worn by the individual, and wherein the wearable computer device is configured to
      cause a bill genuineness determination to be made for the currency bill responsive at least in part to the read bill indicia,
      provide at least one output through the at least one output device responsive at least in part to the bill genuineness determination, which at least one output is perceivable by the individual while the device is worn.

8. The apparatus according to claim 7 and further comprising:
   an automated banking machine, wherein the automated banking machine is configured to dispense currency bills to a user and to cause a value to be assessed to an account associated with the user,
   wherein the automated banking machine includes at least one machine bill reader, wherein the at least one machine bill reader is configured to read indicia from currency bills dispensable from the machine,
   wherein the automated banking machine includes at least one controller, wherein the at least one controller is in operative connection with at least one data store, wherein the at least one controller is in operative connection with the at least one machine bill reader and is configured to cause dispensable bill identifying data to be stored in the at least one data store, wherein the wearable computer device is in operative connection with the at least one data store, wherein the wearable computer device is configured to cause
- a bill source determination to be made responsive at least in part to the bill indicia read through operation of the at least one wearable computer reader, that the currency bill was previously dispensed from the automated banking machine within a set prior time period,
- at least one bill source output to be provided through the at least one output device responsive at least in part to the bill source determination wherein the at least one bill source output is indicative that the bill was previously dispensed from the automated banking machine.

9. The apparatus according to claim 7 wherein the at least one wearable computer reader is configured to read card data from a card while the device is worn, wherein the card is usable as at least one of a credit card and a debit card, wherein the wearable computer device is configured to cause
- a card genuineness determination to be made concerning the genuineness of the card responsive at least in part to the card data, and
- at least one card output to be provided through the at least one output device, wherein the at least one card output is indicative of genuineness of the card.

10. The apparatus according to claim 7 wherein the at least one wearable computer reader is operative while the device is worn to read data from a financial check, wherein the wearable computer device is operative to cause
- electronic image data to be produced, wherein the electronic image data corresponds to visual appearance of at least a portion of the check, and
- the electronic image data to be wirelessly sent from the wearable computer device to at least one remote computer.

11. The apparatus according to claim 7 wherein the wearable computer device includes at least one input device, wherein the wearable computer device is configured to
- detect at least one of abnormal movement and abnormal sound adjacent the wearable computer device through operation of the at least one input device when the wearable computer device is not worn by an individual,
- and to cause while the device is not worn at least one wireless alarm signal to be sent to at least one remote computer responsive at least in part to the detection of the at least one of abnormal movement and abnormal sound.

12. Apparatus comprising:

a wearable computer device configured to be at least one of worn or carried by an individual, wherein the wearable computer device includes
  at least one input device,
  at least one output device,
  at least one microprocessor,
  at least one data store,
  at least one wireless transmitter, and
  at least one battery, wherein the at least one input device includes at least one camera configured to capture images of areas adjacent to the wearable computer device, wherein the wearable computer device is configured to capture image data through operation of the at least one camera while the wearable computer device is not worn or carried by an individual, cause evaluation of the image data for abnormal movement, and cause at least one wireless alarm signal to be sent from the wearable computer device responsive to a determination that abnormal movement occurred, and while the wearable computer device is worn or carried by the individual, at least one of
- evaluate a currency bill image captured through operation of the at least one camera and cause at least one output through the at least one output device perceivable by the individual, indicative of whether the currency bill is genuine,
- evaluate a currency bill image captured through operation of the at least one camera and cause a determination to be made that the currency bill was previously dispensed from an automated banking machine, and to cause at least one output through the at least one output device perceivable by the individual indicative that the currency bill was previously dispensed from the automated banking machine,
- evaluate at least one image captured through operation of the at least one camera of a credit or debit card, and to cause at least one output through the at least one output device perceivable by the user indicative of the genuineness of the card, and
- capture at least one image of a check through operation of the at least one camera, produce electronic image data corresponding to visual appearance of at least a portion of the check, and cause the electronic image data to be sent wirelessly from the wearable computer device.

13. Apparatus comprising:

a mobile wireless device, wherein the device is configured to be at least one of worn or carried by an individual, wherein the device includes at least one reader and at least one output device configured to provide outputs perceivable by the individual, wherein the at least one reader is configured to read bill indicia from a currency bill, wherein the device is configured to
- cause a bill genuineness determination to be made for the currency bill responsive at least in part to the read bill indicia,
- provide at least one output through the at least one output device responsive at least in part to the bill genuineness determination, wherein the device includes at least one input device, wherein the device is configured to
- detect at least one of abnormal movement and abnormal sound adjacent the device through operation of the at least one input device when the device is not worn or carried by an individual,
- and cause at least one wireless alarm signal to be sent to at least one remote computer responsive at least in part to the detection of the at least one of abnormal movement and abnormal sound.

14. Apparatus comprising:

an automated banking machine operable responsive at least in part to read user data to cause financial transfers, wherein the machine includes at least one user input device, wherein the at least one user input device includes at least one data reader, wherein the at least one data reader is operable to read user data usable to identify a financial account of a machine user, wherein the machine includes at least one display, wherein the machine includes at least one document reader, wherein the at least one document reader is operative to electronically read data from documents, wherein the machine includes a cash dispenser, wherein the cash dispenser is operable to selectively dispense currency bills from the machine, wherein the machine is associated with at least one controller, wherein the at least one controller is in operative connection with at least one data store, wherein the at least one controller is configured to cause a determination to be made that user data read by the at least one data reader is associated with a financial account on which a transaction is authorized to be conducted through operation of the machine, wherein the at least one controller is operable responsive at least in part to the determination to cause the cash dispenser to operate to provide currency bills from the machine, the financial account to be assessed a value corresponding to the provided currency bills, wherein the at least one document reader is configured to read bill identifying data from machine dispensable currency bills, wherein the at least one controller is operative to cause data corresponding to the bill identifying data to be stored in at least one data store, at least one wearable computer device configured to be worn by an individual, wherein the at least one wearable computer device includes a configuration of at least one of wearable glasses, a wrist watch, a medallion, a hat and an article of clothing, wherein the at least one wearable computer device includes at least one wearable reader, wherein the at least one wearable reader is configured to read identifying data from an individual received currency bill while being worn by the individual, wherein the at least one wearable computer device is in operative connection with the at least one data store, wherein the at least one wearable computer device is configured to cause a bill source comparison to be made concerning whether bill identifying data read from the received currency bill through operation of the at least one wearable reader corresponds to identifying data of a bill dispensed through operation of the automated banking machine.

15. The apparatus according to claim 14 wherein the at least one wearable computer device is configured to use data read from the currency bill by the at least one wearable reader to evaluate genuineness of the currency bill.

16. The apparatus according to claim 15 wherein the at least one wearable computer device is configured to cause the at least one the wearable reader to produce check image data corresponding to visual appearance of an individual received check.

17. The apparatus according to claim 16 wherein the at least one wearable computer device is operable responsive at least in part to the wearable computer device produced image data, to resolve a user received check value associated with the individual received check, and to cause at least one financial transfer corresponding to the user received check value.

18. The apparatus according to claim 17 wherein the at least one wearable computer device is operative to cause card data to be read through operation of the at least one wearable reader from at least one of a credit or debit card, a determination of genuineness of the card to be made responsive at least in part to the read card data.

19. The apparatus according to claim 18 wherein the automated banking machine includes at least one cleaner/disinfecting device, wherein the at least one cleaner/disinfecting device is operable to remove narcotics residue from at least one of currency bills, financial checks and other documents.

20. The apparatus according to claim 15 wherein the at least one wearable computer device includes at least one output device, wherein the at least one output device is configured to provide while being worn at least one output perceivable by the individual indicative of a result of the genuineness evaluation of the currency bill.

* * * * *